(12) United States Patent
Ohgiya et al.

(10) Patent No.: US 7,659,271 B2
(45) Date of Patent: Feb. 9, 2010

(54) PYRIMIDINE COMPOUND HAVING DIBENZYLAMINE STRUCTURE AND MEDICAMENT COMPRISING THE SAME

(75) Inventors: Tadaaki Ohgiya, Saitama (JP); Toru Miura, Tokyo (JP); Ayumu Okuda, Tokyo (JP); Toshiharu Arai, Saitama (JP); Koichi Yamazaki, Tokyo (JP); Taro Aoki, Saitama (JP); Katsutoshi Miyosawa, Saitama (JP); Haruki Shibata, Tokyo (JP); Kimiyuki Shibuya, Saitama (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 12/100,831

(22) Filed: Apr. 10, 2008

(65) Prior Publication Data

US 2009/0082352 A1 Mar. 26, 2009

Related U.S. Application Data

(60) Provisional application No. 60/911,620, filed on Apr. 13, 2007.

(51) Int. Cl.
C07D 239/42 (2006.01)
A61K 31/505 (2006.01)

(52) U.S. Cl. .............. 514/235.8; 514/269; 514/275; 544/122; 544/298; 544/330

(58) Field of Classification Search .............. 544/122, 544/298, 330; 514/235.8, 269, 275
See application file for complete search history.

(56) References Cited

U.S. PATENT DOCUMENTS

| | | |
|---|---|---|
| 6,426,365 B1 | 7/2002 | Shinkai et al. |
| 2005/0059810 A1 | 3/2005 | Maeda et al. |
| 2006/0178514 A1 | 8/2006 | Baruah et al. |
| 2006/0270705 A1 | 11/2006 | Yonemori et al. |
| 2007/0015758 A1 | 1/2007 | Baruah et al. |
| 2009/0023729 A1 | 1/2009 | Nakamura et al. |
| 2009/0029994 A1 | 1/2009 | Nakamura et al. |
| 2009/0054474 A1 | 2/2009 | Ohgiya et al. |
| 2009/0062306 A1 | 3/2009 | Ohgiya et al. |

FOREIGN PATENT DOCUMENTS

| | | |
|---|---|---|
| EP | 1 020 439 | 7/2000 |
| JP | 11-49743 | 2/1999 |
| JP | 2003-221376 | 8/2003 |
| WO | 98/35937 | 8/1998 |
| WO | 00/17164 | 3/2000 |
| WO | 00/17165 | 3/2000 |
| WO | 00/17166 | 3/2000 |
| WO | 03/063868 | 8/2003 |
| WO | 2004/020393 | 3/2004 |
| WO | 2005/095395 | 10/2005 |
| WO | 2006/056854 | 6/2006 |
| WO | 2006/073973 | 7/2006 |
| WO | 2006/098394 | 9/2006 |
| WO | 2007/041494 | 4/2007 |
| WO | 2007/073934 | 7/2007 |
| WO | 2007/075194 | 7/2007 |
| WO | 2007/088996 | 8/2007 |
| WO | 2007/088999 | 8/2007 |
| WO | 2007/126043 | 11/2007 |
| WO | 2007/128568 | 11/2007 |
| WO | 2008/018529 | 2/2008 |

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, Aug. 2002.*
English Language Abstract of JP 11-49743.
de Grooth, G.J. et al. Efficacy and Safety of a Novel Cholesteryl Ester Transfer Protein Inhibitor, JTT-705, in Humans, *Circulation*, vol. 105, No. 18, pp. 2159-2165 (2002).
Usui et al., "A New On-line Dual Enzymatic Method for Simultaneous Quantification of Cholesterol and Triglycerides in Lipoproteins by HPLC," Journal of Lipid Research, vol. 43, pp. 805-814 (2002).
English Language Abstract of JP 2003-221376.

(Continued)

*Primary Examiner*—Deepak Rao
(74) *Attorney, Agent, or Firm*—Greenblum & Bernstein, P.L.C.

(57) ABSTRACT

A compound represented by the following general formula (I), wherein $R^1$, $R^2$, $R^3$, $R^4$ and $R^5$ represent hydrogen atom, a halo(lower alkyl) group, cyano group and the like, $R^6$ represents an alkyl group, a cycloalkyl group and the like, $R^7$, $R^8$, $R^9$ and $R^{10}$ represent hydrogen atom, a halogen atom, a lower alkyl group, a halo(lower alkyl) group and the like, $R^{11}$ and $R^{12}$ represent hydrogen atom, a lower alkyl group, a (lower cycloalkyl) (lower alkyl) group and the like, and $R^{13}$ represents hydrogen atom, a halogen atom, a lower alkoxy group and the like, which has potent inhibitory activity on cholesterol ester transfer protein (CETP).

(I)

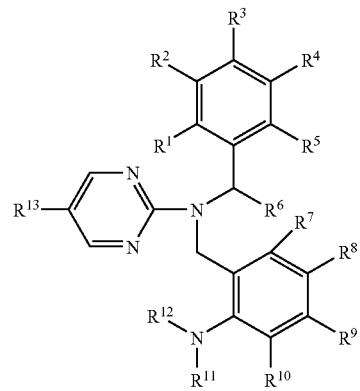

6 Claims, 1 Drawing Sheet

OTHER PUBLICATIONS

U.S. Appl. No. 11/835,127 to Ohgiya et al., entitled "Novel Pyrimidine Compounds Having Benzyl(Pyridylmethyl)Amine-Strucute and Medicament Comprising the Same," filed on Aug. 7, 2007.

U.S. Appl. No. 12/045,982 to Ohgiya et al., entitled "Novel Pyrimidine Compound Having Benzyl (Heterocyclylmethyl)Amine Structure and Medicament Comprising the Same;" filed on Mar. 11, 2008.

Gomtsyan et al., Bioorganic & Medicinal Chemistry Letters, 2007, vol. 17, pp. 3894-3899.

H. Takahashi et al., Bioorganic & Medicinal Chemistry Letters, 2007, vol. 17, pp. 5091-5095.

* cited by examiner

[Fig. 1]
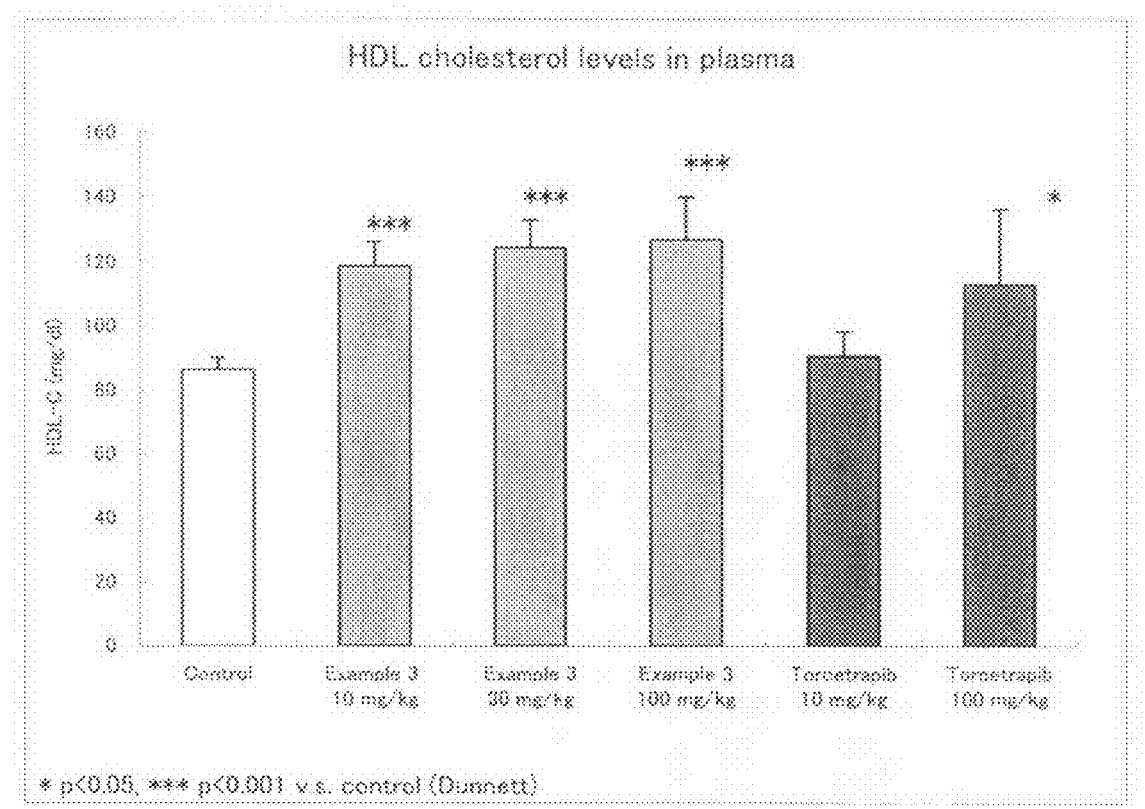

PYRIMIDINE COMPOUND HAVING DIBENZYLAMINE STRUCTURE AND MEDICAMENT COMPRISING THE SAME

This application claims the benefit of U.S. Provisional Application 60/911,620 filed Apr. 13, 2007.

TECHNICAL FIELD

The present invention relates to a novel pyrimidine compound having a dibenzylamine structure having an inhibitory activity against cholesterol ester transfer protein (CETP), and a medicament comprising the same.

BACKGROUND ART

In recent years, dyslipidemia (hyperlipidemia) and arteriosclerotic diseases resulting therefrom have been rapidly increasing due to changes into high calorie and high cholesterol-type diet with improvements in living standard, obesity, lack of exercise, aging, and the like. Because a level of low density lipoprotein (LDL) cholesterol and level of triglyceride positively correlate with incidence rate of heart diseases, conventional pharmacotherapies for dyslipidemia and arteriosclerosis have been focused on reduction of blood lipids. Whilst, it has been revealed by many researches so far that a level of high density lipoprotein (HDL) cholesterol in plasma negatively correlates with the onset of ischemic heart diseases, and hypo-HDL-emia is considered as one of risk factors of arteriosclerosis. However, no medicament which selectively and markedly raises an HDL level is available at present, and development of such a medicament has been desired.

Cholesterol ester transfer protein (CETP) is an extremely hydrophobic protein which transfers a cholesterol ester from HDL cholesterol to LDL cholesterol, very low density lipoprotein (VLDL) cholesterol or the like, and HDL cholesterol can be increased by inhibiting the transfer by CETP.

Niacin significantly increases HDL cholesterol, but has a serious problem of resistance which reduces compliance, i.e., causes hot flash, vertigo, palpitation, and the like. Although fibrates and HMG-CoA reductase inhibitors slightly increase an HDL cholesterol level (10 to 12%), they do not sufficiently satisfy medical needs of achieving significant increase of a plasma HDL cholesterol level to delay progress of atherosclerosis. Whilst, the CETP inhibitor attains a potent increase of an HDL cholesterol level, so that it can be anticipated to provide degeneration of arteriosclerotic lesions to an extent which cannot be exceeded by neither fibrates nor HMG-CoA reductase inhibitors, and thus it is considered to be possible to provide prophylactic or therapeutic agents for arteriosclerosis or dyslipidemia, which are conventionally unavailable. The CETP inhibitors attain the increase in HDL cholesterol and the decrease in LDL cholesterol or VLDL cholesterol by a mechanism different from that of HMG-CoA reductase inhibitors, and accordingly, a combinational effect of a CETP inhibitor and a HMG-CoA reductase inhibitor can also be expected.

CETP is mainly produced in the liver and small intestine in the case of human, and it is possible that CETP expressed in the small intestine participates in lipid absorption. There is also a report aiming at achieving lipid absorption inhibitory effect by inhibiting CETP of the small intestine (Patent document 1).

Several reports have been made so far about compounds to inhibit CETP activity. For example, a thiol derivative which forms a disulfide bond by a reaction with a cysteine residue of CETP to inhibit the CETP activity has been reported (Patent document 2, Non-patent document 1). However, the thiol derivative requires a large amount of administration for expression of the action, and side reactions by formation of disulfide bond with other proteins are concerned. In addition, there is no description suggesting the compounds of the present invention.

As CETP inhibitors having a mode of action different from that of the thiol derivative, tetrahydroquinoline derivatives have been disclosed (Patent documents 3 to 5). However, these derivatives are highly liposoluble compounds, and due to low oral absorption resulting from the low water-solubility, they require a pharmaceutical means for obtaining a blood level sufficient for expression of the efficacy (Patent document 6). In addition, there is no description suggesting the compounds of the present invention.

Further, tetrahydronaphthylidine derivatives, benzyl(heterocyclylmethyl)amine derivatives and the like are disclosed as compounds having CETP inhibitory activities (Patent documents 7 to 9). However, they are highly liposoluble compounds in the same manner as the aforementioned tetrahydroquinoline derivatives. In addition, there is no description suggesting the compounds of the present invention.

Furthermore, compounds having a dibenzylamine structure are disclosed (Patent document 10). However, they do not have a substituent such as a lower alkyl group on the carbon atom at the benzylic position, unlike the pyrimidine compounds of the present invention having a dibenzylamine structure, and there is no description suggesting the compounds of the present invention. Moreover, they are found to have insufficient CETP inhibitory activity.

Patent document 1: International Patent Publication WO2006/098394
Patent document 2: Japanese Patent Unexamined Publication (Kokai) No. 11-49743
Patent document 3: International Patent Publication WO2000/17164
Patent document 4: International Patent Publication WO2000/17165
Patent document 5: International Patent Publication WO2000/17166
Patent document 6: International Patent Publication WO2003/63868
Patent document 7: International Patent Publication WO2005/095395
Patent document 8: International Patent Publication WO2006/056854
Patent document 9: International Patent Publication WO2006/073973
Patent document 10: International Patent Publication WO2004/020393
Non-patent document 1: Circulation, 105(18), 2159-2165 (2002)

DISCLOSURE OF THE INVENTION

Object to be Achieved by the Invention

Therefore, an object of the present invention is to create a novel compound having a potent inhibitory activity against CETP.

Means for Achieving the Object

The inventors of the present invention conducted various researches to achieve the aforementioned object. As a result, they found that compounds represented by the general formula (I) and salts thereof as well as solvates thereof had superior CETP inhibitory activity and achieved the present invention:

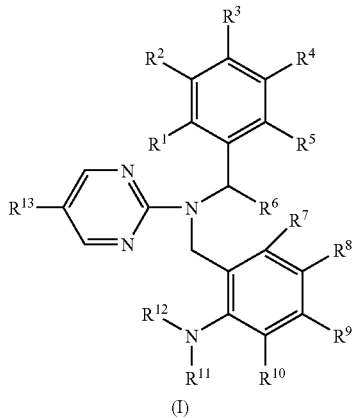

[Formula 1]

(wherein, $R^1$, $R^2$, $R^3$, $R^4$ and $R^5$ are the same or different, and represent hydrogen atom, a halogen atom, a lower alkyl group, a halo(lower alkyl) group, a lower alkoxy group, a halo(lower alkoxy) group, hydroxy group, cyano group, nitro group, a (lower alkyl)thio group, a (lower alkyl)sulfinyl group, a (lower alkyl)sulfonyl group, a (lower alkyl)sulfonylamino group, a halo(lower alkyl)sulfonylamino group, an arylsulfonylamino group, an amino group which may have a substituent, carboxyl group, a (lower alkyl)carbonyl group, or a (lower alkoxy)carbonyl group, $R^6$ represents a lower alkyl group, a halo(lower alkyl) group, a lower cycloalkyl group, or a (lower cycloalkyl)(lower alkyl) group, $R^7$, $R^8$, $R^9$ and $R^{10}$ are the same or different, and represent hydrogen atom, a halogen atom, a lower alkyl group, a lower cycloalkyl group, a (lower cycloalkyl)(lower alkyl) group, a halo(lower alkyl) group, a lower alkoxy group, a halo(lower alkoxy) group, a (lower alkoxy)(lower alkoxy) group, hydroxy group, cyano group, nitro group, a (lower alkyl)thio group, a (lower alkyl)sulfinyl group, a (lower alkyl)sulfonyl group, a (lower alkyl)sulfonylamino group, a halo(lower alkyl)sulfonylamino group, an arylsulfonylamino group, an amino group which may have a substituent, carboxyl group, a (lower alkyl)carbonyl group, or a (lower alkoxy)carbonyl group, $R^{11}$ and $R^{12}$ are the same or different, and represent hydrogen atom, a lower alkyl group, a (lower cycloalkyl)(lower alkyl) group which may have a substituent, an aryl group, an aryl(lower alkyl) group which may have a substituent, or a lower cycloalkyl group, or $R^{11}$ and $R^{12}$ may combine to form a nitrogen-containing saturated heterocyclic ring which may have a substituent together with the adjacent nitrogen atom, $R^{13}$ represents hydrogen atom, a halogen atom, a lower alkoxy group, a (lower alkyl)thio(lower alkoxy) group, a (lower alkyl)sulfinyl(lower alkoxy) group, a (lower alkyl)sulfonyl(lower alkoxy) group, an aryl(lower alkoxy) group which may have a substituent, hydroxy group, a (lower alkyl)amino group, a di(lower alkyl)amino group, a (lower alkyl)thio(lower alkyl)amino group, a (lower alkyl)sulfinyl(lower alkyl)amino group, a (lower alkyl)sulfonyl(lower alkyl) amino group, an arylamino group, a cyclic amino group which may have a hetero atom as a ring-constituting atom, a (lower alkoxy)(lower alkoxy) group, a (lower alkoxy)(lower alkyl)amino group, a hydroxy(lower alkoxy) group, a hydroxy(lower alkyl)amino group, an acylamino group, a (lower alkyl)sulfonylamino group, a hydroxycarbonyl(lower alkoxy) group, an amino(lower alkoxy) group, a (lower alkyl) amino(lower alkoxy) group, or a di(lower alkyl)amino(lower alkoxy) group, and the general formula (I) represents both individual enantiomers and mixtures thereof).

The pyrimidine compounds having a dibenzylamine structure of the present invention are novel compounds, and they are structurally completely different from known compounds having a CETP inhibitory activity especially in that they have a substituent on the carbon atom at the benzylic position ($R^6$ in the aforementioned general formula).

Namely, the present invention provides a compound represented by the aforementioned general formula (I) or a salt thereof, or a solvate thereof.

The present invention also provides a medicament comprising a compound represented by aforementioned general formula (I) or a salt thereof, or a solvate thereof as an active ingredient, preferably such a medicament for prophylactic or therapeutic treatment of diseases including dyslipidemia (hyperlipidemia), arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like.

The present invention also provides a CETP inhibitor and an HDL-increasing agent comprising a compound represented by aforementioned general formula (I) or a salt thereof, or a solvate thereof as an active ingredient.

The present invention further provides a pharmaceutical composition comprising a compound represented by the aforementioned general formula (I) or a salt thereof, or a solvate thereof and a pharmaceutically acceptable carrier.

The present invention further provides a method for prophylactic or therapeutic treatment of diseases including dyslipidemia (hyperlipidemia), arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like, which comprises the step of administering an effective amount of a compound represented by the aforementioned general formula (I) or a salt thereof, or a solvate thereof to a mammal including human.

The present invention also provides a method for inhibiting CETP in living body of a mammal including human, which comprises the step of administering an effective amount of a compound represented by the aforementioned general formula (I) or a salt thereof, or a solvate thereof to a mammal including human.

The present invention also provides a method for increasing blood HDL cholesterol level in living body of a mammal including human, which comprises the step of administering an effective amount of a compound represented by the aforementioned general formula (I) or a salt thereof, or a solvate thereof to a mammal including human.

The present invention further provides use of a compound represented by the aforementioned general formula (I) or a salt thereof, or a solvate thereof for the manufacture of a pharmaceutical preparation for prophylactic or therapeutic treatment of diseases including dyslipidemia (hyperlipidemia), arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like.

The present invention also provides use of a compound represented by the aforementioned general formula (I) or a salt thereof, or a solvate thereof for the manufacture of a pharmaceutical preparation for inhibiting CETP in a living body of mammal including human.

The present invention also provides use of a compound represented by the aforementioned general formula (I) or a salt thereof, or a solvate thereof for the manufacture of a pharmaceutical preparation for increasing blood HDL cholesterol level in a living body of mammal including human.

The present invention further provides a medicament comprising a combination of (a) a compound represented by the aforementioned general formula (I) or a salt thereof, or a solvate thereof and (b) an HMG-CoA reductase inhibitor, preferably such a medicament for prophylactic or therapeutic treatment of diseases including dyslipidemia (hyperlipidemia), arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like.

The present invention further provides a combinatory pharmaceutical composition comprising (a) a compound represented by the aforementioned general formula (I) or a salt thereof, or a solvate thereof, and (b) an HMG-CoA reductase inhibitor.

EFFECT OF THE INVENTION

The compound of the present invention represented by the aforementioned general formula (I), or a salt thereof, or a solvate thereof exhibits potent inhibitory activity against CETP and potent blood HDL cholesterol increasing action, as specifically demonstrated in the test examples mentioned later, and therefore it can be suitably used as an active ingredient of a CETP inhibitor, and further as an active ingredient of an HDL-increasing agent.

Furthermore, on the basis of the CETP inhibitory activity and the blood HDL cholesterol increasing action, the compound of the present invention represented by the aforementioned general formula (I), or a salt thereof, or a solvate thereof can be suitably used as an active ingredient of a medicament, preferably a medicament for prophylactic or therapeutic treatment of diseases including dyslipidemia (hyperlipidemia), arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like. Moreover, the compound of the present invention or a salt thereof, or a solvate thereof can also be preferably used as an active ingredient of the aforementioned medicament showing low CYP inhibitory action.

BRIEF EXPLANATION OF THE DRAWING

FIG. 1 is a graph showing blood HDL cholesterol levels in plasma of hamsters repeatedly administered with N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfonyl)ethoxy]pyrimidin-2-amine (Example 3) over seven days at doses of 10 mg/kg, 30 mg/kg and 100 mg/kg.

BEST MODE OF CARRYING OUT THE INVENTION

Examples of the lower alkyl group as the lower alkyl group or the lower alkyl group of the halo(lower alkyl) group, the (lower cycloalkyl)(lower alkyl) group, the aryl(lower alkyl) group, the hydroxycarbonyl(lower alkyl) group, and the (lower alkoxy)carbonyl(lower alkyl) group referred to in the present invention include a linear or branched alkyl group having 1 to 6 carbon atoms (referred to as $C_1$-$C_6$ alkyl), for example, methyl group, ethyl group, n-propyl group, isopropyl group, n-butyl group, isobutyl group, t-butyl group, n-pentyl group, 2-methylbutyl group, 2,2-dimethylpropyl group and the like.

Examples of the lower alkoxy group as the lower alkoxy group or the lower alkoxy group of the halo(lower alkoxy) group, the (lower alkyl)thio(lower alkoxy) group, the (lower alkyl)sulfinyl(lower alkoxy) group, the (lower alkyl)sulfonyl (lower alkoxy) group, the aryl(lower alkoxy) group, the (lower alkoxy)(lower alkoxy) group, the (lower alkoxy)(lower alkyl)amino group, the hydroxy(lower alkoxy) group, the hydroxycarbonyl(lower alkoxy) group, the amino(lower alkoxy) group, the (lower alkyl)amino(lower alkoxy) group, and the di(lower alkyl)amino(lower alkoxy) group referred to in the present invention include a linear or branched alkoxy group having 1 to 6 carbon atoms (referred to as $C_1$-$C_6$ alkoxy), for example, methoxy group, ethoxy group, n-propoxy group, isopropoxy group, n-butoxy group, isobutoxy group, t-butoxy group, n-pentyloxy group, 2-methylbutoxy group, 2,2-dimethylpropoxy group and the like.

Examples of the (lower alkyl)thio group as the (lower alkyl)thio group or the (lower alkyl)thio group of the (lower alkyl)thio(lower alkoxy) group and the (lower alkyl)thio (lower alkyl)amino group referred to in the present invention include a linear or branched alkylthio group having 1 to 6 carbon atoms (referred to as ($C_1$-$C_6$ alkyl)thio), for example, methylthio group, ethylthio group, n-propylthio group, isopropylthio group, n-butylthio group, isobutylthio group, t-butylthio group, n-pentylthio group, 2-methylbutylthio group, 2,2-dimethylpropylthio group and the like.

Examples of the (lower alkyl)sulfinyl group as the (lower alkyl)sulfinyl group or the (lower alkyl)sulfinyl group of the (lower alkyl)sulfinyl(lower alkoxy) group, and the (lower alkyl)sulfinyl(lower alkyl)amino group referred to in the present invention include a linear or branched alkylsulfinyl group having 1 to 6 carbon atoms (referred to as ($C_1$-$C_6$ alkyl)sulfinyl), for example, methylsulfinyl group, ethylsulfinyl group, n-propylsulfinyl group, isopropylsulfinyl group, n-butylsulfinyl group, isobutylsulfinyl group, t-butylsulfinyl group, n-pentylsulfinyl group, 2-methylbutylsulfinyl group, 2,2-dimethylpropylsulfinyl group and the like.

Examples of the (lower alkyl)sulfonyl group as the (lower alkyl)sulfonyl group or the (lower alkyl)sulfonyl group of the (lower alkyl)sulfonyl(lower alkoxy) group and the (lower alkyl)sulfonyl(lower alkyl)amino group referred to in the present invention include a linear or branched alkylsulfonyl group having 1 to 6 carbon atoms (referred to as ($C_1$-$C_6$ alkyl)sulfonyl), for example, methylsulfonyl group, ethylsulfonyl group, n-propylsulfonyl group, isopropylsulfonyl group, n-butylsulfonyl group, isobutylsulfonyl group, t-butylsulfonyl group, n-pentylsulfonyl group, 2-methylbutylsulfonyl group, 2,2-dimethylpropylsulfonyl group and the like.

Examples of the (lower alkyl)carbonyl group referred to in the present invention include a linear or branched alkylcarbonyl group having 2 to 6 carbon atoms (referred to as ($C_2$-$C_6$ alkyl)carbonyl), for example, methylcarbonyl group, ethylcarbonyl group, n-propylcarbonyl group, isopropylcarbonyl group, n-butylcarbonyl group, isobutylcarbonyl group, t-butylcarbonyl group, n-pentylcarbonyl group, 2-methylbutylcarbonyl group, 2,2-dimethylpropylcarbonyl group and the like.

Examples of the (lower alkoxy)carbonyl group as the (lower alkoxy)carbonyl group or the (lower alkoxy)carbonyl group of the (lower alkoxy)carbonyl(lower alkyl) group referred to in the present invention include a linear or branched alkoxycarbonyl group having 2 to 6 carbon atoms (referred to as ($C_2$-$C_6$ alkoxy)carbonyl), for example, methoxycarbonyl group, ethoxycarbonyl group, n-propoxycarbonyl group, isopropoxycarbonyl group, n-butoxycarbonyl group, isobutoxycarbonyl group, t-butoxycarbonyl group, n-pentyloxycarbonyl group, 2-methylbutoxycarbonyl group, 2,2-dimethylpropoxycarbonyl group and the like.

Examples of the acylamino group referred to in the present invention include a linear or branched acylamino group having 2 to 6 carbon atoms (referred to as ($C_2$-$C_6$ acyl)amino), for example, acetylamino group, n-propionylamino group, isopropionylamino group, butyrylamino group, isobutyrylamino group, t-butyrylamino group, n-pentanoylamino group, 2-methylbutyrylamino group, 2,2-dimethylpropionylamino group and the like.

Examples of the (lower alkyl)amino group as the (lower alkyl)amino group or the (lower alkyl)amino group of the (lower alkyl)thio(lower alkyl)amino group, the (lower alkyl)sulfinyl(lower alkyl)amino group, the (lower alkyl)sulfonyl(lower alkyl)amino group, the (lower alkoxy)(lower alkyl)amino group, the hydroxy(lower alkyl)amino group, and the (lower alkyl)amino(lower alkoxy) group referred to in the present invention include a linear or branched alkylamino group having 1 to 6 carbon atoms (referred to as ($C_1$-$C_6$ alkyl)amino), for example, methylamino group, ethylamino group, n-propylamino group, isopropylamino group, n-butylamino group, isobutylamino group, t-butylamino group, n-pentylamino group, 2-methylbutylamino group, 2,2-dimethylpropylamino group and the like.

Examples of the di(lower alkyl)amino group as the di(lower alkyl)amino group or the di(lower alkyl)amino group of the di(lower alkyl)amino(lower alkoxy) group referred to in the present invention include an amino group substituted with two linear or branched alkyl groups each having 1 to 6 carbon atoms, which may be the same or different (referred to as di($C_1$-$C_6$ alkyl)amino), for example, (ethyl)(methyl)amino group, (isopropyl)(n-propyl)amino group, (n-butyl)(isobutyl)amino group, (t-butyl)(n-pentyl)amino group, (2,2-dimethylpropyl)(2-methylbutyl)amino group and the like.

Examples of the (lower alkyl)sulfonylamino group as the (lower alkyl)sulfonylamino group or the (lower alkyl)sulfonylamino group of the halo(lower alkyl)sulfonylamino group referred to in the present invention include a linear or branched alkylsulfonylamino group having 1 to 6 carbon atoms (referred to as ($C_1$-$C_6$ alkyl)sulfonylamino), for example, methylsulfonylamino group, ethylsulfonylamino group, n-propylsulfonylamino group, isopropylsulfonylamino group, n-butylsulfonylamino group, isobutylsulfonylamino group, t-butylsulfonylamino group, n-pentylsulfonylamino group, 2-methylbutylsulfonylamino group, 2,2-dimethylpropylsulfonylamino group and the like.

Examples of the lower cycloalkyl group as the lower cycloalkyl group or the lower cycloalkyl group of the (lower cycloalkyl)(lower alkyl) group referred to in the present invention include a cycloalkyl group having 3 to 8 carbon atoms (referred to as $C_3$-$C_8$ cycloalkyl), for example, cyclopropyl group, cyclobutyl group, cyclopentyl group, cyclohexyl group and the like.

Examples of the aryl group as the aryl group or the aryl group of the aryl(lower alkyl) group, the aryl(lower alkoxy) group, the arylamino group and the arylsulfonylamino group referred to in the present invention include an aryl group having 6 to 10 carbon atoms (referred to as $C_6$-$C_{10}$ aryl), for example, phenyl group, naphthyl group and the like.

Examples of the halogen atom as the halogen atom or the halogen atom of the halo(lower alkyl) group and the halo(lower alkoxy) group referred to in the present invention include fluorine atom, chlorine atom, bromine atom, iodine atom and the like.

In the general formula (I), examples of the halo(lower alkyl) group as $R^1$, $R^2$, $R^3$, $R^4$ and $R^5$ include, for example, a lower alkyl group substituted with 1 to 5 halogen atoms such as trifluoromethyl group, 2,2,2-trifluoroethyl group and pentafluoroethyl group, and trifluoromethyl group is preferred. Further, examples of the halo(lower alkoxy) group include, for example, a lower alkoxy group substituted with 1 to 5 halogen atoms such as trifluoromethoxy group, 2,2,2-trifluoroethoxy group and pentafluoroethoxy group.

In the general formula (I), examples of the substituent of the amino group which may have a substituent as $R^1$, $R^2$, $R^3$, $R^4$ and $R^5$ include, for example, a lower alkyl group, a halo(lower alkyl) group, an aryl group and the like. The amino group may have 1 or 2 of these substituents.

As for $R^1$, $R^2$, $R^3$, $R^4$ and $R^5$ in the general formula (I), it is preferred that each group, the same or different, is hydrogen atom, a halogen atom, a $C_1$-$C_6$ alkyl group, a halo($C_1$-$C_6$ alkyl) group, a $C_1$-$C_6$ alkoxy group, a halo($C_1$-$C_6$ alkoxy) group, or cyano group, it is more preferred that each group, the same or different, is hydrogen atom, halo($C_1$-$C_6$ alkyl) group, or cyano group, and it is particularly preferred that $R^1$, $R^3$ and $R^5$ are hydrogen atoms, and each of $R^2$ and $R^4$, the same or different, is a halo($C_1$-$C_6$ alkyl) group or cyano group.

In the general formula (I), examples of the lower alkyl group as $R^6$ include, for example, methyl group, ethyl group and the like. As the lower alkyl group as $R^6$, a linear or branched alkyl group having 1 to 4 carbon atoms is more preferred, methyl group or ethyl group is still more preferred, and methyl group is particularly preferred.

In the general formula (I), examples of the halo(lower alkyl) group as $R^6$ include, for example, a lower alkyl group substituted with 1 to 5 halogen atoms such as monofluoromethyl group, difluoromethyl group, trifluoromethyl group, 2,2,2-trifluoroethyl group and pentafluoroethyl group and the like.

In the general formula (I), examples of the lower cycloalkyl group as $R^6$ include, for example, cyclopropyl group, cyclobutyl group, cyclopentyl group and the like.

In the general formula (I), examples of the (lower cycloalkyl)(lower alkyl) group as $R^6$ include, for example, a ($C_3$-$C_8$ cycloalkyl)($C_1$-$C_6$ alkyl) group such as cyclopropylmethyl group and cyclopentylmethyl group.

In the general formula (I), it is preferred that $R^6$ is a $C_1$-$C_6$ alkyl group, a halo($C_1$-$C_6$ alkyl) group, a $C_3$-$C_8$ cycloalkyl group, or a ($C_3$-$C_8$ cycloalkyl)($C_1$-$C_6$ alkyl) group, it is more preferred that $R^6$ is a $C_1$-$C_6$ alkyl group, it is still more preferred that $R^6$ is methyl group or ethyl group, and it is particularly preferred that $R^6$ is methyl group.

In the general formula (I), examples of the halogen atom as $R^7$, $R^8$, $R^9$ and $R^{10}$ include, for example, fluorine atom, chlorine atom, bromine atom and the like.

In the general formula (I), examples of the lower alkyl group as $R^7$, $R^8$, $R^9$ and $R^{10}$ include, for example, methyl group and the like. As the lower alkyl group as $R^7$, $R^8$, $R^9$ and $R^{10}$, a linear or branched alkyl group having 1 to 4 carbon atoms is more preferred, methyl group or ethyl group is still more preferred, and methyl group is particularly preferred.

In the general formula (I), examples of the halo(lower alkyl) group as $R^7$, $R^8$, $R^9$ and $R^{10}$ include, for example, a lower alkyl group substituted with 1 to 5 halogen atoms such as trifluoromethyl group, 2,2,2-trifluoroethyl group and pentafluoroethyl group, and trifluoromethyl group is preferred.

In the general formula (I), examples of the lower alkoxy group as $R^7$, $R^8$, $R^9$ and $R^{10}$ include, for example, methoxy group and the like. As the lower alkoxy group as $R^7$, $R^8$, $R^9$ and $R^{10}$, a linear or branched alkoxy group having 1 to 4 carbon atoms is more preferred, methoxy group or ethoxy group is still more preferred, and methoxy group is particularly preferred.

In the general formula (I), examples of the substituent of the amino group which may have a substituent as $R^7$, $R^8$, $R^9$ and $R^{10}$ include, for example, a lower alkyl group, a halo(lower alkyl) group, an aryl group and the like.

As for $R^7$, $R^8$, $R^9$ and $R^{10}$ in the general formula (I), it is preferred that each group, the same or different, is hydrogen atom, a halogen atom, a $C_1$-$C_6$ alkyl group, a halo($C_1$-$C_6$ alkyl) group, or a $C_1$-$C_6$ alkoxy group, and it is more preferred that $R^7$, $R^9$ and $R^{10}$ are hydrogen atoms, and $R^8$ is a halogen atom, a $C_1$-$C_6$ alkyl group, a halo($C_1$-$C_6$ alkyl) group, or a $C_1$-$C_6$ alkoxy group.

As a preferred embodiment of the combination of $R^7$, $R^8$, $R^9$ and $R^{10}$, it is preferred that at least one of $R^8$, $R^9$ and $R^{10}$ is a halogen atom, and the remainders of $R^7$, $R^8$, $R^9$ and $R^{10}$ are hydrogen atoms, and it is more preferred that $R^7$, $R^9$ and $R^{10}$ are hydrogen atoms, and $R^8$ is a halogen atom, more preferably bromine atom.

As another preferred embodiment of the combination of $R^7$, $R^8$, $R^9$ and $R^{10}$, it is preferred that $R^8$ is a $C_1$-$C_6$ alkyl group, and each of $R^7$, $R^9$ and $R^{10}$, the same or different, is hydrogen atom or a halogen atom, and it is more preferred that $R^8$ is a $C_1$-$C_6$ alkyl group, and $R^7$, $R^9$ and $R^{10}$ are hydrogen atoms.

As another preferred embodiment of the combination of $R^7$, $R^8$, $R^9$ and $R^{10}$, it is preferred that at least one of $R^8$ and $R^9$ is a halo($C_1$-$C_6$ alkyl) group, and the remainders of $R^7$, $R^8$, $R^9$ and $R^{10}$ are hydrogen atoms, and it is more preferred that $R^8$ is a halo($C_1$-$C_6$ alkyl) group, and $R^7$, $R^9$, $R^{10}$ are hydrogen atoms.

As another preferred embodiment of the combination of $R^7$, $R^8$, $R^9$ and $R^{10}$, it is preferred that at least one of $R^8$ and $R^9$ is a $C_1$-$C_6$ alkoxy group, and the remainders of $R^7$, $R^8$, $R^9$ and $R^{10}$ are hydrogen atoms, and it is more preferred that $R^8$ is a $C_1$-$C_6$ alkoxy group, and $R^7$, $R^9$ and $R^{10}$ are hydrogen atoms.

In the general formula (I), examples of the lower alkyl group as $R^{11}$ and $R^{12}$ include, for example, methyl group, ethyl group, n-propyl group and the like. As the lower alkyl group as $R^{11}$ and $R^{12}$, a linear or branched alkyl group having 1 to 4 carbon atoms is more preferred, methyl group or ethyl group is still more preferred, and ethyl group is particularly preferred.

In the general formula (I), examples of the (lower cycloalkyl)(lower alkyl) group as $R^{11}$ and $R^{12}$ include, for example, a ($C_3$-$C_8$ cycloalkyl)($C_1$-$C_6$ alkyl) group such as cyclopropylmethyl group, cyclobutylmethyl group, cyclopentylmethyl group, cyclohexylmethyl group, cyclopropylethyl group, cyclobutylethyl group, cyclopentylethyl group and cyclohexylethyl group. As the (lower cycloalkyl)(lower alkyl) group as $R^{11}$ and $R^{12}$, a ($C_3$-$C_8$ cycloalkyl)($C_1$-$C_6$ alkyl) group is preferred, cyclopropylmethyl group, cyclopentylmethyl group, or cyclohexylmethyl group is still more preferred, and cyclopropylmethyl group, or cyclopentylmethyl group is particularly preferred.

In the general formula (I), examples of the substituent of the (lower cycloalkyl)(lower alkyl) group which may have a substituent as $R^{11}$ and $R^{12}$ include, for example, a lower alkyl group, a halo(lower alkyl) group, hydroxycarbonyl group, a (lower alkoxy)carbonyl group, hydroxycarbonyl(lower alkyl) group, a (lower alkoxy)carbonyl(lower alkyl) group and the like, and a hydroxycarbonyl($C_1$-$C_6$ alkyl) group, or a ($C_1$-$C_6$ alkoxy)carbonyl($C_1$-$C_6$ alkyl) group is preferred. Although the substitution position of the substituent is not particularly limited, it is preferred that it substitutes on the lower cycloalkyl group in the present invention. The number of the substituent is preferably 1 to 3. Examples of the (lower cycloalkyl)(lower alkyl) group having such a substituent include, for example, a ($C_3$-$C_8$ cycloalkyl)($C_1$-$C_6$ alkyl) group having one hydroxycarbonyl($C_1$-$C_6$ alkyl) group or ($C_1$-$C_6$ alkoxy)carbonyl($C_1$-$C_6$ alkyl) group on the cycloalkyl group as the substituent, such as {4-[(hydroxycarbonyl)methyl]-cyclohexyl}methyl group and {4-[(ethoxycarbonyl)methyl]cyclohexyl}methyl group.

In the general formula (I), examples of the nitrogen-containing saturated heterocyclic ring formed by combined $R^{11}$ and $R^{12}$ together with the adjacent nitrogen atom include, for example, a 5- to 8-membered nitrogen-containing saturated heterocyclic ring, which may have one or two or more kinds of 1 or 2 hetero atoms selected from the group consisting of nitrogen atom, oxygen atom and sulfur atom in addition to the nitrogen atom adjacent to $R^{11}$ and $R^{12}$, such as pyrrolidino group, piperidino group, homopiperidino group and morpholino group. The nitrogen-containing saturated heterocyclic ring formed by combined $R^{11}$ and $R^{12}$ together with the adjacent nitrogen atom may have a substituent, and examples of the substituent include, for example, a lower alkyl group, a halo(lower alkyl) group, a lower cycloalkyl group and the like. Number of the substituent is preferably 1 or 2. Examples of the nitrogen-containing saturated heterocyclic ring formed by combined $R^{11}$ and $R^{12}$ together with the adjacent nitrogen atom having such a substituent include a piperidino group or morpholino group having 1 or 2 of $C_1$-$C_6$ alkyl groups as the substituent, such as 4-methylpiperidino group and cis-2,6-dimethylmorpholino group.

In the general formula (I), examples of the substituent of the aryl(lower alkyl) group which may have a substituent as $R^{11}$ and $R^{12}$ include, for example, a halogen atom, a lower alkyl group, a halo(lower alkyl) group, a lower alkoxy group, a halo(lower alkoxy) group, and cyano group. Number of the substituent is preferably 1 to 3. Although the substitution position of the substituent is not particularly limited, the substituent preferably substitutes on the aryl ring of the aryl (lower alkyl) group in the present invention. Examples of such a group include a phenyl($C_1$-$C_6$ alkyl) group which may have a $C_1$-$C_6$ alkoxy group on the phenyl group as the substituent, for example, 4-methoxybenzyl group and the like.

In the general formula (I), it is preferred that each of $R^{11}$ and $R^{12}$, the same or different, is a $C_1$-$C_6$ alkyl group, a ($C_3$-$C_8$ cycloalkyl)($C_1$-$C_6$ alkyl) group (this ($C_3$-$C_8$ cycloalkyl)($C_1$-$C_6$ alkyl) group may have a hydroxycarbonyl ($C_1$-$C_6$ alkyl) group or a ($C_1$-$C_6$ alkoxy)carbonyl($C_1$-$C_6$ alkyl) group as a substituent on the cycloalkyl group), or a ($C_6$-$C_{10}$ aryl)($C_1$-$C_6$ alkyl) group which may have a $C_1$-$C_6$ alkoxy group as a substituent on the aryl ring, or $R^{11}$ and $R^{12}$ combine to form a 5- to 8-membered nitrogen-containing saturated heterocyclic ring which may have a $C_1$-$C_6$ alkyl group as a substituent together with the adjacent nitrogen atom (this heterocyclic ring may have one or more kinds of 1 or 2 hetero atoms selected from the group consisting of nitrogen atom, oxygen atom and sulfur atom in addition to the nitrogen atom adjacent to $R^{11}$ and $R^{12}$), it is more preferred that each of $R^{11}$ and $R^{12}$, the same or different, is a $C_1$-$C_6$ alkyl group, or a ($C_3$-$C_8$ cycloalkyl)($C_1$-$C_6$ alkyl) group (this ($C_3$-$C_8$ cycloalkyl)($C_1$-$C_6$ alkyl) group may have one hydroxycarbonyl($C_1$-$C_6$ alkyl) group or ($C_1$-$C_6$ alkoxy)carbonyl($C_1$-$C_6$ alkyl) group as a substituent on the cycloalkyl group), or $R^{11}$ and $R^{12}$ combine to form morpholino group or piperidino group (the morpholino group or piperidino group may have 1 or 2 of $C_1$-$C_6$ alkyl groups as a substituent) together with the adjacent nitrogen atom, and it is particularly preferred that each of $R^{11}$ and $R^{12}$, the same or different, is ethyl group, cyclopentylmethyl group, ethoxycarbonylmethylcyclohexylmethyl group, or hydroxycarbonylmethylcyclohexylmethyl group, or $R^{11}$ and $R^{12}$ combine to form morpholino group, piperidino group, methylpiperidino group or dimethylmorpholino group together with the adjacent nitrogen atom.

In the general formula (I), examples of the (lower alkyl) thio(lower alkoxy) group as $R^{13}$ include a ($C_1$-$C_6$ alkylthio)($C_1$-$C_6$ alkoxy) group such as methylthiomethoxy group, 2-methylthioethoxy group and 3-methylthiopropoxy group, and 2-methylthioethoxy group is preferred.

In the general formula (I), examples of the (lower alkyl) sulfinyl(lower alkoxy) group as $R^{13}$ include a ($C_1$-$C_6$ alkylsulfinyl)($C_1$-$C_6$ alkoxy) group such as methylsulfinylmethoxy group, 2-methylsulfinylethoxy group and 3-methylsulfinylpropoxy group, and 2-methylsulfinylethoxy group is preferred.

In the general formula (I), examples of the (lower alkyl) sulfonyl(lower alkoxy) group as $R^{13}$ include a ($C_1$-$C_6$ alkylsulfonyl)($C_1$-$C_6$ alkoxy) group such as methylsulfonylmethoxy group, 2-methylsulfonylethoxy group and 3-methylsulfonylpropoxy group, and 2-methylsulfonylethoxy group is preferred.

In the general formula (I), examples of the cyclic amino group which may have a hetero atom as a ring-constituting atom as $R^{13}$ include, for example, pyrrolidinyl group, morpholinyl group, piperidinyl group and the like, and morpholino group or piperidino group is preferred.

In the general formula (I), examples of the substituent of the aryl(lower alkoxy) group which may have a substituent as $R^{13}$ include, for example, a halogen atom, a lower alkyl group, a halo(lower alkyl) group, cyano group and the like. Further, although the substitution position of the substituent is not particularly limited, it preferably substitutes on the aryl ring of the aryl(lower alkoxy) group in the present invention. Number of the substituent is preferably 1 to 3. Examples of the group include a phenyl($C_1$-$C_6$ alkoxy) group which may have a halogen atom, a halo($C_1$-$C_6$ alkyl) group or cyano group as the substituent on the phenyl group, for example, 3,5-bis(trifluoromethyl)benzyl group, 3-cyano-5-trifluoromethylbenzyloxy group, 2,3-difluorobenzyloxy group and the like.

In the general formula (I), it is preferred that $R^{13}$ is a halogen atom, a ($C_1$-$C_6$ alkyl)thio($C_1$-$C_6$ alkoxy) group, a ($C_1$-$C_6$ alkyl)sulfinyl($C_1$-$C_6$ alkoxy) group, a ($C_1$-$C_6$ alkyl)sulfonyl($C_1$-$C_6$ alkoxy) group, a ($C_6$-$C_{10}$ aryl)($C_1$-$C_6$ alkoxy) group (this ($C_6$-$C_{10}$ aryl)($C_1$-$C_6$ alkoxy) group may have a halogen atom, a halo($C_1$-$C_6$ alkyl) group or cyano group as a substituent on the aryl ring), morpholinyl group, or piperidinyl group, and it is particularly preferred that $R^{13}$ is a ($C_1$-$C_6$ alkyl)thio($C_1$-$C_6$ alkoxy) group, a ($C_1$-$C_6$ alkyl)sulfinyl($C_1$-$C_6$ alkoxy) group, or a ($C_1$-$C_6$ alkyl)sulfonyl($C_1$-$C_6$ alkoxy) group.

As for preferred combinations of the substituents in the aforementioned general formula (I), it is preferred that each of $R^1$, $R^2$, $R^3$, $R^4$ and $R^5$, the same or different, is hydrogen atom, a halogen atom, a $C_1$-$C_6$ alkyl group, a halo($C_1$-$C_6$ alkyl) group, a $C_1$-$C_6$ alkoxy group, a halo($C_1$-$C_6$ alkoxy) group, or cyano group, $R^6$ is a $C_1$-$C_6$ alkyl group, a halo($C_1$-$C_6$ alkyl) group, $C_3$-$C_8$ cycloalkyl group, or a ($C_3$-$C_8$ cycloalkyl)($C_1$-$C_6$ alkyl) group, each of $R^7$, $R^8$, $R^9$ and $R^{10}$, the same or different, is hydrogen atom, a halogen atom, a $C_1$-$C_6$ alkyl group, a halo($C_1$-$C_6$ alkyl) group, or a $C_1$-$C_6$ alkoxy group, each of $R^{11}$ and $R^{12}$, the same or different, is a $C_1$-$C_6$ alkyl group, a ($C_3$-$C_8$ cycloalkyl)($C_1$-$C_6$ alkyd group (this ($C_3$-$C_8$ cycloalkyl)($C_1$-$C_6$ alkyd group may have a hydroxycarbonyl($C_1$-$C_6$ alkyd group or a ($C_1$-$C_6$ alkoxy)carbonyl($C_1$-$C_6$ alkyd group as a substituent on the cycloalkyl group), or a ($C_6$-$C_{10}$ aryl)($C_1$-$C_6$ alkyl) group which may have a $C_1$-$C_6$ alkoxy group as a substituent on the aryl ring, or $R^{11}$ and $R^{12}$ combine to form a 5- to 8-membered nitrogen-containing saturated heterocyclic ring which may have a $C_1$-$C_6$ alkyl group as a substituent together with the adjacent nitrogen atom (the heterocyclic ring may have one or more kinds of 1 or 2 hetero atoms selected from the group consisting of nitrogen atom, oxygen atom and sulfur atom in addition to the nitrogen atom adjacent to $R^{11}$ and $R^{12}$), and $R^{13}$ is a halogen atom, a ($C_1$-$C_6$ alkylthio($C_1$-$C_6$ alkoxy) group, a ($C_1$-$C_6$ alkylsulfinyl($C_1$-$C_6$ alkoxy) group, a ($C_1$-$C_6$ alkylsulfonyl($C_1$-$C_6$ alkoxy) group, a ($C_6$-$C_{10}$ aryl)($C_1$-$C_6$ alkoxy) group (this ($C_6$-$C_{10}$ aryl)($C_1$-$C_6$ alkoxy) group may have a halogen atom, a halo($C_1$-$C_6$ alkyl) group, or cyano group as a substituent on the aryl ring), morpholinyl group, or piperidinyl group, it is more preferred that each of $R^1$, $R^2$, $R^3$, $R^4$ and $R^5$, the same or different, is hydrogen atom, a halo($C_1$-$C_6$ alkyd group, or cyano group, $R^6$ is a $C_1$-$C_6$ alkyl group, each of $R^7$, $R^8$, $R^9$ and $R^{10}$, the same or different, is hydrogen atom, a halogen atom, a $C_1$-$C_6$ alkyl group, a halo($C_1$-$C_6$ alkyl) group, or a $C_1$-$C_6$ alkoxy group, each of $R^{11}$ and $R^{12}$, the same or different, is a $C_1$-$C_6$ alkyl group, or a ($C_3$-$C_8$ cycloalkyl)($C_1$-$C_6$ alkyd group (this ($C_3$-$C_8$ cycloalkyl)($C_1$-$C_6$ alkyd group may have one hydroxycarbonyl($C_1$-$C_6$ alkyl) group or ($C_1$-$C_6$ alkoxy)carbonyl($C_1$-$C_6$ alkyd group as a substituent on the cycloalkyl group), or $R^{11}$ and $R^{12}$ combine to form morpholino group or piperidino group together with the adjacent nitrogen atom (the morpholino group or the piperidino group may have 1 or 2 of $C_1$-$C_6$ alkyl groups as a substituent), and $R^{13}$ is a ($C_1$-$C_6$ alkyl)thio($C_1$-$C_6$ alkoxy) group, a ($C_1$-$C_6$ alkylsulfinyl($C_1$-$C_6$ alkoxy) group, or a ($C_1$-$C_6$ alkylsulfonyl($C_1$-$C_6$ alkoxy) group, and it is particularly preferred that $R^1$, $R^3$ and $R^5$ are hydrogen atoms, each of $R^2$ and $R^4$, the same or different, is a halo($C_1$-$C_6$ alkyl) group, or cyano group, $R^6$ is a $C_1$-$C_6$ alkyl group, $R^7$, $R^8$, $R^9$ and $R^{10}$ are as defined in any one of the following i) to iv):

i) at least one of $R^8$, $R^9$ and $R^{10}$ is a halogen atom, preferably bromine atom, and the remainders of $R^7$, $R^8$, $R^9$ and $R^{10}$ are hydrogen atoms, ii) $R^8$ is a $C_1$-$C_6$ alkyl group, and each of $R^7$, $R^9$ and $R^{10}$, the same or different, is hydrogen atom or a halogen atom, iii) at least one of $R^8$ and $R^9$ is a halo($C_1$-$C_6$ alkyl) group, and the remainders of $R^7$, $R^8$, $R^9$ and $R^{10}$ are hydrogen atoms, iv) at least one of $R^8$ and $R^9$ is a $C_1$-$C_6$ alkoxy group, and the remainders of $R^7$, $R^8$, $R^9$ and $R^{10}$ are hydrogen atoms, each of $R^{11}$ and $R^{12}$, the same or different, is a $C_1$-$C_6$ alkyl group, or a ($C_3$-$C_8$ cycloalkyl)($C_1$-$C_6$ alkyl) group (this ($C_3$-$C_8$ cycloalkyl)($C_1$-$C_6$ alkyl) group may have a hydroxycarbonyl($C_1$-$C_6$ alkyl) group or a ($C_1$-$C_6$ alkoxy)carbonyl($C_1$-$C_6$ alkyl) group as a substituent on the cycloalkyl group), or $R^{11}$ and $R^{12}$ combine to form morpholino group or piperidino group (the morpholino group or the piperidino group may have 1 or 2 of $C_1$-$C_6$ alkyl groups as the substituent) together with the adjacent nitrogen atom, and $R^{13}$ is a ($C_1$-$C_6$ alkyl)thio($C_1$-$C_6$ alkoxy) group, a ($C_1$-$C_6$ alkyl)sulfinyl($C_1$-$C_6$ alkoxy) group, or a ($C_1$-$C_6$ alkylsulfonyl ($C_1$-$C_6$ alkoxy) group.

Preferred examples of the compound of the present invention represented by the general formula (I) or a salt thereof, or a solvate thereof include:

N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine (Example 1), N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfinyl)ethoxy]pyrimidin-2-amine (Example 2), N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfonyl)ethoxy]pyrimidin-2-amine (Example 3), N-{1-[3,5-bis(trifluoromethyl)phenyl]ethyl}-N-({2-[(cyclopentylmethyl)(ethyl)amino]-5-methoxyphenyl}methyl)-5-[2-(methylthio)ethoxy]pyrimidin-2-amine (Example 4), N-{1-[3,5-bis(trifluoromethyl)phenyl]ethyl}-N-({2-[(cyclopentylmethyl)(ethyl)amino]-5-methoxyphenyl}methyl)-5-[2-(methylsulfonyl)ethoxy]pyrimidin-2-amine (Example 5), N-{1-[3,5-bis(trifluoromethyl)phenyl]ethyl}-N-({2-[(cyclopentylmethyl)(ethyl)amino]-3,5-difluorophenyl}methyl)-5-[2-(methylthio)ethoxy]pyrimidin-2-amine (Example 6), N-{1-[3,5-bis(trifluoromethyl)phenyl]ethyl}-N-({2-[(cyclopentylmethyl)(ethyl)amino]-3,5-difluorophenyl}methyl)-5-[2-(methylsulfonyl)ethoxy]pyrimidin-2-amine (Example 7), N-{1-[3,5-bis(trifluoromethyl)phenyl]ethyl}-N-({2-[(cyclopentylmethyl)(ethyl)amino]-5-methylphenyl}methyl)-5-[2-(methylthio)ethoxy]pyrimidin-2-amine (Example 8), N-{1-[3,5-bis(trifluoromethyl)phenyl]ethyl}-N-({2-[(cyclopentylmethyl)(ethyl)amino]-5-methylphenyl}methyl)-5-[2-(methylsulfonyl)ethoxy]pyrimidin-2-amine (Example 9), N-{1-[3,5-bis(trifluoromethyl)phenyl]ethyl}-N-({2-[(cyclopentylmethyl)(ethyl)amino]-4-fluorophenyl}methyl)-5-[2-(methylthio)ethoxy]pyrimidin-2-amine (Example 10), N-{1-[3,5-bis(trifluoromethyl)phenyl]ethyl}-N-({2-[(cyclopentylmethyl)(ethyl)amino]-4-fluorophenyl}methyl)-5-[2-(methylsulfonyl)ethoxy]pyrimidin-2-amine (Example 11), N-{1-[3,5-bis(trifluoromethyl)phenyl]ethyl}-N-({2-[(cyclopentylmethyl)(ethyl)amino]-4-methoxyphenyl}methyl)-5-[2-(methylthio)ethoxy]pyrimidin-2-amine (Example 12), N-{1-[3,5-bis(trifluoromethyl)phenyl]ethyl}-N-({2-[(cyclopentylmethyl)(ethyl)amino]-4-methoxyphenyl}methyl)-5-[2-(methylsulfonyl)ethoxy]pyrimidin-2-amine (Example 13), N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylthio)ethoxy]pyrimidin-2-amine (Example 14), N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfinyl)ethoxy]pyrimidin-2-amine (Example 15), N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfonyl)ethoxy]pyrimidin-2-amine (Example 16), N-{1-[3,5-bis(trifluoromethyl)phenyl]ethyl}-N-({2-chloro-6-[(cyclopentylmethyl)(ethyl)amino]-3-methylphenyl}methyl)-5-[2-(methylthio)ethoxy]pyrimidin-2-amine (Example 17), N-{1-[3,5-bis(trifluoromethyl)phenyl]ethyl}-N-({2-chloro-6-[(cyclopentylmethyl)(ethyl)amino]-3-methylphenyl}methyl)-5-[2-(methylsulfonyl)ethoxy]pyrimidin-2-amine (Example 18), N-{1-[3,5-bis(trifluoromethyl)phenyl]ethyl}-N-({2-[(cyclopentylmethyl)(ethyl)amino]phenyl}methyl)-6-[2-(methylthio)ethoxy]pyrimidin-2-amine (Example 19), N-{1-[3,5-bis(trifluoromethyl)phenyl]ethyl}-N-({2-[(cyclopentylmethyl)(ethyl)amino]phenyl}methyl)-5-[2-(methylsulfonyl)ethoxy]pyrimidin-2-amine (Example 20), N-{1-[3,5-bis(trifluoromethyl)phenyl]ethyl}-N-({2-[(cyclopentylmethyl)(ethyl)amino]-4,5-difluorophenyl}methyl)-5-[2-(methylthio)ethoxy]pyrimidin-2-amine (Example 21), N-{1-[3,5-bis(trifluoromethyl)phenyl]ethyl}-N-({2-[(cyclopentylmethyl)(ethyl)amino]-4,5-difluorophenyl}methyl)-5-[2-(methylsulfonyl)ethoxy]pyrimidin-2-amine (Example 22), N-{1-[3,5-bis(trifluoromethyl)phenyl]ethyl}-N-({4-chloro-2-[(cyclopentylmethyl)(ethyl)amino]phenyl}methyl)-5-[2-(methylthio)ethoxy]pyrimidin-2-amine (Example 23), N-{1-[3,5-bis(trifluoromethyl)phenyl]ethyl}-N-({4-chloro-2-[(cyclopentylmethyl)(ethyl)amino]phenyl}methyl)-5-[2-(methylsulfonyl)ethoxy]pyrimidin-2-amine (Example 24), N-{1-[3,5-bis(trifluoromethyl)phenyl]ethyl}-N-({2-[(cyclopentylmethyl)(ethyl)amino]-5-fluorophenyl}methyl)-5-[2-(methylthio)ethoxy]pyrimidin-2-amine (Example 25), N-{1-[3,5-bis(trifluoromethyl)phenyl]ethyl}-N-({2-[(cyclopentylmethyl)(ethyl)amino]-5-fluorophenyl}methyl)-5-[2-(methylsulfonyl)ethoxy]pyrimidin-2-amine (Example 26), N-{1-[3,5-bis(trifluoromethyl)phenyl]ethyl}-N-({4-bromo-2-[(cyclopentylmethyl)(ethyl)amino]phenyl}methyl)-5-[2-(methylthio)ethoxy]pyrimidin-2-amine (Example 27), N-{1-[3,5-bis(trifluoromethyl)phenyl]ethyl}-N-({4-bromo-2-[(cyclopentylmethyl)(ethyl)amino]phenyl}methyl)-5-[2-(methylsulfonyl)ethoxy]pyrimidin-2-amine (Example 28), N-{1-[3,5-bis(trifluoromethyl)phenyl]ethyl}-N-({5-bromo-2-[(cyclopentylmethyl)(ethyl)amino]phenyl}methyl)-5-[2-(methylthio)ethoxy]pyrimidin-2-amine (Example 29), N-{1-[3,5-bis(trifluoromethyl)phenyl]ethyl}-N-({5-bromo-2-[(cyclopentylmethyl)(ethyl)amino]phenyl}methyl)-5-[2-(methylsulfonyl)ethoxy]pyrimidin-2-amine (Example 30), 3-{1-[({2-[(cyclopentylmethyl)(ethyl)amino]-5-trifluoromethylphenyl}methyl){5-[2-(methylthio)ethoxy]pyrimidin-2-yl}amino]ethyl}-5-(trifluoromethyl)benzonitrile (Example 31), 3-{1-[({2-[(cyclopentylmethyl)(ethyl)amino]-5-trifluoromethylphenyl}methyl){5-[2-(methylsulfonyl)ethoxy]pyrimidin-2-yl}amino]ethyl}-5-(trifluoromethyl)benzonitrile (Example 32), N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylthio)ethoxy]pyrimidin-2-amine (Example 33), N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylsulfonyl)ethoxy]pyrimidin-2-amine (Example 34), N-{1-[3,5-bis(trifluoromethyl)phenyl]ethyl}-N-{[2-(piperidino)-5-(trifluoromethyl)phenyl]methyl}-5-[2-(methylthio)ethoxy]pyrimidin-2-amine (Example 35), N-{1-[3,5-bis(trifluoromethyl)phenyl]ethyl}-N-{[2-(piperidino)-5-(trifluoromethyl)phenyl]methyl}-5-[2-(methylsulfonyl)ethoxy]pyrimidin-2-amine (Example 36), N-{1-[3,5-bis(trifluoromethyl)phenyl]ethyl}-N-{[2-(morpholino)-5-(trifluoromethyl)phenyl]methyl}-5-[2-(methylthio)ethoxy]pyrimidin-2-amine (Example 37), N-{1-[3,5-bis(trifluoromethyl)phenyl]ethyl}-N-{[2-(morpholino)-5-(trifluoromethyl)phenyl]methyl}-5-[2-(methylsulfonyl)ethoxy]pyrimidin-2-amine (Example 38), N-{1-[3,5-bis(trifluoromethyl)phenyl]ethyl}-N-{[2-(4-methylpiperidino)-5-(trifluoromethyl)phenyl]methyl}-5-[2-(methylthio)ethoxy]pyrimidin-2-amine (Example 39), N-{1-[3,5-bis(trifluoromethyl)phenyl]ethyl}-N-{[2-(4-methylpiperidino)-5-(trifluoromethyl)phenyl]methyl}-5-[2-(methylsulfonyl)ethoxy]pyrimidin-2-amine (Example 40), N-{1-[3,5-bis(trifluoromethyl)phenyl]ethyl}-N-{[2-(cis-2,6-dimethylmorpholino)-5-(trifluoromethyl)phenyl]methyl}-5-[2-(methylthio)ethoxy]pyrimidin-2-amine (Example 41), N-{1-[3,5-bis(trifluoromethyl)phenyl]ethyl}-N-{[2-(cis-2,6-dimethylmorpholino)-5-(trifluoromethyl)phenyl]methyl}-5-[2-(methylsulfonyl)ethoxy]pyrimidin-2-amine (Example 42), ethyl trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetate (Example 43), trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid (Example 44), trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (Example 45), N-({2-[bis(cyclopropylmethyl)amino]-3,5-difluorophenyl}methyl)-N-{1-[3,5-bis(trifluoromethyl)phenyl]ethyl}-5-[2-(methylthio)ethoxy]pyrimidin-2-amine (Example 46), and N-({2-[bis(cyclopropylmethyl)amino]-3,5-difluorophenyl}methyl)-N-{1-[3,5-bis(trifluoromethyl)phenyl]ethyl}-5-[2-(methylsulfonyl)ethoxy]pyrimidin-2-amine (Example 47), and salts thereof, and solvates thereof.

The general formula (I) represents both individual enantiomers and mixtures thereof. Namely, in the compound of the present invention represented by the general formula (I), the carbon atom to which $R^6$ bonds is an asymmetric carbon, and isomers of any steric configurations based on the asymmetric carbon fall within the scope of the present invention. For example, racemates and one of enantiomers fall within the scope of the present invention. Furthermore, all other producible stereoisomers fall within the scope of the present invention.

Examples of the salt of the compound represented by the general formula (I) include, for example, hydrochloric acid addition salts and the like, and the salts are not particularly limited, so long as they are pharmaceutically acceptable salts. Examples include, for example, acid addition salts of mineral acids such as hydrochlorides, hydrobromides, hydroiodides, sulfates, nitrates and phosphates; acid addition salts of organic acids such as benzoates, methanesulfonates, ethanesulfonates, benzenesulfonates, p-toluenesulfonates, maleates, fumarates, tartrates, citrates and acetates. However, the salt is not limited to these.

Examples of the solvate of the compound represented by the general formula (I) or a salt thereof include, for example, hydrates and the like, but the solvate is not limited to these.

In addition, compounds which are metabolized in the living body and converted into the compounds of the present invention represented by the aforementioned general formula (I), so-called prodrugs, are all also fall within the scope of the compound of the present invention represented by the aforementioned general formula (I). Examples of groups which form the prodrugs of the compounds of the present invention include the groups described in "Progress in Medicine", vol. 5, pp. 2157-2161, 1985, Life Science Medica, and the groups described in "Development of Drugs", vol. 7, Molecular Designs, pp. 163-198, 1990, Hirokawa Shoten.

The compound of the present invention represented by the general formula (I), or a salt thereof, or a solvate thereof can be prepared by various known methods, which methods are not particularly limited. For example, the compound can be prepared according to the following reaction steps, but the method for preparation is not limited thereto. Further, when the following reactions are performed, functional groups other than the reaction sites may be protected beforehand as required, and deprotected in an appropriate stage. Furthermore, each reaction may be performed by an ordinarily used method in each step, and isolation and purification can be performed by a means suitably selected from conventional methods such as crystallization, recrystallization, chromatography and the like, or a combination thereof.

Preparation Methods of Compound Represented by the General Formula (I), or Salt Thereof, or Solvate Thereof I. Preparation Methods of Compound Represented by the General Formula (I), or Salt Thereof, or Solvate Thereof The compound of the present invention represented by the general formula (I) can be prepared by the following method. That is, as shown in the following reaction scheme 1, by reacting an aldehyde derivative represented by the general formula (II) with a pyrimidin-2-amine derivative represented by the general formula (IV) according to a method for reductive amination, or reacting a compound represented by the general formula (III) having a leaving group $W^1$ with a pyrimidin-2-amine derivative represented by the general formula (IV) using a base, an amine compound represented by the general formula (V) can be obtained. By reacting the amine compound represented by the general formula (V) with a compound having a leaving group $W^2$ represented by the general formula (VI) using a base, the compound of the present invention represented by the general formula (I) can be prepared.

This reaction route is represented by reaction formulas as follows.

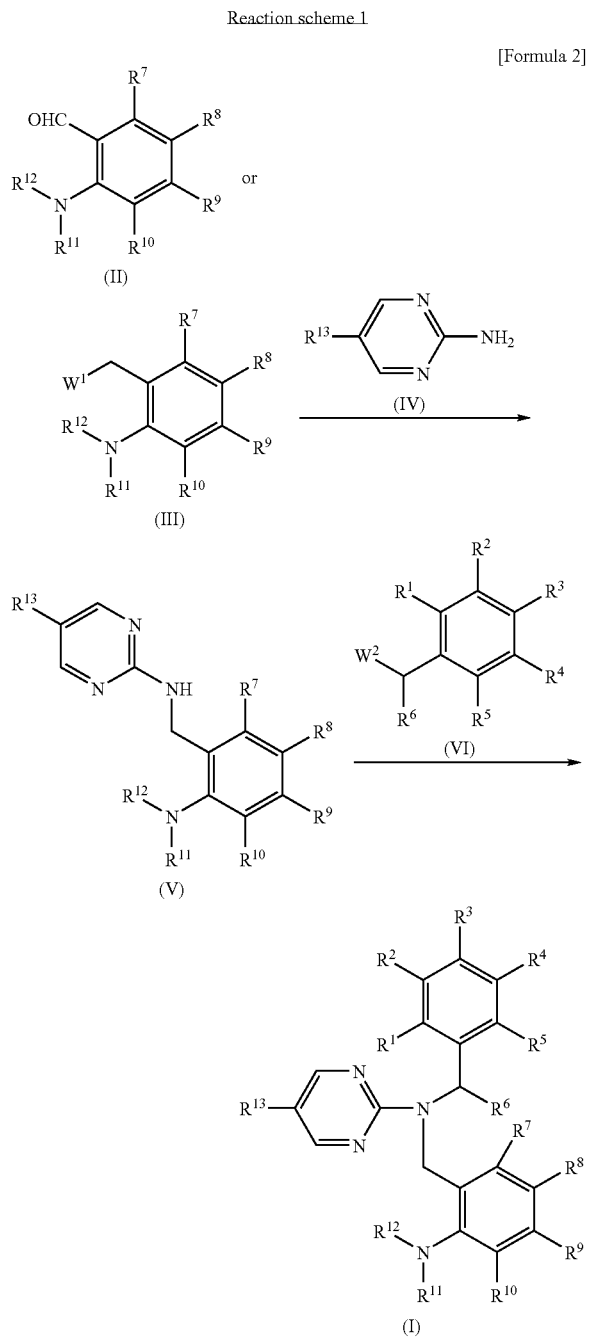

(wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ have the same meanings as those explained for the general formula (I) mentioned above, and $W^1$ and $W^2$ represent a halogen atom, an alkylsulfonyloxy group, a haloalkylsulfonyloxy group or an arylsulfonyloxy group)

The reaction of the aldehyde derivative (II) and the pyrimidin-2-amine derivative (IV) can be performed by using a reducing reagent in a solvent in the presence or absence of an acid. During the reaction, dehydration may be performed by using a Dean-Stark apparatus or the like. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, and the like may be used alone or in combination. As the acid, although not particularly limited, for example, proton acids such as acetic acid, trifluoroacetic acid, propionic acid and benzoic acid, and Lewis acids such as titanium tetrachloride, boron trifluoride and stannic chloride can be used. The reducing reagent is not particularly limited, and catalytic reduction using a borohydride reagent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride reagent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide/carbon powder, Raney nickel, platinum dioxide, platinum black and the like can be used.

The reaction of the compound (III) having a leaving group $W^1$ and the pyrimidin-2-amine derivative (IV) can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The reaction of the amine compound (V) obtained by the aforementioned method and the compound (VI) having a leaving group $W^2$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

Further, besides the aforementioned method, the compound of the present invention represented by the general formula (I) can also be prepared by the following method. That is, as shown in the following reaction scheme 2, by reacting the pyrimidin-2-amine derivative represented by the general formula (IV) with a compound having a leaving group $W^2$ represented by the general formula (VI) using a base, or reacting the pyrimidin-2-amine derivative represented by the general formula (IV) with a ketone derivative represented by the general formula (VII) according to a method for reductive amination, an amine compound represented by the general formula (VIII) can be obtained. By reacting the amine compound represented by the general formula (VIII) with the compound having a leaving group $W^1$ represented by the general formula (III) using a base, the compound of the present invention represented by the general formula (I) can be prepared.

This reaction route is represented by reaction formulas as follows.

Reaction scheme 2

[Formula 3]

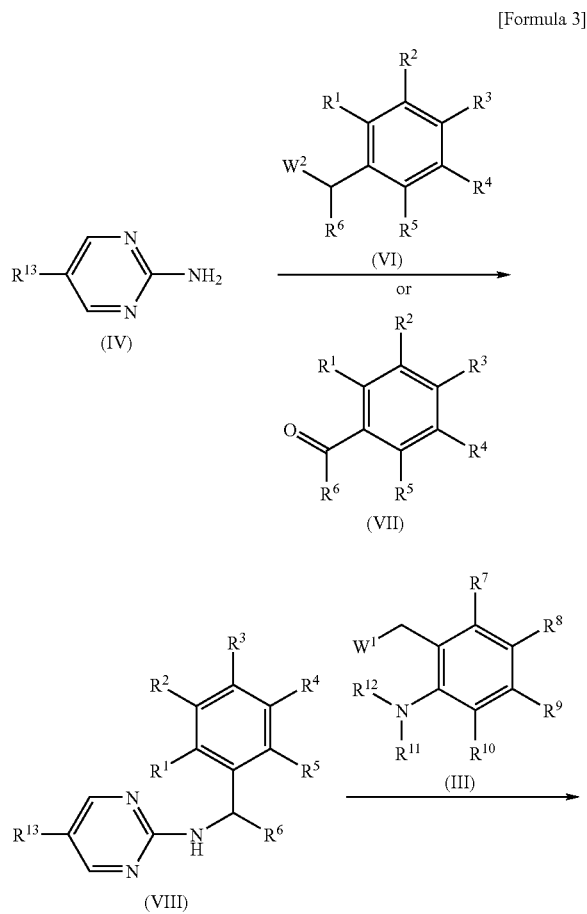

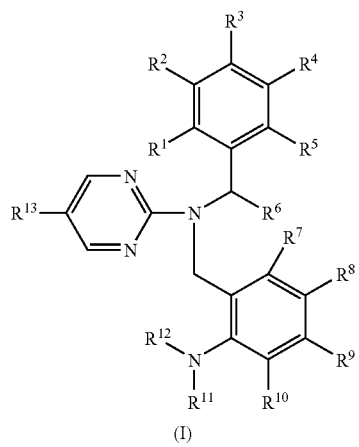

(wherein, $R^1$, $R^2$, $R^3$, $R^4$, $R^5$, $R^6$, $R^7$, $R^8$, $R^9$, $R^{10}$, $R^{11}$, $R^{12}$ and $R^{13}$ have the same meanings as those explained for the general formula (I) mentioned above, and $W^1$ and $W^2$ represent a halogen atom, an alkylsulfonyloxy group, a haloalkylsulfonyloxy group or an arylsulfonyloxy group)

The reaction of the pyrimidin-2-amine derivative (IV) and the compound (VI) having a leaving group $W^2$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The reaction of the pyrimidin-2-amine derivative (IV) and the ketone derivative (VII) can be performed by using a reducing reagent in a solvent in the presence or absence of an acid. During the reaction, dehydration may be performed by using a Dean-Stark apparatus or the like. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol and the like may be used alone or in combination. As the acid, although not particularly limited, for example, proton acids such as acetic acid, trifluoroacetic acid, propionic acid and benzoic acid, and Lewis acids such as titanium tetrachloride, boron trifluoride and stannic chloride can be used. The reducing reagent is not particularly limited, and catalytic reduction using a borohydride type reagent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride reagent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide/carbon powder, Raney nickel, platinum dioxide, platinum black and the like can be used.

The reaction of the compound (III) having a leaving group $W^1$ and the amine compound (VIII) can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

Examples of the preparation methods of the aldehyde derivative (II), the compound (III) having a leaving group $W^1$, the pyrimidin-2-amine derivative (IV), and the compound (VI) having a leaving group $W^2$ used in the above reactions are mentioned below.

1 Preparation Methods of the Aldehyde Derivative Represented by the General Formula (II) and the Compound Represented by the General Formula (III) Having a Leaving Group $W^1$ As the aforementioned aldehyde derivative (II) and the compound (III) having a leaving group $W^1$, available compounds may be used per se, or they can be suitably prepared by a known method. For example, they can be prepared by the following methods. However, the preparation methods are not limited to the following examples.

As shown in the following reaction scheme 3, by reacting an o-fluoroaldehyde derivative represented by the general formula (IX) with an amine represented by the general formula (X), an aldehyde derivative represented by the general formula (II) can be obtained.

This reaction route is represented by reaction formulas as follows.

Reaction scheme 3

[Formula 4]

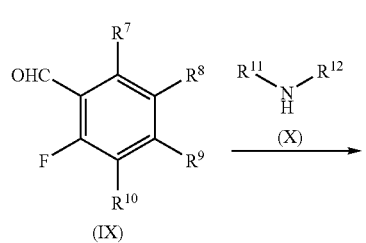

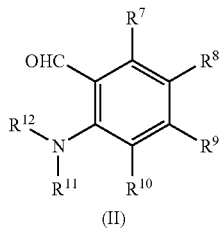

(wherein $R^7$, $R^8$, $R^9$, $R^{10}$, $R^{11}$ and $R^{12}$ have the same meanings as those explained for the general formula (I) mentioned above)

The reaction of the o-fluoroaldehyde derivative (IX) and the amine (X) can be performed in a solvent in the presence or absence of a base. As the solvent, although not particularly limited, for example, tetrahydrofuran, toluene, dioxane, N,N-dimethylformamide, N-methylpyrrolidone, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, 1,4-diazabicyclo[2.2.2]octane (DABCO), lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. Although the reaction conditions should be changed depending on the starting material used, the target compound can be obtained by performing the reaction generally at 0 to 180° C., preferably 50 to 160° C., for 5 minutes to 2 weeks, preferably 3 hours to 1 week.

The aldehyde derivative (II) and the compound (III) having a leaving group $W^1$ can also be prepared by the following method. That is, as shown in the following reaction scheme 4, by protecting hydroxy group of an alcohol derivative represented by the general formula (XI) with a protective group $R^{14}$, an ether compound represented by the general formula (XII) can be obtained. The protective group $R^{14}$ in the general formula (XII) is a protective group generally used as a protective group of hydroxy group, and although not particularly limited, methoxymethyl group, benzyloxymethyl group, 4-methoxybenzyloxymethyl group, methoxyethoxymethyl group, ethoxyethyl group, t-butyldimethylsilyl group, triethylsilyl group, t-butyldiphenylsilyl group, triisopropylsilyl group, triphenylsilyl group, 4-methoxybenzyl group, benzyl group, 3,4-dimethoxybenzyl group, 2,4,6-trimethylbenzyl group, trityl group, and the like are preferred. By reacting the ether compound represented by the general formula (XII) and an amine represented by the general formula (XIII), an amine derivative represented by the general formula (XIV) can be obtained. By reacting the obtained amine derivative represented by the general formula (XIV) with a compound having a leaving group $W^4$ represented by the general formula (XV), or using a reductive amination method in which an imine compound obtained by a reaction of the amine derivative and an aldehyde derivative represented by the general formula (XVI) is subjected to a reduction reaction, an amine derivative represented by the general formula (XVII) can be obtained. By removing the protective group $R^{14}$ of the obtained amine derivative represented by the general formula (XVII) to obtain an alcohol compound represented by the general formula (XVIII), and then oxidizing the produced hydroxy group, the aldehyde derivative represented by the general formula (II) can be obtained. Further, by converting the alcohol moiety of the alcohol compound represented by the general formula (XVIII) into the leaving group $W^1$, the compound represented by the general formula (III) having a leaving group $W^1$ can be obtained.

This reaction route is represented by reaction formulas as follows.

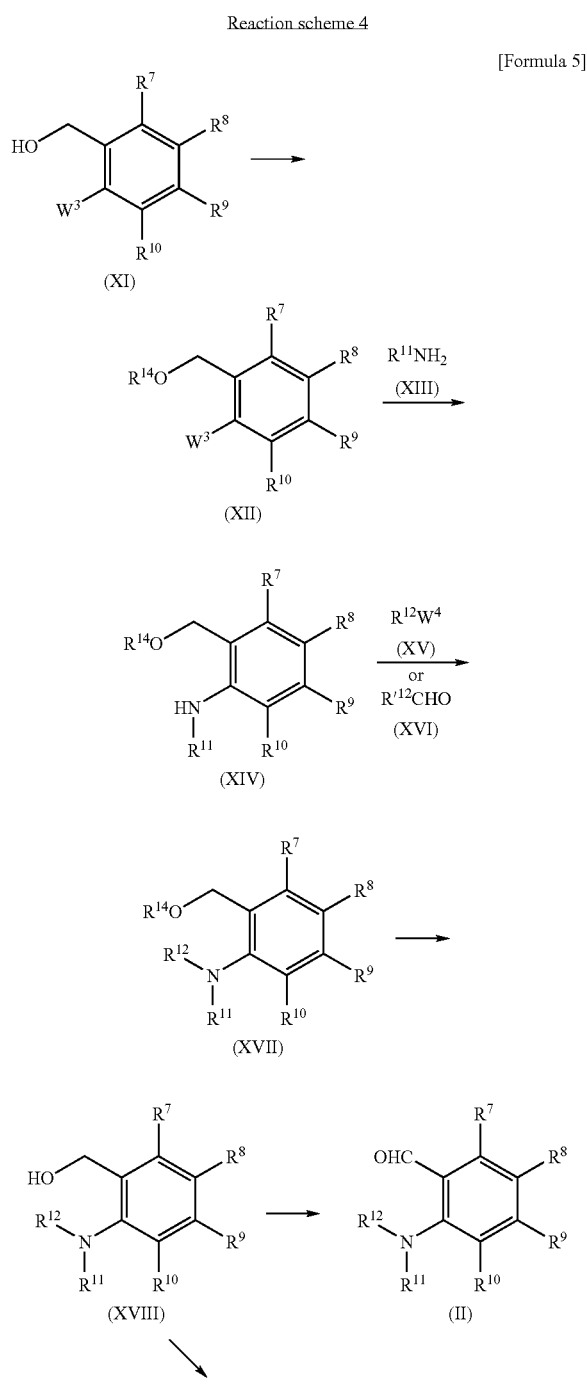

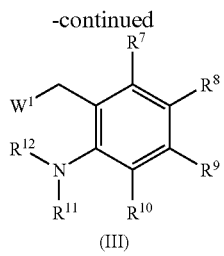

(wherein, $R^7$, $R^8$, $R^9$, $R^{10}$, $R^{11}$ and $R^{12}$ have the same meanings as those explained for the general formula (I) mentioned above, $W^3$ and $W^4$ represent a halogen atom, an alkylsulfonyloxy group, a haloalkylsulfonyloxy group or an arylsulfonyloxy group, $R^{14}$ represents a protective group, and $R'^{12}$ represents a lower alkyl group, a (lower cycloalkyl)(lower alkyl) group or a lower cycloalkyl group, of which number of carbon atom to be bound to the nitrogen atom is smaller by 1 than that of $R^{12}$)

The method for introducing the protective group $R^{14}$ into the alcohol derivative (XI), although not particularly limited, can be performed by referring to a method generally used for introduction of the protective group (Protective Groups in Organic Synthesis Third Edition, John Wiley & Sons, Inc.).

For the reaction of the obtained ether compound (XII) and the amine (XIII), a reaction method of an aryl halide and an amine performed in the presence or absence of a base and in the presence or absence of a metal catalyst can be applied. During the reaction, microwave irradiation may be performed during the reaction. As the solvent, although not particularly limited, for example, tetrahydrofuran, toluene, dioxane, N,N-dimethylformamide, N-methylpyrrolidone, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. As the metal catalyst, for example, tris(dibenzylideneacetone)dipalladium(0), tris(dibenzylideneacetone)(chloroform)dipalladium(0), [1,1'-bis(diphenylphosphino)ferrocene]dichloropalladium(II), tetrakis(triphenylphosphine)palladium and the like may be used alone, and a ligand such as (2-biphenyl)di-t butylphosphine and (2-biphenyl)dicyclohexylphosphine may also be used in combination. Although the reaction conditions should be changed depending on the starting material used, the target compound can be obtained by performing the reaction generally at 0 to 180° C., preferably 80 to 160° C., for 5 minutes to 72 hours, preferably 10 minutes to 24 hours. When microwave irradiation is performed, the target compound can be obtained by starting the reaction at 0 to 180° C., preferably at room temperature, under microwave irradiation, elevating the temperature to 80 to 150° C., and performing the reaction for 1 minute to 20 hours, preferably 1 minute to 3 hours, including the temperature elevation time.

The reaction of the amine derivative (XIV) obtained in the above reaction and the compound (XV) having a leaving group $W^4$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination. As the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The reaction of the amine derivative (XIV) and the aldehyde derivative (XVI) can be performed by using a reducing reagent in a solvent in the presence or absence of an acid. During the reaction, dehydration may be performed by using a Dean-Stark apparatus or the like. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, and the like may be used alone or in combination. As the acid, although not particularly limited, for example, proton acids such as acetic acid, trifluoroacetic acid, propionic acid and benzoic acid, and Lewis acids such as titanium tetrachloride, boron trifluoride and stannic chloride can be used. The reducing reagent is not particularly limited, and catalytic reduction using a borohydride reagent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride reagent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide/carbon powder, Raney nickel, platinum dioxide, platinum black and the like can be used.

The method for removing the protective group $R^{14}$ of the amine derivative (XVII) obtained by the aforementioned method, although not particularly limited, can be performed by referring to a method generally used for removal of the protective group (Protective Groups in Organic Synthesis Third Edition, John Wiley & Sons, Inc.).

For the oxidation reaction of the alcohol compound (XVIII) for conversion into the aldehyde derivative (II), an ordinary method for oxidizing hydroxy group into aldehyde can be applied. For example, oxidation conditions of Swern oxidation, Moffatt oxidation, Dess-Martin oxidation and the like, and pyridinium chlorochromate (PCC), pyridinium dichromate (PDC), manganese dioxide, tetrapropylammonium perruthenate (TPAP) and the like can be used. Although the solvent is not particularly limited, for example, tetrahydrofuran, dichloromethane, chloroform, 1,2-dichloroethane, N,N-dimethylformamide and the like can be used alone or in combination.

The reaction for synthesizing the compound (III) having a leaving group $W^1$ from the alcohol compound (XVIII) can be selected depending on the type of the leaving group as follows.

When $W^1$ of the compound (III) having a leaving group $W^1$ is an alkylsulfonyloxy group, a haloalkylsulfonyloxy group or an arylsulfonyloxy group, the compound (III) can be obtained by a reaction of the alcohol compound (XVIII) and an alkylsulfonic acid esterifying agent, a haloalkylsulfonic acid esterifying agent or an arylsulfonic acid esterifying agent in a solvent in the presence or absence of a base. As the alkylsulfonic acid esterifying agent, although not particularly limited, for example, methanesulfonyl chloride, methanesulfonic acid anhydride, ethanesulfonyl chloride, benzylsulfonyl chloride, alkylsulfonyl chloride and the like can be used. As the haloalkylsulfonic acid esterifying agent, although not particularly limited, for example, trifluoromethanesulfonyl chloride, trifluoromethanesulfonic acid anhydride, chloromethanesulfonyl chloride and the like can be used. As the arylsulfonic acid esterifying agent, although not particularly limited, for example, benzenesulfonyl chloride, p-toluenesulfonyl chloride, o-nitrobenzenesulfonyl chloride, p-nitrobenzenesulfonyl chloride and the like can be used. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, N,N-dimethylformamide and the like may be used alone or in combination. As the base, although not particularly limited, for example, organic bases such as pyridine, 4-dimethylaminopyridine (DMAP), collidine, lutidine, 1,8-diazabicyclo[5.4.0]undec-7-ene (DBU), 1,5-diazabicyclo[4.3.0]non-5-ene (DBN), DABCO, triethylamine, 2,6-di-t-butylpyridine, N,N-diisopropylethylamine, N,N-diisopropylpentylamine and trimethylamine, alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, hydrogencarbonates such as sodium hydrogencarbonate and potassium hydrogencarbonate and the like can be used.

When $W^1$ of the compound (II) having a leaving group $W^1$ is a halogen atom, the compound (II) can be obtained by a reaction of the alcohol compound (XVIII) and a halogenating agent in a solvent or without solvent in the presence or absence of a base. Examples of the halogenating agent include, although not particularly limited, chlorinating agents, brominating agents or iodinating agents such as phosphorus oxychloride, phosphorus pentachloride, triphenylphosphine dichloride, triphenylphosphine dibromide, triphenylphosphite dichloride, triphenylphosphite dibromide, phosphorus tribromide, thionyl chloride, triphenylphosphine and carbon tetrachloride, triphenylphosphine and carbon tetrabromide, triphenylphosphine, iodine and imidazole, triphenylphosphine and N-iodosuccinimide (NIS), and methanesulfonyl chloride and DMAP. As the solvent, although not particularly limited, for example, 1,2-dichloroethane, chloroform, dichloromethane, diethyl ether, ethyl acetate, isopropyl acetate, toluene, benzene, tetrahydrofuran, dioxane, acetonitrile, propionitrile and the like may be used alone or in combination. As the base, although not particularly limited, for example, organic bases such as pyridine, DMAP, collidine, lutidine, DBU, DBN, DABCO, triethylamine, 2,6-di-t-butylpyridine, N,N-diisopropylethylamine, N,N-diisopropylpentylamine, and trimethylamine, alkali metal carbonates such as lithium carbonate, sodium carbonate, potassium carbonate and cesium carbonate, hydrogencarbonates such as sodium hydrogencarbonate and potassium hydrogencarbonate, and the like can be used.

2 Preparation Methods of pyrimidin-2-amine Derivative (IV)

As the aforementioned pyrimidin-2-amine derivative (IV), an available compound may be used per se, or it can be suitably prepared by a known method. For example, the pyrimidin-2-amine derivative (IV) can be prepared by the following methods depending on the type of $R^{13}$ substituting at the 5-position of the pyrimidin-2-amine derivative (IV). However, the preparation method is not limited to the following examples.

2-1 Preparation Method of pyrimidin-2-amine Derivative (IV') wherein $R^{13}$ is a di(lower alkyl)amino Group or a Cyclic Amino Group which May have a Hetero Atom as a Ring-Constituting Atom As shown in the following reaction scheme 5, by a reaction of 5-bromopyrimidine-2-amine (XIX) and a di(lower alkyl) amine, or a cyclic amine which may have a hetero atom as a ring-constituting atom represented by the general formula (XX), the pyrimidin-2-amine derivative represented by the general formula (IV') wherein $R^{13}$ is a di(lower alkyl)amino group or a cyclic amino group which may have a hetero atom as a ring-constituting atom can be obtained.

This reaction route is represented by a reaction formula as follows.

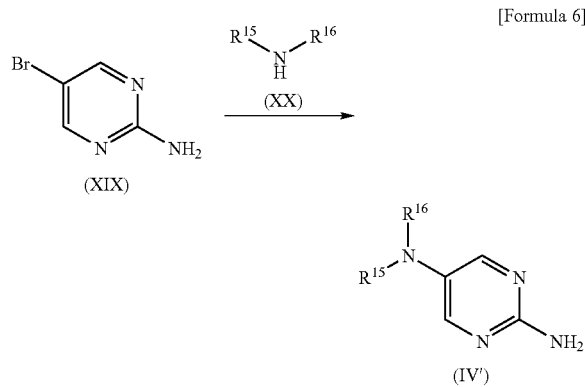

Reaction scheme 5

[Formula 6]

(wherein each of $R^{15}$ and $R^{16}$, the same or different, is a lower alkyl group, or $R^{15}$ and $R^{16}$ combine to form a cyclic amine which may have a hetero atom as a ring-constituting atom together with the adjacent nitrogen atom)

For the reaction of 5-bromopyrimidine-2-amine (XIX) and the di(lower alkyl)amine or cyclic amine which may have a hetero atom as a ring-constituting atom represented by the general formula (XX), a method for a reaction of an aryl halide and an amine performed in a solvent or without solvent in the presence or absence of a base and in the presence of a metal catalyst can be applied. This reaction can be performed by, for example, reacting both compounds in a solvent in the presence of a metal catalyst. During the reaction, microwave irradiation may be performed. As the metal catalyst, for example, a palladium complex such as tris(dibenzylideneacetone)dipalladium(0), tris(dibenzylideneacetone)(chloroform)dipalladium(0), [1,1'-bis(diphenylphosphino)ferrocene]dichloropalladium(II) and tetrakis(triphenylphosphine)palladium, or a monovalent copper reagent such as cuprous iodide, cuprous bromide and cuprous cyanide may be used alone, and a ligand such as (2-biphenyl)di-t-butylphosphine, (2-biphenyl)dicyclohexylphosphine, tetramethylethylenediamine, N,N'-dimethylethylenediamine, glycine, N,N-dimethylglycine and N-methylglycine may also be used in combination. As the solvent, although not particularly limited, for example, tetrahydrofuran, toluene, dioxane, N,N-dimethylformamide, N-methylpyrrolidone, dimethyl sulfoxide, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. As for the reaction conditions, the target compound can be obtained by performing the reaction at 0 to 180° C., preferably 80 to 150° C., for 1 minute to 5 days, preferably 1 hour to 3 days.

2-2 Preparation method-1 of 2-aminopyrimidine Derivative (IV'') wherein $R^{13}$ is a Lower Alkoxy Group, a (lower alkyl) thio(lower alkoxy) Group, a (lower alkoxy)(lower alkoxy) Group or a di(lower alkyl)amino(lower alkoxy) Group As shown in the following reaction scheme 6, by a reaction of 5-bromo-2-chloropyrimidine (XXI) and an amine substituted with a removable functional group $R^{17}$ represented by the general formula (XXII), a pyrimidin-2-amine derivative represented by the general formula (XXIII) can be obtained. By reacting this obtained pyrimidin-2-amine derivative represented by the general formula (XXIII) and a lower alkyl alcohol, a (lower alkyl)thio(lower alkyl) alcohol, a (lower alkoxy)(lower alkyl) alcohol or a di(lower alkyl)amino(lower alkyl) alcohol represented by the general formula (XXIV) to obtain an ether compound represented by the general formula (XXV), and removing $R^{17}$ of the ether compound represented by the general formula (XXV), a pyrimidin-2-amine derivative represented by the general formula (IV') wherein $R^{13}$ is a lower alkoxy group, a (lower alkyl)thio(lower alkoxy) group, a (lower alkoxy)(lower alkoxy) group or a di(lower alkyl) amino(lower alkoxy) group can be obtained.

This reaction route is represented by reaction formulas as follows.

Reaction scheme 6

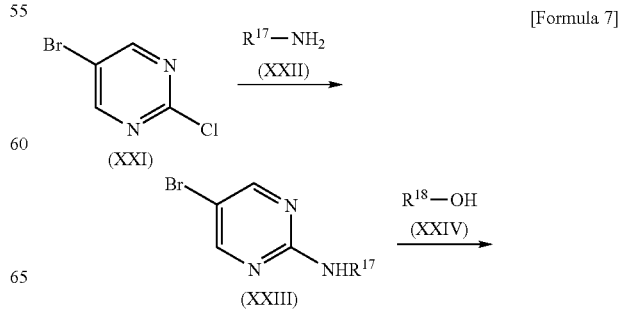

[Formula 7]

-continued

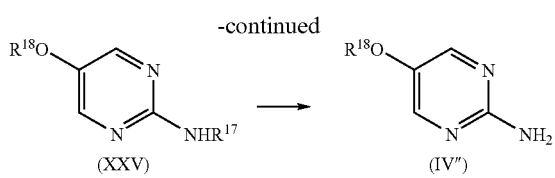

(wherein $R^{17}$ represents a protective group, and $R^{18}$ represents a lower alkyl group, a (lower alkyl)thio(lower alkyl) group, a (lower alkoxy)(lower alkyl) group or a di(lower alkyl)amino(lower alkyl) group)

For the reaction of 5-bromo-2-chloropyrimidine (XXI) and the amine (XXII), the target compound can be obtained by performing the reaction in a solvent or without solvent. During the reaction, microwave irradiation may be performed. As the solvent, although not particularly limited, for example, tetrahydrofuran, toluene, dioxane, N,N-dimethylformamide, N-methylpyrrolidone, dimethyl sulfoxide, water and the like may be used alone or in combination. As for the reaction conditions, although they should be changed depending on the type of the used amine represented by the general formula (XXII), the target compound can be obtained by performing the reaction generally at −20 to 180° C., preferably 0 to 150° C., for 1 minute to 24 hours, preferably 5 minutes to 10 hours.

For the reaction of the obtained pyrimidin-2-amine derivative (XXIII) and the alcohol (XXIV), a method for a reaction of an aryl halide and an alcohol performed in a solvent or without solvent in the presence or absence of a base and in the presence of a metal catalyst can be applied. In this reaction, for example, by reacting both compounds in a solvent in the presence of a metal catalyst, the target compound, the ether compound (XXV), can be obtained. During the reaction, microwave irradiation may be performed. As the metal catalyst, for example, a palladium complex such as tris(dibenzylideneacetone)dipalladium(0), tris(dibenzylideneacetone)(chloroform)dipalladium(0), [1,1′-bis(diphenylphosphino)ferrocene]dichloropalladium(II) and tetrakis(triphenylphosphine)palladium, or a monovalent copper reagent such as cuprous iodide, cuprous bromide and cuprous cyanide may be used alone, and a ligand such as (2-biphenyl)di-t-butylphosphine, (2-biphenyl)dicyclohexylphosphine, tetramethylethylenediamine, N,N′-dimethylethylenediamine, glycine, N,N-dimethylglycine and N-methylglycine may also be used in combination. As the solvent, although not particularly limited, for example, tetrahydrofuran, toluene, dioxane, N,N-dimethylformamide, N-methylpyrrolidone, dimethyl sulfoxide, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. As for the reaction conditions, the target compound can be obtained by performing the reaction at 0 to 180° C., preferably 80 to 150° C., for 1 minute to 5 days, preferably 1 hour to 3 days.

The method for removing the protective group $R^{17}$ of the ether compound (XXV) obtained by the aforementioned method, although not particularly limited, can be performed by referring to a method generally used for removal of the protective group (Protective Groups in Organic Synthesis Third Edition, John Wiley & Sons, Inc.).

2-3 Preparation method-2 of 2-aminopyrimidine Compound (IV″) Wherein $R^{13}$ is a Lower Alkoxy Group, a (lower alkyl) thio(lower alkoxy) Group, a (lower alkoxy)(lower alkoxy) Group or a di(lower alkyl)amino(lower alkoxy) Group As shown in the following reaction scheme 7, by subjecting an acetal derivative represented by the general formula (XXVI) to the Vilsmeier reaction, an aminoacrolein derivative represented by the general formula (XXVII) can be obtained. Each of $R^{19}$ and $R^{20}$ in the general formula (XXVI) is a lower alkyl group, or a protective group generally used as a protective group of hydroxy group, and although not particularly limited, each of them, the same or different, is preferably methyl group, ethyl group, propyl group, benzyl group, p-methoxybenzyl group, 2,4,6-trimethylbenzyl group, or the like. $R^{21}$ and $R^{22}$ in the general formula (XXVII) are the same or different, and represent a lower alkyl group or an arylalkyl group which may have a substituent, or may combine to form a nitrogen-containing saturated heterocyclic ring together with the adjacent nitrogen atom, each of them, although not particularly limited, the same or different, is preferably methyl group, ethyl group, propyl group, benzyl group, p-methoxybenzyl group, 2,4,6-trimethylbenzyl group or the like, and as the nitrogen-containing saturated heterocyclic ring formed by combined $R^{21}$ and $R^{22}$ together with the adjacent nitrogen atom, piperidine, pyrrolidine, morpholine and the like are preferred. By a reaction of this obtained aminoacrolein derivative represented by the general formula (XXVII) and a guanidine salt (XXVIII), the aminopyrimidine derivative represented by the general formula (XXIX) can be obtained. HA in the general formula (XXVIII) represents an acid which forms a salt with guanidine. The acid which forms a guanidine salt used here, although not particularly limited, is preferably hydrochloric acid, sulfuric acid, nitric acid, carbonic acid, acetic acid, hydrobromic acid, hydroiodic acid or the like. By protecting the amino group of the aminopyrimidine derivative (XXIX) with a protective group $R^{23}$, the compound represented by the general formula (XXX) can be obtained. The protective group $R^{23}$ in the general formula (XXX) is a protective group generally used as a protective group of amino group, and it is, although not particularly limited, preferably formyl group, acetyl group, propionyl group, butyryl group, hexanoyl group, trifluoroacetyl group, benzoyl group, cyclohexylcarbonyl group, benzyloxycarbonyl group, 2,2,2-trichloroethylcarbonyl group, t-butoxycarbonyl group, 4-methoxybenzyl group, benzyl group, 3,4-dimethoxybenzyl group, 2,4,6-trimethylbenzyl group, trifluoromethanesulfonyl group or the like. By removing $R^{19}$ of the obtained compound represented by the general formula (XXX), the hydroxypyrimidine derivative represented by the general formula (XXXI) can be obtained. By obtaining an ether compound represented by the general formula (XXXIII) by the Mitsunobu reaction of the hydroxypyrimidine derivative (XXXI) and a lower alkyl alcohol, a (lower alkyl)thio(lower alkyl) alcohol, a (lower alkoxy)(lower alkyl) alcohol, or a di(lower alkyl)amino(lower alkyl) alcohol represented by the general formula (XXIV), or a reaction with a compound (XXXII) having a leaving group $W^5$, and removing $R^{23}$ of the ether compound represented by the general formula (XXXIII), the 2-aminopyrimidine derivative represented by the general formula (IV′) wherein $R^{13}$ is a lower alkoxy group, a (lower alkyl)thio(lower alkoxy) group, a (lower alkoxy)(lower alkoxy) group or a di(lower alkyl)amino(lower alkoxy) group can be obtained.

This reaction route is represented by reaction formulas as follows.

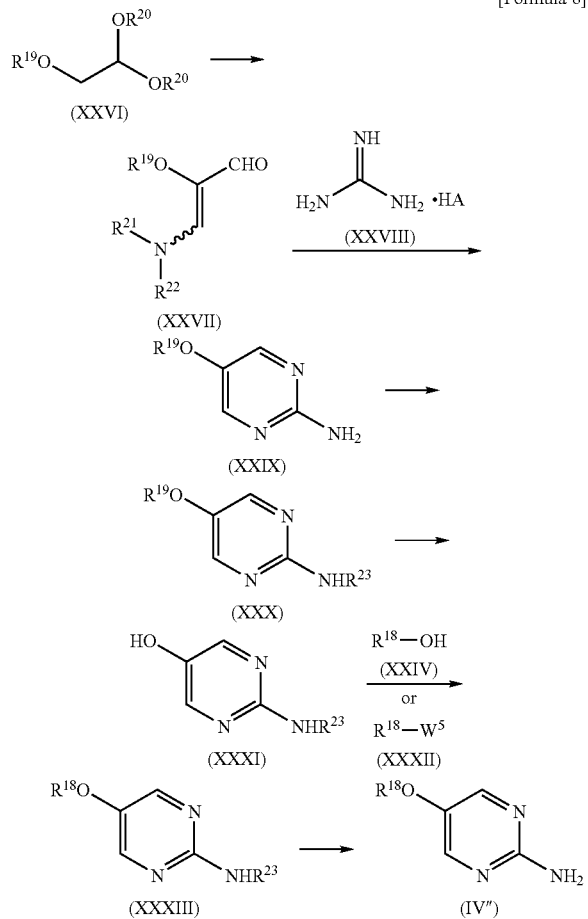

Reaction scheme 7

[Formula 8]

(wherein $R^{18}$ represents a lower alkyl group, a (lower alkyl)thio(lower alkyl) group, a (lower alkoxy)(lower alkyl) group or a di(lower alkyl)amino(lower alkyl) group, $R^{19}$ and $R^{20}$ represent a lower alkyl group or a protective group, $R^{21}$ and $R^{22}$ are the same or different, and represent a lower alkyl group or an aryl(lower alkyl) group which may have a substituent, or may combine to form a nitrogen-containing saturated heterocyclic ring together with the adjacent nitrogen atom, $R^{23}$ represents a protective group, $W^5$ represents a halogen atom, an alkylsulfonyloxy group, a haloalkylsulfonyloxy group or an arylsulfonyloxy group, and HA represents an acid which forms a salt with guanidine)

As for the Vilsmeier reaction of the acetal derivative (XXVI), the target compound can be obtained by performing the reaction with a Vilsmeier reagent in a solvent or without solvent. Although the Vilsmeier reagent is not particularly limited, as the formamide used, for example, N,N-dimethylformamide, N,N-diethylformamide, N-formylpiperidine, N-formylpyrrolidine, N-formylmorpholine and the like can be used, and as the phosphorus reagent used, for example, phosphorus oxyhalides such as phosphorus oxychloride and phosphorus oxybromide, and phosphorus halides such as phosphorus pentachloride and phosphorus pentabromide can be used. As the solvent, although not particularly limited, for example, tetrahydrofuran, toluene, benzene, dioxane, chloroform, dichloromethane, 1,2-dichloroethane and the like may be used alone or in combination. As for the reaction conditions, although they should be changed depending on the acetal derivative represented by the general formula (XXVI) used, the target compound can be obtained by performing the reaction generally at −20 to 150° C., preferably 0 to 100° C., for 5 minutes to 1 week, preferably 30 minutes to 100 hours.

By a reaction of the obtained aminoacrolein derivative (XXVII) and the guanidine salt (XXVIII) in a solvent in the presence of a base, the target compound, the aminopyrimidine derivative (XXIX), can be obtained. As the base, although not particularly limited, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium methoxide, potassium methoxide, sodium ethoxide, potassium ethoxide, sodium t-butoxide, potassium t-butoxide, n-butyllithium, s-butyllithium, t-butyllithium and the like can be used. As the solvent, although not particularly limited, methanol, ethanol, isopropanol, N,N-dimethylformamide, N-methylpyrrolidone, dimethyl sulfoxide, tetrahydrofuran, toluene, benzene, dioxane, chloroform, dichloromethane, 1,2-dichloroethane, acetonitrile, nitromethane, water and the like may be used alone or in combination. As for the reaction conditions, although they should be changed depending on the aminoacrolein derivative (XXVII) used, the target compound can be obtained by performing the reaction generally at −20 to 150° C., preferably 0 to 100° C., for 30 minutes to 1 week, preferably 30 minutes to 5 days.

The method for introducing the protective group $R^{23}$ into the amino group of the aminopyrimidine derivative (XXIX) can be performed by referring to a method generally used for introduction of the protective group (Protective Groups in Organic Synthesis Third Edition, John Wiley & Sons, Inc.).

Removal of $R^{19}$ of the compound represented by the general formula (XXX), although not particularly limited, can be performed in a solvent by using a Lewis acid or a proton acid. As the Lewis acid, although not particularly limited, boron tribromide, boron trichloride, aluminum chloride, trimethylsilyl iodide, trimethylsilyl trifluoromethanesulfonate, ethyl aluminum dichloride, diethyl aluminum chloride and the like can be used. As the proton acid, although not particularly limited, hydrobromic acid, hydroiodic acid and the like can be used. As the solvent, although not particularly limited, toluene, benzene, chloroform, dichloromethane, 1,2-dichloroethane, chlorobenzene, nitrobenzene, acetonitrile, nitromethane, acetic acid and the like may be used alone or in combination. As for the reaction conditions, although they should be changed depending on the compound represented by the general formula (XXX) used, the target compound can be obtained by performing the reaction generally at −20 to 150° C., preferably 0 to 120° C., for 10 minutes to 3 days, preferably 10 minutes to 30 hours. When $R^{19}$ is an arylmethyl group such as benzyl group, p-methoxybenzyl group, and 2,4,6-trimethylbenzyl group, besides the aforementioned methods, the deprotection can be attained by hydrogenation. As the hydrogen source for hydrogenation, although not particularly limited, hydrogen, formic acid, ammonium formate, cyclohexadiene and the like can be used. As the hydrogenation catalyst, although not particularly limited, palladium/carbon, palladium black, platinum black, platinum dioxide, Raney nickel, palladium hydroxide/carbon powder and the like can be used. As the solvent, although not particularly limited, methanol, ethanol, isopropanol, ethyl acetate, isopropyl acetate, N,N-dimethylformamide, tetrahydrofuran, dioxane, acetonitrile, acetic acid, water and the like may be used alone or in combination. As for the reaction conditions, although they should be changed depending on the compound represented by the general formula (XXX) used, the target compound can be obtained by performing the reaction generally at 0 to 150° C., preferably 0 to 100° C., for 30 minutes to 3 days, preferably 30 minutes to 50 hours.

By the Mitsunobu reaction of the hydroxypyrimidine derivative (XXXI) with the alcohol (XXIV), or a reaction of the hydroxypyrimidine derivative (XXXI) with the compound (XXXII) having a leaving group $W^5$, the ether compound (XXXIII) can be obtained. The Mitsunobu reaction of the hydroxypyrimidine derivative (XXXI) and the alcohol compound (XXIV) can be performed in a solvent by using a phosphine reagent and an azo reagent or an ethylenedicarboxylic acid reagent, or a phosphonium ylide reagent. As the phosphine reagent, although not particularly limited, a trialkylphosphine or a triarylphosphine, specifically, trimethylphosphine, triethylphosphine, tripropylphosphine, triisopropylphosphine, tributylphosphine, triisobutylphosphine, tricyclohexylphosphine, triphenylphosphine, diphenylphosphinopolystyrene and the like can be used. As the azo reagent, although not particularly limited, diethyl azodicarboxylate (DEAD), diisopropyl azodicarboxylate, 1,1'-(azodicarbonyl) piperidine (ADDP), 1,1'-azobis(N,N'-diisopropylformamide) (TIPA), 1,6-dimethyl-1,5,7-hexahydro-1,4,6,7-tetrazocine-2,5-dione (DHTD) and the like can be used. As the ethylenedicarboxylic acid reagent, although not particularly limited, dimethyl maleate, diethyl maleate, dimethyl fumarate, diethyl fumarate and the like can be used. As the solvent, although not particularly limited, N,N'-dimethylformamide, tetrahydrofuran, dioxane, acetonitrile, propionitrile, nitromethane, acetone, ethyl acetate, isopropyl acetate, benzene, toluene, chlorobenzene, chloroform, dichloromethane, 1,2-dichloroethane and the like may be used alone or in combination. As for the reaction conditions, although they should be changed depending on the hydroxypyrimidine derivative represented by the general formula (XXXI) used, the target compound can be obtained by performing the reaction generally at 0 to 120° C., preferably 0 to 100° C., for 30 minutes to 3 days, preferably 30 minutes to 50 hours.

The reaction of the hydroxypyrimidine derivative (XXXI) and the compound (XXXII) having a leaving group $W^5$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination, and as the a base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The method for removing the protective group $R^{23}$ of the ether compound (XXXIII) obtained by the aforementioned method, although not particularly limited, can be performed by referring to a method generally used for removal of the protective group (Protective Groups in Organic Synthesis Third Edition, John Wiley & Sons, Inc.).

In addition, the hydroxypyrimidine derivative (XXXI) used in the aforementioned preparation method can also be prepared by the following method, besides the aforementioned methods. Namely, as shown in the following reaction scheme 8, it can be prepared by protecting the amino group and hydroxy group of 5-hydroxypyrimidin-2-amine (XXXIV) with the protective groups $R^{23}$ to obtain a compound represented by the general formula (XXXV), and selectively removing the protective group $R^{23}$ of the oxygen functional group. The protective group $R^{23}$ in the general formula (XXXV) is generally a protective group which can be introduced into both hydroxy group and amino group, and although not particularly limited, formyl group, acetyl group, propionyl group, butyryl group, hexanoyl group, trimethylacetyl group, trifluoroacetyl group, benzoyl group, cyclohexylcarbonyl group, benzyloxycarbonyl group, 2,2,2-trichloroethylcarbonyl group, t-butoxycarbonyl group, 4-methoxybenzyl group, benzyl group, 3,4-dimethoxybenzyl group, 2,4,6-trimethylbenzyl group, trifluoromethanesulfonyl group and the like are preferred.

This reaction route is represented by reaction formulas as follows.

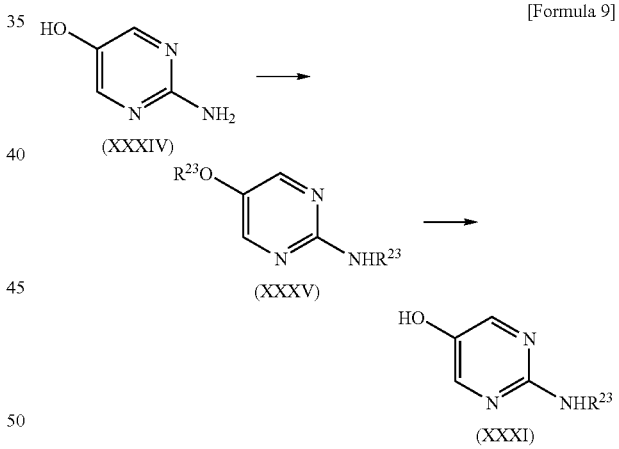

Reaction scheme 8

[Formula 9]

(wherein $R^{23}$ represents a protective group)

The method for introducing the protective group $R^{23}$ into the amino group and hydroxy group of 5-hydroxypyrimidin-2-amine (XXXIV), although not particularly limited, can be performed by referring to a method generally used for introduction of the protective group (Protective Groups in Organic Synthesis Third Edition, John Wiley & Sons, Inc.).

The method for removing the protective group $R^{23}$ introduced into the oxygen functional group of the compound (XXXV) obtained by the aforementioned method, although not particularly limited, can be performed by referring to a method generally used for removal of the protective group (Protective Groups in Organic Synthesis Third Edition, John Wiley & Sons, Inc.).

3 Preparation Method of Compound (VI) Having a Leaving Group $W^2$

As the aforementioned the compound (VI) having a leaving group $W^2$, an available compound may be used per se, or it can be suitably prepared by a known method. For example, said compound can be prepared by the following method. However, the preparation method is not limited to the following example.

As shown in the following reaction scheme 9, by reducing the ketone derivative represented by the general formula (VII), an alcohol derivative represented by the general formula (XXXVIII) can be obtained. Further, by reacting an aldehyde derivative represented by the general formula (XXXVI) with an alkyl metal reagent represented by the general formula (XXXVII), the alcohol derivative represented by the general formula (XXXVIII) can be obtained. As the metal M in the general formula (XXXVII), an alkali metal such as lithium, sodium and potassium, or a magnesium halide forming a Grignard reagent such as magnesium chloride, magnesium bromide and magnesium iodide is preferred. By converting the alcohol moiety of the alcohol derivative represented by the general formula (XXXVIII) into the leaving group $W^2$, the compound having the leaving group $W^2$ represented by the general formula (VI) can be obtained.

This reaction route is represented by reaction formulas as follows.

The reduction reaction of the ketone derivative (VII) can be performed in a solvent by using a reducing reagent. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, acetic acid, trifluoroacetic acid and the like may be used alone or in combination. As the reducing reagent, although not particularly limited, borohydride type reagents such as sodium triacetoxyborohydride, tetramethylammonium triacetoxyborohydride, sodium cyanoborohydride, sodium borohydride, lithium borohydride, sodium trimethoxyborohydride and lithium triethylborohydride, and aluminum hydride reagents such as lithium aluminum hydride, diisopropylaluminum hydride and sodium bis(2-methoxyethoxy)aluminum hydride can be used.

The reaction of the aldehyde derivative (XXXVI) and the alkyl metal reagent represented by the general formula (XXXVII) can be performed by reacting both compounds in an anhydrous solvent. As the solvent, although not particularly limited, for example, tetrahydrofuran, toluene, dioxane, hexane and the like may be used alone or in combination. As for the reaction conditions, although they should be changed Reaction scheme 9

[Formula 10]

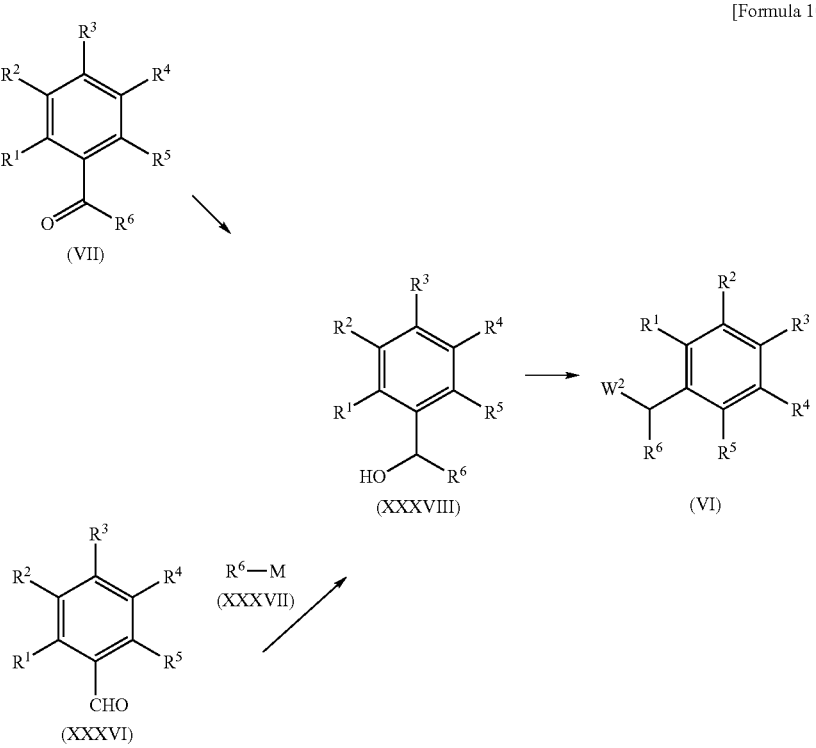

(wherein $R^1$, $R^2$, $R^3$, $R^4$, $R^5$ and $R^6$ have the same meanings as those explained for the general formula (I) mentioned above, and $W^2$ represents a halogen atom, an alkylsulfonyloxy group, a haloalkylsulfonyloxy group or an arylsulfonyloxy group)

depending on the starting materials used, the target compound, the alcohol compound (XXXVIII), can be obtained by performing the reaction generally at −100 to 100° C., preferably −78 to 50° C., for 5 minutes to 72 hours, preferably 10 minutes to 24 hours.

The reaction for synthesizing the compound (VI) having a leaving group $W^2$ from the alcohol compound (XXXVIII) can be selected depending on the type of the leaving group $W^2$ as follows.

When $W^2$ of the compound (VI) having a leaving group $W^2$ is sulfonyloxy group, the compound (VI) can be obtained by a reaction of the alcohol compound (XXXVIII) and a sulfonic acid esterifying agent in a solvent in the presence or absence of a base. As the sulfonic acid esterifying agent, although not particularly limited, for example, methanesulfonyl chloride, methanesulfonic anhydride, ethanesulfonyl chloride, benzylsulfonyl chloride, allylsulfonyl chloride, trifluoromethanesulfonyl chloride, trifluoromethanesulfonic anhydride, chloromethanesulfonyl chloride, benzenesulfonyl chloride, p-toluenesulfonyl chloride, o-nitrobenzenesulfonyl chloride, or p-nitrobenzenesulfonyl chloride can be used. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, N,N-dimethylformamide and the like may be used alone or in combination. As the base, although not particularly limited, for example, organic bases such as pyridine, DMAP, collidine, lutidine, DBU, DBN, DABCO, triethylamine, N,N-diisopropylethylamine, N,N-diisopropylpentylamine, and trimethylamine, alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, hydrogencarbonates such as sodium hydrogencarbonate and potassium hydrogencarbonate and the like can be used.

When $W^2$ of the compound (VI) having a leaving group $W^2$ is a halogen atom, the compound (VI) can be obtained by a reaction of the alcohol compound (XXXVIII) and a halogenating agent in a solvent or without solvent in the presence or absence of a base. Examples of the halogenating agent include, although not particularly limited, chlorinating agents, brominating agents or iodinating agents such as phosphorus oxychloride, phosphorus pentachloride, triphenylphosphine dichloride, triphenylphosphine dibromide, triphenylphosphite dichloride, triphenylphosphite dibromide, phosphorus tribromide, thionyl chloride, triphenylphosphine and carbon tetrachloride, triphenylphosphine and carbon tetrabromide, triphenylphosphine, iodine and imidazole, triphenylphosphine and NIS, and methanesulfonyl chloride and DMAP. As the solvent, for example, 1,2-dichloroethane, chloroform, dichloromethane, diethyl ether, ethyl acetate, isopropyl acetate, toluene, benzene, tetrahydrofuran, dioxane, acetonitrile, propionitrile and the like may be used alone or in combination. As the base, although not particularly limited, for example, organic bases such as pyridine, DMAP, collidine, lutidine, DBU, DBN, DABCO, triethylamine, N,N-diisopropylethylamine, N,N-diisopropylpentylamine, and trimethylamine, alkali metal carbonates such as lithium carbonate, sodium carbonate, potassium carbonate and cesium carbonate, hydrogencarbonates such as sodium hydrogencarbonate and potassium hydrogencarbonate and the like can be used.

Preparation Methods of the Compound Represented by the General Formula (I) wherein $R^{13}$ is a (lower alkyl)sulfinyl (lower alkoxy) Group or a (lower alkyl)sulfonyl(lower alkoxy) Group or a Salt Thereof, or a Solvate Thereof.

The compound represented by the general formula (I) wherein $R^{13}$ is a (lower alkyl)sulfinyl(lower alkoxy) group or a (lower alkyl)sulfonyl(lower alkoxy) group can also be prepared by, besides the aforementioned methods, the following reaction steps. Namely, it can be obtained by oxidizing sulfur atom of a compound represented by the general formula (I) wherein $R^{13}$ is a (lower alkyl)thio(lower alkoxy) group, which is prepared by using the pyrimidin-2-amine derivative (IV'') wherein $R^{13}$ is a (lower alkyl)thio(lower alkoxy) group.

As the oxidation method, an ordinary method for converting sulfur atom into sulfinyl group or sulfonyl group can be applied, and for example, an oxidation reaction with aqueous hydrogen peroxide using a catalytic amount of sodium tungstate, molybdenum dioxide dichloride or tantalum pentachloride, or sodium periodate, potassium periodate, metachloroperbenzoic acid (mCPBA), PCC, PDC, N-chlorosuccinimide (NCS), N-bromosuccinimide (NBS), NIS, iodine, bromine and the like can be used. As the solvent, although not particularly limited, for example, water, methanol, ethanol, isopropanol, acetonitrile, acetone, tetrahydrofuran, dichloromethane, chloroform, 1,2-dichloroethane, carbon tetrachloride, N,N-dimethylformamide, acetic acid and the like may be used alone or in combination.

Further, the compound represented by the general formula (I) wherein $R^{13}$ is a (lower alkyl)sulfonyl(lower alkoxy) group can also be prepared from the compound represented by the general formula (I) wherein $R^{13}$ is a (lower alkyl)sulfinyl(lower alkoxy) group by using similar oxidation reaction conditions.

Preparation Method of Compound Represented by the General Formula (I) Wherein $R^{13}$ is Hydroxy Group, or Salt Thereof, or Solvate Thereof.

The compound represented by the general formula (I) wherein $R^{13}$ is hydroxy group can also be prepared by the following reaction steps, as well as by appropriate use of the aforementioned methods. Namely, the compound represented by the general formula (I) wherein $R^{13}$ is hydroxy group can be prepared by preparing a compound represented by the general formula (I) using the aminopyrimidine derivative (XXIX) as the pyrimidin-2-aminederivative (IV) according to the reaction scheme 1 or 2, and removing the protective group at the position of $R^{13}$.

Intermediate compounds and target compounds obtained by the aforementioned reactions can be isolated and purified as required by purification methods commonly used in the field of synthetic organic chemistry, for example, filtration, extraction, washing, drying, concentration, recrystallization, various types of chromatography, and the like. Intermediate compounds may also be used for successive reactions without particular purification.

Further, various kinds of isomers can be isolated by applying conventional methods utilizing differences of physicochemical properties of the isomers. For example, a racemic mixture can be derived into optically pure isomers by a usual racemic resolution method such as a method of forming diastereomeric salts with a common optically active acid such as tartaric acid, and performing optical resolution, or a method of using optically active column chromatography. Moreover, the resolution of a diasteromer mixture can also be attained by, for example, fractional crystallization, various chromatography techniques, and the like. Further, an optically active compound can also be prepared by using a suitable optically active starting material.

The resulting compound (I) can be made into an acid addition salt by an ordinary method. The compound may also be obtained as a solvate with a solvent such as a reaction solvent and a recrystallization solvent or a hydrate.

Examples of dosage form of the medicament comprising the compound of the present invention, a salt thereof or a solvate thereof as an active ingredient include, for example, those for oral administration such as tablet, capsule, granule, powder and syrup, and those for parenteral administration such as intravenous injection, intramuscular injection, suppository, inhalant, transdermal preparation, eye drop and nasal drop. In order to prepare medicinal formulations in the various dosage forms, the active ingredient may be used alone, or may be used in appropriate combination with other pharmaceutically acceptable additives such as excipients, binders, fillers, disintegrating agents, surface active agents, lubricants, dispersing agents, buffering agents, preservatives, corrigents, perfumes, coating agents and diluents to obtain as a pharmaceutical composition.

The HMG-CoA reductase inhibitor used for the combinatory composition for the medicament of the present invention is a compound which inhibits the biological conversion of hydroxymethylglutaryl-coenzyme A into mevalonic acid, catalyzed by the HMG-CoA reductase, and examples include lovastatin, simvastatin, fluvastatin, pravastatin, pitavastatin, atorvastatin, rosvastatin and the like.

Although a dose of the medicament, CETP inhibitor, or HDL-increasing agent of the present invention may vary depending on the weight, age, sexuality, and symptoms of a patient and the like, it is generally preferred that 0.1 to 500 mg, especially 1 to 300 mg, in terms of the compound represented by the general formula (I), may be orally or parenterally administered at one time or several times as divided portions per day for an adult.

EXAMPLES

The present invention will be explained with reference to examples. However, the present invention is not limited to these examples. The abbreviations used in the following examples have the following meanings.

s: Singlet
d: Doublet
t: Triplet
q: Quartet
m: Multiplet
br: Broad
J: Coupling constant
Hz: Hertz
$CDCl_3$: Deuterated chloroform
$d_6$-DMSO: Deuterated dimethyl sulfoxide
$^1$H-NMR: Proton nuclear magnetic resonance
IR: Infrared absorption spectrum

Example 1

Preparation of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine Step 1: Preparation of 5-[2-(methylthio)ethoxy]pyrimidin-2-amine 5-[2-(Methylthio)ethoxy]pyrimidin-2-amine was prepared by the method described in a) mentioned below. Further, it was also prepared separately by the method described in b) mentioned below. In the preparation, N-(5-hydroxypyrimidin-2-yl)hexanamide, a preparation intermediate of the method of b) described below, was also prepared by, besides the method described in b), the methods described in c) and d) mentioned below.

a) Preparation of 5-[2-(methylthio)ethoxy]pyrimidin-2-amine (1)

5-Bromo-2-chloropyrimidine (300 mg, 1.55 mmol) was dissolved by heating at 120° C. in 4-methoxybenzylamine (2.10 g, 15.4 mmol), and the solution was stirred at the same temperature for 2 hours. The reaction mixture was directly subjected to silica gel column chromatography (hexane:ethyl acetate=30:1→5:1) for purification to obtain 5-bromo-N-(4-methoxybenzyl)pyrimidin-2-amine (445 mg, 98%) as a colorless amorphous solid.

$^1$H-NMR ($CDCl_3$) δ: 3.80 (3H, s), 4.52 (2H, d, J=5.4 Hz), 5.45 (1H, br), 6.87 (2H, d, J=8.4 Hz), 7.24 (2H, d, J=8.4 Hz), 8.28 (2H, s).

5-Bromo-N-(4-methoxybenzyl)pyrimidin-2-amine (300 mg, 1.02 mmol) was suspended in toluene (20 mL), the suspension was added with cuprous iodide (200 mg, 1.05 mmol), 2-methylthioethanol (1.06 g, 11.5 mmol), N,N'-dimethylethylenediamine (0.83 g, 9.42 mmol) and cesium carbonate (400 mg, 1.22 mmol), and the mixture was stirred at 110° C. for 66 hours in an argon atmosphere. The reaction mixture was separated by silica gel column chromatography (ethyl acetate), and then purified by preparative silica gel thin layer chromatography (hexane:ethyl acetate=1:1) to obtain N-(4-methoxybenzyl)-5-[2-(methylthio)ethoxy]pyrimidin-2-amine (172 mg) as a colorless amorphous solid.

$^1$H-NMR ($CDCl_3$) δ: 2.20 (3H, s), 2.85 (2H, t, J=6.8 Hz), 3.80 (3H, s), 4.10 (2H, t, J=6.8 Hz), 4.51 (2H, d, J=5.9 Hz), 5.31 (1H, br), 6.86 (2H, d, J=8.6 Hz), 7.28 (2H, d, J=8.6 Hz), 8.05 (2H, s).

N-(4-Methoxybenzyl)-5-[2-(methylthio)ethoxy]pyrimidin-2-amine (172 mg) was dissolved in trifluoroacetic acid (3 mL) at room temperature, and the solution was stirred at 60° C. for 2.5 hours. The reaction mixture was concentrated under reduced pressure, and the resulting residue was purified by preparative silica gel thin layer chromatography (chloroform:methanol=15:1) to obtain 5-[2-(methylthio)ethoxy]pyrimidin-2-amine (34 mg, 18% in 2 steps) as a colorless amorphous solid.

$^1$H-NMR ($CDCl_3$) δ: 2.21 (3H, s), 2.85 (2H, t, J=6.6 Hz), 4.13 (2H, t, J=6.6 Hz), 4.93 (2H, br), 8.06 (2H, s).

b) Preparation of 5-[2-(methylthio)ethoxy]pyrimidin-2-amine (2)

5-Methoxypyrimidin-2-amine (12.3 g, 98.3 mmol) was dissolved in pyridine (123 mL), the solution was added with hexanoyl chloride (14.5 g, 108 mmol) on an ice bath, and the mixture was stirred at room temperature for 30 minutes. The reaction mixture was added with 1 M aqueous glycine (98.3 mL) at 0° C., and the mixture was stirred for 1 hour, and then extracted with chloroform. The organic layer was washed with saturated brine, dried over anhydrous sodium sulfate, and then concentrated under reduced pressure, and the resulting residue was azeotroped with toluene. The resulting residue was recrystallized from chloroform-hexane to obtain N-(5-methoxypyrimidin-2-yl)hexanamide (18.4 g, 84%) as a colorless solid.

$^1$H-NMR ($CDCl_3$) δ: 0.91 (3H, t, J=7.1 Hz), 1.30-1.40 (4H, m), 1.70-1.78 (2H, m), 2.50-2.70 (2H, m), 3.89 (3H, s), 8.10 (1H, br), 8.28 (2H, s).

N-(5-Methoxypyrimidin-2-yl)hexanamide (17.3 g, 77 mmol) was suspended in 1,2-dichloroethane (170 mL), the suspension was added with boron tribromide (20.5 mL, 216 mmol), and the mixture was refluxed by heating for 30 minutes. The reaction mixture was inactivated with methanol (170 mL) under ice cooling. The reaction mixture was concentrated under reduced pressure, the resulting residue was added with saturated ammonia in methanol (85 mL) under ice cooling, and the mixture was homogenized. The reaction mixture was concentrated under reduced pressure, and the resulting residue was added with water, and extracted with chloroform. The organic layer was washed with saturated brine, dried over anhydrous sodium sulfate, and then concentrated under reduced pressure, and the resulting residue was isolated and purified by silica gel column chromatography (hexane:acetone=2:1) to obtain N-(5-hydroxypyrimidin-2-yl)hexanamide (9.36 g, 59%) as a pale yellow solid.

$^1$H-NMR (d$_6$-DMSO) δ: 0.86 (3H, t, J=7.3 Hz), 1.24-1.31 (4H, m), 1.51-1.58 (2H, m), 2.35 (2H, t, J=7.3 Hz), 8.20 (2H, s), 10.09 (1H, br s), 10.21 (1H, s).

N-(5-Hydroxypyrimidin-2-yl)hexanamide (8.18 g, 39 mmol) and triphenylphosphine (20.5 g, 78 mmol) were mixed, and dried under reduced pressure, and then the atmosphere was substituted with argon. These substances were dissolved by heating in anhydrous N,N-dimethylformamide (80 mL), and the solution was cooled to room temperature, and then added with 2-methylthioethanol (5.40 g, 58.6 mmol). The reaction mixture was added with DEAD (2.2 M solution in toluene, 26.6 mL, 58.6 mmol) on an ice bath, and the mixture was stirred at room temperature for 2 hours. The reaction mixture was added with water (300 mL), and the mixture was stirred for 15 minutes, and then extracted with chloroform. The organic layer was washed with saturated brine, dried over anhydrous sodium sulfate, and then concentrated under reduced pressure, the resulting residue was dissolved in saturated ammonia in methanol (60 mL), and the solution was left at room temperature for 1 hour. The reaction mixture was concentrated under reduced pressure, and the resulting residue was purified by silica gel column chromatography (hexane:ethyl acetate=3:1→hexane:acetone=2:1), the eluate was concentrated under reduced pressure, and the resulting residue was dissolved in chloroform by heating. The crystals obtained by ice cooling of the solution were removed, and the filtrate was concentrated under reduced pressure. The residue was recrystallized from chloroform-hexane to obtain N-{5-[2-(methylthio)ethoxy]pyrimidin-2-yl}hexanamide (6.80 g, 61%) as a pale dark brown solid.

$^1$H-NMR (CDCl$_3$) δ: 0.91 (3H, t, J=7.1 Hz), 1.26-1.41 (4H, m), 1.70-1.78 (2H, m), 2.22 (3H, s), 2.52-2.68 (2H, m), 2.90 (2H, t, J=6.6 Hz), 4.22 (2H, t, J=6.6 Hz), 8.21 (1H, br), 8.30 (2H, s).

N-{5-[2-(Methylthio)ethoxy]pyrimidin-2-yl}hexanamide (6.80 g, 24 mmol) was suspended in methanol (68 mL), the suspension was added with sodium methoxide (1 M solution in methanol, 120 mL, 120 mmol), the substances in the suspension were dissolved on an oil bath at 60° C., and the solution was stirred at the same temperature for 2 hours. The reaction mixture was concentrated under reduced pressure, the resulting residue was extracted with chloroform and water, and the organic layer was washed with saturated brine, dried over anhydrous sodium sulfate, and then concentrated under reduced pressure. The resulting residue was washed with ether-hexane, and taken by filtration to obtain 5-[2-(methylthio)ethoxy]pyrimidin-2-amine (2.93 g, 59%) as a pale yellow solid.

c) Preparation of
N-(5-hydroxypyrimidin-2-yl)hexanamide (2)

5-Hydroxypyrimidin-2-amine (40.0 g, 360 mmol) was dissolved in pyridine (200 mL), the solution was added with hexanoyl chloride (121 g, 899 mmol), and the mixture was stirred at room temperature for 0.5 hour. The reaction mixture was added with methanol (100 mL), the mixture was concentrated under reduced pressure, and the resulting residue was diluted with water, and extracted with ethyl acetate. The organic layer was washed with saturated brine, dried over anhydrous sodium sulfate, and then concentrated under reduced pressure, and the resulting residue was dissolved in methanol (200 mL). The solution was added with saturated ammonia solution in methanol (250 mL) under ice cooling and stirring, and the mixture was stirred overnight at room temperature. The reaction mixture was concentrated under reduced pressure, and the resulting residue was purified by silica gel column chromatography (hexane:acetone=2:1) to obtain N-(5-hydroxypyrimidin-2-yl)hexanamide (39.5 g, 52%) as a colorless solid.

d) Preparation of
N-(5-hydroxypyrimidin-2-yl)hexanamide (3)

[(2,2-Diethoxyethoxy)methyl]benzene (8.30 g, 37.0 mmol) stirred under ice cooling was added with phosphorus pentachloride (8.09 g, 38.8 mmol) over 15 minutes. The mixture was stirred at the same temperature for 15 minutes, and then heated and stirred on an oil bath at 75° C. for 75 minutes. The reaction mixture was cooled by stirring at room temperature for 20 minutes, and then added with anhydrous N,N-dimethylformamide (8.6 mL, 111 mmol) at the same temperature, and the mixture was stirred at room temperature for 3 days. The reaction mixture was added with 8 M aqueous sodium hydroxide on an ice bath until pH became 8 or higher, and then the mixture was diluted with water, and extracted with ether. The organic layer was washed successively with water and saturated brine, dried over anhydrous sodium sulfate, and then concentrated under reduced pressure, and the resulting residue was purified by silica gel column chromatography (hexane:acetone=4:1→2:1) to obtain 2-(benzyloxy)-3-(dimethylamino)acrylaldehyde (4.05 g, 53%) as a brown oil.

$^1$H-NMR (CDCl$_3$) δ: 3.04 (6H, s), 4.96 (2H, s), 6.17 (1H, s), 7.28-7.43 (5H, m), 8.64 (1H, s).

2-(Benzyloxy)-3-(dimethylamino)acrylaldehyde (10.9 g, 53 mmol) was dissolved in N-methylpyrrolidone (85 mL), the solution was added with guanidine hydrochloride (15.3 g, 160 mmol), and then the mixture was added with sodium hydride (50% in oil, 15.3 g, 320 mmol) with stirring on an ice bath, and stirred on an oil bath at 80° C. for 1 hour. The reaction mixture was added with water on an ice bath to decompose excessive sodium hydride, and then extracted with ether and water, and the organic layer was washed successively with water and saturated brine, dried over anhydrous sodium sulfate, and then concentrated under reduced pressure. The resulting residue was purified by silica gel column chromatography (hexane:acetone=10:1→4:1→2:1→1:1), and the eluate was concentrated under reduced pressure. Then, the resulting residue was washed with ether-hexane, and taken by filtration to obtain 5-(benzyloxy)pyrimidin-2-amine (6.99 g, 65%) as a pale yellow solid.

$^1$H-NMR (CDCl$_3$) δ: 4.76 (2H, br s), 5.03 (2H, s), 7.28-7.43 (5H, m), 8.08 (2H, s).

A solution of 5-(benzyloxy)pyrimidin-2-amine (60.0 g, 0.30 mmol) in dichloromethane (400 mL) was added with pyridine (30 mL, 0.37 mmol), the mixture was added dropwise with a solution of hexanoyl chloride (46.0 g, 0.34 mmol) in dichloromethane (100 mL) with stirring on an ice bath, and the mixture was stirred at the same temperature for 1 hour. The reaction mixture was added with 1 M hydrochloric acid (500 mL), and extracted with chloroform, and the organic layer was successively washed with water and saturated brine, dried over anhydrous sodium sulfate, and then concentrated under reduced pressure. The resulting residue was recrystallized from chloroform-hexane to obtain N-[5-(benzyloxy)pyrimidin-2-yl]hexanamide (87.1 g, 98%) as colorless needles.

$^1$H-NMR (CDCl$_3$) δ: 0.90 (3H, t, J=6.9 Hz), 1.34-1.39 (4H, m), 1.69-1.75 (2H, m), 2.55-2.61 (2H, m), 5.12 (2H, s), 7.34-7.44 (5H, m), 7.96 (1H, br), 8.32 (2H, s).

N-[5-(Benzyloxy)pyrimidin-2-yl]hexanamide (87.1 g, 0.29 mmol) was dissolved in methanol (2.4 L), the solution was added with 10% palladium/carbon (20 g), and the mixture was stirred at room temperature for 3 hours under hydrogen atmosphere. The reaction mixture was filtered, the filtrate was concentrated under reduced pressure, and the resulting residue was purified by silica gel column chromatography (chloroform:methanol=30:1) to obtain N-(5-hydroxypyrimidin-2-yl)hexanamide (28.0 g, 46%) as a pale yellow solid.

Step 2: Preparation of
1-bromo-1-[3,5-bis(trifluoromethyl)phenyl]ethane

To a solution of 3,5-bis(trifluoromethyl)acetophenone (2.00 g, 7.81 mmol) in methanol (20 mL) was added sodium borohydride (591 mg, 15.6 mmol) with stirring on an ice bath, and the mixture was stirred at the same temperature for 30 minutes. The reaction mixture was added with 1 M hydrochloric acid on an ice bath until pH became 7 or lower, and then concentrated under reduced pressure, the resulting residue was added with water (20 mL), and the mixture was extracted with ethyl acetate. The organic layer was washed with saturated brine, dried over anhydrous sodium sulfate, and then concentrated under reduced pressure to obtain 1-[3,5-bis(trifluoromethyl)phenyl]ethanol (2.00 g, 99%) as a colorless solid.

$^1$H-NMR (CDCl$_3$) δ: 1.55 (3H, d, J=6.6 Hz), 2.00 (1H, br s), 5.05 (1H, q, J=6.6 Hz), 7.79 (1H, s), 7.85 (2H, s).

To a solution of 1-[3,5-bis(trifluoromethyl)phenyl]ethanol (500 mg, 1.94 mmol) in toluene (5 mL) was added phosphorus tribromide (550 mg, 2.03 mmol), and the mixture was stirred overnight at room temperature. The reaction mixture was diluted with water, and extracted with ethyl acetate. The organic layer was washed with saturated brine, dried over anhydrous sodium sulfate, and then concentrated under reduced pressure, and the resulting residue was purified by silica gel column chromatography (hexane:ethyl acetate=10:1) to obtain 1-bromo-1-[3,5-bis(trifluoromethyl)phenyl]ethane (258 mg, 41%) as a colorless oil.

$^1$H-NMR (CDCl$_3$) δ: 2.08 (3H, d, J=7.1 Hz), 5.21 (1H, q, J=7.1 Hz), 7.81 (1H, s), 7.87 (2H, s).

Step 3: Preparation of 2-[(cyclopentylmethyl)(ethyl)amino]-5-(trifluoromethyl)benzaldehyde To a solution of 2-fluoro-5-(trifluoromethyl)benzaldehyde (3.00 g, 15.6 mmol) in toluene (60 mL) was added N-(cyclopentylmethyl)-N-ethylamine (2.70 g, 21.2 mmol) synthesized by the method described in International Patent Publication WO2006/073973 and potassium carbonate (6.50 g, 47.0 mmol), and the mixture was refluxed by heating for 68 hours. The reaction mixture was cooled to room temperature, then added with water, and extracted with chloroform. The organic layer was washed with saturated brine, then dried over anhydrous sodium sulfate, and concentrated under reduced pressure, and the resulting residue was purified by silica gel column chromatography (hexane:ethyl acetate=20:1) to obtain 2-[(cyclopentylmethyl)(ethyl)amino]-5-(trifluoromethyl)benzaldehyde (3.34 g, 71%) as a yellow oil.

$^1$H-NMR (CDCl$_3$) δ: 1.09-1.19 (5H, m), 1.43-1.72 (6H, m), 2.15 (1H, m), 3.17 (2H, d, J=7.6 Hz), 3.33 (2H, q, J=7.0 Hz), 7.19 (1H, d, J=9.0 Hz), 7.65 (1H, dd, J=2.4, 9.0 Hz), 8.03 (1H, d, J=2.4 Hz), 10.18 (1H, s).

Step 4: Preparation of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine To a solution of 2-[(cyclopentylmethyl)(ethyl)amino]-5-(trifluoromethyl)benzaldehyde (3.34 g, 11.2 mmol) obtained in Step 3 and 5-[2-(methylthio)ethoxy]pyrimidin-2-amine (2.27 g, 12.3 mmol) obtained in Step 1 in toluene (80 mL) was added acetic acid (317 mg, 5.19 mmol), and the mixture was refluxed by heating for 4 hours with a Dean-Stark apparatus. The reaction mixture was left to cool to room temperature, and then added with sodium triacetoxyborohydride (4.73 g, 22.3 mmol) on an ice bath with stirring, and the mixture was stirred at room temperature for 60 hours. The reaction mixture was added with water, and extracted with chloroform, and then the organic layer was washed with water and saturated brine, dried over anhydrous sodium sulfate, and concentrated under reduced pressure. The resulting residue was purified by silica gel column chromatography (hexane:ethyl acetate=20:1→10:1→4:1) to obtain N-({2-[(cyclopentylmethyl)(ethyl)amino]-5-(trifluoromethyl)phenyl}methyl)-5-[2-(methylthio)ethoxy]pyrimidin-2-amine (4.39 g, 84%) as a pale yellow oil.

$^1$H-NMR (CDCl$_3$) δ: 1.03 (3H, t, J=7.1 Hz), 1.15-1.23 (2H, m), 1.43-1.66 (4H, m), 1.67-1.76 (2H, m), 2.00 (1H, m), 2.20 (3H, s), 2.85 (2H, t, J=6.8 Hz), 2.95 (2H, d, J=7.6 Hz), 3.04 (2H, q, J=7.1 Hz), 4.12 (2H, t, J=6.8 Hz), 4.69 (2H, d, J=5.6 Hz), 5.54 (1H, t, J=5.6 Hz), 7.21 (1H, d, J=8.3 Hz), 7.44 (1H, d, J=8.3 Hz), 7.62 (1H, s), 8.07 (2H, s).

To a stirred solution of N-({2-[(cyclopentylmethyl)(ethyl)amino]-5-(trifluoromethyl)phenyl}methyl)-5-[2-(methylthio)ethoxy]pyrimidin-2-amine (4.39 g, 9.37 mmol) in tetrahydrofuran (40 mL) under ice cooling was added sodium hydride (50% in oil, 1.80 g, 37.5 mmol), and the mixture was stirred at 50° C. for 1 hour. After cooling to −78° C., to the reaction mixture was added a solution of 1-bromo-1-[3,5-bis(trifluoromethyl)phenyl]ethane (6.02 g, 18.7 mmol) obtained in Step 2 in N,N-dimethylformamide (40 mL), and the mixture was stirred for 2.5 hours with warming to room temperature. The reaction mixture was added with water and extracted with ethyl acetate, the organic layer was washed with saturated brine, dried over anhydrous sodium sulfate, and then concentrated under reduced pressure, and the resulting residue was purified by silica gel column chromatography (hexane:ethyl acetate=20:1) to obtain the target compound, N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine (6.03 g, 91%), as a pale yellow oil.

Examples 2 and 3

Preparation of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfinyl)ethoxy]pyrimidin-2-amine and N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfonyl)ethoxy]pyrimidin-2-amine To a solution of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine (348 mg, 0.49 mmol) obtained in Example 1 in acetonitrile (7 mL) was added molybdenum dioxide dichloride (14.6 mg, 0.073 mmol) and 30% aqueous hydrogen peroxide (220 mg, 1.94 mmol), and the mixture was stirred at room temperature for 23 hours. The reaction mixture was added with saturated aqueous sodium sulfite, and extracted with chloroform. Then, the organic layer was washed with saturated brine, dried over anhydrous sodium sulfate, and concentrated under reduced pressure. The resulting residue was purified by preparative silica gel thin layer chromatography (hexane:acetone=2:1) to obtain N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfinyl)ethoxy]pyrimidin-2-amine (compound of Example 2, 32.8 mg, 9%) as yellow oil, and N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfonyl)ethoxy]pyrimidin-2-amine (compound of Example 3, 295 mg, 81%) as a pale yellow oil.

Example 4

Preparation of N-{1-[3,5-bis(trifluoromethyl)phenyl]ethyl}-N-({2-[(cyclopentylmethyl)(ethyl)amino]-5-methoxyphenyl}methyl)-5-[2-(methylthio)ethoxy]pyrimidin-2-amine By using 2-fluoro-5-methoxybenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-5-methoxybenzaldehyde as a yellow oil.

$^1$H-NMR (CDCl$_3$) δ: 0.98 (3H, t, J=7.1 Hz), 1.09-1.24 (2H, m), 1.38-1.70 (6H, m), 1.94 (1H, m), 2.94 (2H, d, J=7.6 Hz), 3.06 (2H, q, J=7.1 Hz), 3.83 (3H, s), 7.12 (1H, dd, J=3.2, 8.8 Hz), 7.23 (1H, d, J=8.8 Hz), 7.31 (1H, d, J=3.2 Hz), 10.49 (1H, s).

By using 2-[(cyclopentylmethyl)(ethyl)amino]-5-methoxybenzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-5-methoxyphenyl}methyl)-5-[2-(methylthio)ethoxy]pyrimidin-2-amine, as a pale yellow oil.

Example 5

Preparation of N-{1-[3,5-bis(trifluoromethyl)phenyl]ethyl}-N-({2-[(cyclopentylmethyl)(ethyl)amino]-5-methoxyphenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-5-methoxyphenyl}methyl)-5-[2-(methylthio)ethoxy]pyrimidin-2-amine obtained in Example 4 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-5-methoxyphenyl}methyl)-5-[2-(methylsulfonyl)ethoxy]pyrimidin-2-amine, as a pale yellow oil.

Example 6

Preparation of N-{1-[3,5-bis(trifluoromethyl)phenyl]ethyl}-N-({2-[(cyclopentylmethyl)(ethyl)amino]-3,5-difluorophenyl}methyl)-5-[2-(methylthio)ethoxy]pyrimidin-2-amine By using 2,3,5-trifluorobenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-3,5-difluorobenzaldehyde as a yellow oil.

$^1$H-NMR (CDCl$_3$) δ: 0.99 (3H, t, J=6.6 Hz), 1.07-1.20 (2H, m), 1.41-1.70 (6H, m), 1.89 (1H, m), 3.03 (2H, d, J=7.6 Hz), 3.13 (2H, q, J=6.6 Hz), 7.04 (1H, m), 7.34 (1H, m), 10.50 (1H, d, J=3.4 Hz).

By using 2-[(cyclopentylmethyl)(ethyl)amino]-3,5-difluorobenzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-3,5-difluorophenyl}methyl)-5-[2-(methylthio)ethoxy]pyrimidin-2-amine, as a pale yellow oil.

Example 7

Preparation of N-{1-[3,5-bis(trifluoromethyl)phenyl]ethyl}-N-({2-[(cyclopentylmethyl)(ethyl)amino]-3,5-difluorophenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-3,5-difluorophenyl}methyl)-5-[2-(methylthio)ethoxy]pyrimidin-2-amine obtained in Example 6 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-3,5-difluorophenyl}methyl)-5-[2-(methylsulfonyl)ethoxy]pyrimidin-2-amine, as a pale yellow oil.

Example 8

Preparation of N-{1-[3,5-bis(trifluoromethyl)phenyl]ethyl}-N-({2-[(cyclopentylmethyl)(ethyl)amino]-5-methylphenyl}methyl)-5-[2-(methylthio)ethoxy]pyrimidin-2-amine By using 2-fluoro-5-methylbenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-5-methylbenzaldehyde as a yellow oil.

$^1$H-NMR (CDCl$_3$) δ: 1.00 (3H, t, J=7.1 Hz), 1.14-1.19 (2H, m), 1.43-1.67 (6H, m), 2.01 (1H, m), 2.33 (3H, s), 2.99 (2H, d, J=7.6 Hz), 3.12 (2H, q, J=7.1 Hz), 7.13 (1H, d, J=8.3 Hz), 7.32 (1H, dd, J=2.2, 8.3 Hz), 7.62 (1H, d, J=2.2 Hz), 10.39 (1H, s).

By using 2-[(cyclopentylmethyl)(ethyl)amino]-5-methylbenzaldehyde instead of 2-[(cyclopentylmethyl)(ethyl)

amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-5-methylphenyl}methyl)-5-[2-(methylthio)ethoxy]pyrimidin-2-amine, as a pale yellow oil.

Example 9

Preparation of N-{1-[3,5-bis(trifluoromethyl)phenyl]ethyl}-N-({2-[(cyclopentylmethyl)(ethyl)amino]-5-methylphenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-5-methylphenyl}methyl)-5-[2-(methylthio)ethoxy]pyrimidin-2-amine obtained in Example 8 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-5-methylphenyl}methyl)-5-[2-(methylsulfonyl)ethoxy]pyrimidin-2-amine, as a pale yellow oil.

Example 10

Preparation of N-{1-[3,5-bis(trifluoromethyl)phenyl]ethyl}-N-({2-[(cyclopentylmethyl)(ethyl)amino]-4-fluorophenyl}methyl)-5-[2-(methylthio)ethoxy]pyrimidin-2-amine By using 2,4-difluorobenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-4-fluorobenzaldehyde as a yellow oil.

$^1$H-NMR (CDCl$_3$) δ: 1.07 (3H, t, J=7.1 Hz), 1.10-1.21 (2H, m), 1.42-1.73 (6H, m), 2.11 (1H, m), 3.06 (2H, d, J=7.6 Hz), 3.23 (2H, q, J=7.1 Hz), 6.75 (1H, m), 6.82 (1H, dd, J=2.4, 8.8 Hz), 7.81 (1H, dd, J=7.1, 8.8 Hz), 10.18 (1H, s).

By using 2-[(cyclopentylmethyl)(ethyl)amino]-4-fluorobenzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-4-fluorophenyl}methyl)-5-[2-(methylthio)ethoxy]pyrimidin-2-amine, as a pale yellow oil.

Example 11

Preparation of N-{1-[3,5-bis(trifluoromethyl)phenyl]ethyl}-N-({2-[(cyclopentylmethyl)(ethyl)amino]-4-fluorophenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-4-fluorophenyl}methyl)-5-[2-(methylthio)ethoxy]pyrimidin-2-amine obtained in Example 10 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-4-fluorophenyl}methyl)-5-[2-(methylsulfonyl)ethoxy]pyrimidin-2-amine, as a pale yellow oil.

Example 12

Preparation of N-{1-[3,5-bis(trifluoromethyl)phenyl]ethyl}-N-({2-[(cyclopentylmethyl)(ethyl)amino]-4-methoxyphenyl}methyl)-5-[2-(methylthio)ethoxy]pyrimidin-2-amine By using 2-fluoro-4-methoxybenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-4-methoxybenzaldehyde as a yellow oil.

$^1$H-NMR (CDCl$_3$) δ: 1.05 (3H, t, J=7.1 Hz), 1.14-1.19 (2H, m), 1.46-1.68 (6H, m), 2.10 (1H, m), 3.03 (2H, d, J=7.6 Hz), 3.20 (2H, q, J=7.1 Hz), 3.89 (3H, s), 6.60-6.64 (2H, m), 7.80 (1H, d, J=9.5 Hz), 10.18 (1H, s).

By using 2-[(cyclopentylmethyl)(ethyl)amino]-4-methoxybenzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-4-methoxyphenyl}methyl)-5-[2-(methylthio)ethoxy]pyrimidin-2-amine, as a pale yellow oil.

Example 13

Preparation of N-{1-[3,5-bis(trifluoromethyl)phenyl]ethyl}-N-({2-[(cyclopentylmethyl)(ethyl)amino]-4-methoxyphenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-4-methoxyphenyl}methyl)-5-[2-(methylthio)ethoxy]pyrimidin-2-amine obtained in Example 12 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-4-methoxyphenyl}methyl)-5-[2-(methylsulfonyl)ethoxy]pyrimidin-2-amine, as a pale yellow oil.

Example 14

Preparation of N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylthio)ethoxy]pyrimidin-2-amine By using 2-fluoro-4-(trifluoromethyl)benzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-4-(trifluoromethyl)benzaldehyde as a yellow oil.

$^1$H-NMR (CDCl$_3$) δ: 1.05-1.19 (5H, m), 1.50-1.71 (6H, m), 2.08 (1H, m), 3.12 (2H, d, J=7.8 Hz), 3.26 (2H, q, J=7.1 Hz), 7.28 (1H, d, J=7.8 Hz), 7.37 (1H, s), 7.87 (1H, d, J=7.8 Hz), 10.28 (1H, s).

By using 2-[(cyclopentylmethyl)(ethyl)amino]-4-(trifluoromethyl)benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylthio)ethoxy]pyrimidin-2-amine, as a pale yellow oil.

Examples 15 and 16

Preparation of N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfinyl)ethoxy]pyrimidin-2-amine and N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylthio)ethoxy]pyrimidin-2-amine obtained in Example 14 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Examples 2 and 3 to obtain N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfinyl)ethoxy]pyrimidin-2-amine (compound of Example 15) as a pale yellow oil, and N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfonyl)ethoxy]pyrimidin-2-amine (compound of Example 16) as a pale yellow oil, respectively.

Example 17

Preparation of N-{1-[3,5-bis(trifluoromethyl)phenyl]ethyl}-N-({2-chloro-6-[(cyclopentylmethyl)(ethyl)amino]-3-methylphenyl}methyl)-5-[2-(methylthio)ethoxy]pyrimidin-2-amine By using 2-chloro-6-fluoro-3-methylbenzaldehyde instead of 2-fluoro-5-(trifluoromethyl)benzaldehyde, reactions and treatments were performed in the same manner as those of Step 3 of Example 1 to obtain 2-chloro-6-[(cyclopentylmethyl)(ethyl)amino]-3-methylbenzaldehyde as a yellow oil.

$^1$H-NMR (CDCl$_3$) δ: 1.01 (3H, t, J=6.8 Hz), 1.08-1.20 (2H, m), 1.43-1.73 (6H, m), 2.05 (1H, m), 2.36 (3H, s), 3.00 (2H, d, J=7.6 Hz), 3.11 (2H, q, J=6.8 Hz), 7.03 (1H, d, J=8.3 Hz), 7.31 (1H, d, J=8.3 Hz), 10.25 (1H, s).

By using 2-chloro-6-[(cyclopentylmethyl)(ethyl)amino]-3-methylbenzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-chloro-6-[(cyclopentylmethyl)(ethyl)amino-3-methylphenyl}methyl)-5-[2-(methylthio)ethoxy]pyrimidin-2-amine, as a pale yellow oil.

Example 18

Preparation of N-{1-[3,5-bis(trifluoromethyl)phenyl]ethyl}-N-({2-chloro-6-[(cyclopentylmethyl)(ethyl)amino]-3-methylphenyl}methyl)-5-[2-(methylsulfonyl)ethoxy]pyrimidin-2-amine By using N-{1-[3,5-bis(trifluoromethyl)phenyl]ethyl}-N-({2-chloro-6-[(cyclopentylmethyl)(ethyl)amino]-3-methylphenyl}methyl)-5-[2-(methylthio)ethoxy]pyrimidin-2-amine obtained in Example 17 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-chloro-6-[(cyclopentylmethyl)(ethyl)amino]-3-methylphenyl}methyl)-5-[2-(methylsulfonyl)ethoxy]pyrimidin-2-amine, as a pale yellow oil.

Example 19

Preparation of N-{1-[3,5-bis(trifluoromethyl)phenyl]ethyl}-N-({2-[(cyclopentylmethyl)(ethyl)amino]phenyl}methyl)-5-[2-(methylthio)ethoxy]pyrimidin-2-amine By using 2-fluorobenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]benzaldehyde as a yellow oil.

$^1$H-NMR (CDCl$_3$) δ: 1.04 (3H, t, J=7.1 Hz), 1.11-1.21 (2H, m), 1.42-1.72 (6H, m), 2.07 (1H, m), 3.06 (2H, d, J=7.6 Hz), 3.19 (2H, q, J=7.1 Hz), 7.08 (1H, t, J=8.1 Hz), 7.19 (1H, d, J=8.1 Hz), 7.49 (1H, dt, J=1.6, 8.1 Hz), 7.80 (1H, dd, J=1.6, 8.1 Hz), 10.35 (1H, s).

By using 2-[(cyclopentylmethyl)(ethyl)amino]benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]phenyl}methyl)-5-[2-(methylthio)ethoxy]pyrimidin-2-amine, as a pale yellow oil.

Example 20

Preparation of N-{1-[3,5-bis(trifluoromethyl)phenyl]ethyl}-N-({2-[(cyclopentylmethyl)(ethyl)amino]phenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]phenyl}methyl)-5-[2-(methylthio)ethoxy]pyrimidin-2-amine obtained in Example 19 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the title compound as a pale yellow oil.

Example 21

Preparation of N-{1-[3,5-bis(trifluoromethyl)phenyl]ethyl}-N-({2-[(cyclopentylmethyl)(ethyl)amino]-4,5-difluorophenyl}methyl)-5-[2-(methylthio)ethoxy]pyrimidin-2-amine By using 2,4,5-trifluorobenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-4,5-difluorobenzaldehyde as a yellow oil.

$^1$H-NMR (CDCl$_3$) δ: 1.04 (3H, t, J=7.1 Hz), 1.09-1.23 (2H, m), 1.43-1.71 (6H, m), 2.02 (1H, m), 2.99 (2H, d, J=7.6 Hz), 3.15 (2H, q, J=7.1 Hz), 7.00 (1H, dd, J=6.6, 12.0 Hz), 7.61 (1H, dd, J=9.3, 10.2 Hz), 10.26 (1H, d, J=2.9 Hz).

By using 2-[(cyclopentylmethyl)(ethyl)amino]-4,5-difluorobenzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-4,5-difluorophenyl}methyl)-5-[2-(methylthio)ethoxy]pyrimidin-2-amine, as a pale yellow oil.

Example 22

Preparation of N-{1-[3,5-bis(trifluoromethyl)phenyl]ethyl}-N-({2-[(cyclopentylmethyl)(ethyl)amino]-4,5-difluorophenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-4,5-difluorophenyl}methyl)-5-[2-(methylthio)ethoxy]pyrimidin-2-amine obtained in Example 21 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-4,5-difluorophenyl}methyl)-5-[2-(methylsulfonyl)ethoxy]pyrimidin-2-amine, as a pale brown oil.

Example 23

Preparation of N-{1-[3,5-bis(trifluoromethyl)phenyl]ethyl}-N-({4-chloro-2-[(cyclopentylmethyl)(ethyl)amino]phenyl}methyl)-5-[2-(methylthio)ethoxy]pyrimidin-2-amine By using 4-chloro-2-fluorobenzaldehyde instead of 2-fluoro-5-(trifluoromethyl)benzaldehyde, reactions and treatments were performed in the same manner as those of Step 3 of Example 1 to obtain 4-chloro-2-[(cyclopentylmethyl)(ethyl)amino]benzaldehyde as a yellow oil.

$^1$H-NMR (CDCl$_3$) δ: 1.07 (3H, t, J=7.1 Hz), 1.09-1.20 (2H, m), 1.43-1.73 (6H, m), 2.10 (1H, m), 3.06 (2H, d, J=7.6 Hz), 3.22 (2H, q, J=7.1 Hz), 7.03 (1H, dd, J=2.0, 8.3 Hz), 7.12 (1H, d, J=2.0 Hz), 7.73 (1H, d, J=8.3 Hz), 10.22 (1H, s).

By using 4-chloro-2-[(cyclopentylmethyl)(ethyl)amino]benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({4-chloro-2-[(cyclopentylmethyl)(ethyl)amino]phenyl}methyl)-5-[2-(methylthio)ethoxy]pyrimidin-2-amine, as pale yellow oil.

Example 24

Preparation of N-{1-[3,5-bis(trifluoromethyl)phenyl]ethyl}-N-({4-chloro-2-[(cyclopentylmethyl)(ethyl)amino]phenyl}methyl)-5-[2-(methylsulfonyl)ethoxy]pyrimidin-2-amine By using N-{1-[3,5-bis(trifluoromethyl)phenyl]ethyl}-N-({4-chloro-2-[(cyclopentylmethyl)(ethyl)amino]phenyl}methyl)-5-[2-(methylthio)ethoxy]pyrimidin-2-amine obtained in Example 23 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({4-chloro-2-[(cyclopentylmethyl)(ethyl)amino]phenyl}methyl)-5-[2-(methylsulfonyl)ethoxy]pyrimidin-2-amine, as a pale brown oil.

Example 25

Preparation of N-{1-[3,5-bis(trifluoromethyl)phenyl]ethyl}-N-({2-[(cyclopentylmethyl)(ethyl)amino]-5-fluorophenyl}methyl)-5-[2-(methylthio)ethoxy]pyrimidin-2-amine By using 2,5-difluorobenzaldehyde instead of 2-fluoro-5-(trifluoromethyl)benzaldehyde, reactions and treatments were performed in the same manner as those of Step 3 of Example 1 to obtain 2-[(cyclopentylmethyl)(ethyl)amino]-5-fluorobenzaldehyde as a yellow oil.

$^1$H-NMR (CDCl$_3$) δ: 1.01 (3H, t, J=7.1 Hz), 1.11-121 (2H, m), 1.42-1.69 (6H, m), 1.98 (1H, m), 2.99 (2H, d, J=7.3 Hz), 3.11 (2H, q, J=7.1 Hz), 7.21-7.25 (2H, m), 7.48 (1H, m), 10.40 (1H, d, J=3.2 Hz).

By using 2-[(cyclopentylmethyl)(ethyl)amino]-5-fluorobenzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-5-fluorophenyl}methyl)-5-[2-(methylthio)ethoxy]pyrimidin-2-amine, as a pale brown oil.

Example 26

Preparation of N-{1-[3,5-bis(trifluoromethyl)phenyl]ethyl}-N-({2-[(cyclopentylmethyl)(ethyl)amino]-5-fluorophenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-5-fluorophenyl}methyl)-5-[2-(methylthio)ethoxy]pyrimidin-2-amine obtained in Example 25 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the title compound as a pale yellow oil.

Example 27

Preparation of N-{1-[3,5-bis(trifluoromethyl)phenyl]ethyl}-N-({4-bromo-2-[(cyclopentylmethyl)(ethyl)amino]phenyl}methyl)-5-[2-(methylthio)ethoxy]pyrimidin-2-amine By using 4-bromo-2-fluorobenzaldehyde instead of 2-fluoro-5-(trifluoromethyl)benzaldehyde, reactions and treatments were performed in the same manner as those of Step 3 of Example 1 to obtain 4-bromo-2-[(cyclopentylmethyl)(ethyl)amino]benzaldehyde as a yellow oil.

$^1$H-NMR (CDCl$_3$) δ: 1.04-1.19 (5H, m), 1.49-1.69 (6H, m), 2.10 (1H, m), 3.05 (2H, d, J=7.6 Hz), 3.21 (2H, q, J=7.1 Hz), 7.21 (1H, d, J=8.4 Hz), 7.28 (1H, s), 7.64 (1H, d, J=8.4 Hz), 10.22 (1H, s).

By using 4-bromo-2-[(cyclopentylmethyl)(ethyl)amino]benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({4-bromo-2-[(cyclopentylmethyl)(ethyl)amino]phenyl}methyl)-5-[2-(methylthio)ethoxy]pyrimidin-2-amine, as a pale yellow oil.

Example 28

Preparation of N-{1-[3,5-bis(trifluoromethyl)phenyl]ethyl}-N-({4-bromo-2-[(cyclopentylmethyl)(ethyl)amino]phenyl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-4-bromophenyl}methyl)-5-[2-(methylthio)ethoxy]pyrimidin-2-amine obtained in Example 27 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({4-bromo-2-[(cyclopentylmethyl)(ethyl)amino]phenyl}methyl)-5-[2-(methylsulfonyl)ethoxy]pyrimidin-2-amine, as a pale yellow oil.

Example 29

Preparation of N-{1-[3,5-bis(trifluoromethyl)phenyl]ethyl}-N-({5-bromo-2-[(cyclopentylmethyl)(ethyl)amino]phenyl}methyl)-5-[2-(methylthio)ethoxy]pyrimidin-2-amine By using 5-bromo-2-fluorobenzaldehyde instead of 2-fluoro-5-(trifluoromethyl)benzaldehyde, reactions and treatments were performed in the same manner as those of Step 3 of Example 1 to obtain 5-bromo-2-[(cyclopentylmethyl)(ethyl)amino]benzaldehyde as a yellow oil.

$^1$H-NMR (CDCl$_3$) δ: 1.04-1.19 (5H, m), 1.49-1.69 (6H, m), 2.04 (1H, m), 3.03 (2H, d, J=7.6 Hz), 3.19 (2H, q, J=7.1 Hz), 7.07 (1H, d, J=8.6 Hz), 7.56 (1H, d, J=8.6 Hz), 7.89 (1H, s), 10.23 (1H, s).

By using 5-bromo-2-[(cyclopentylmethyl)(ethyl)amino]benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-({5-bromo-2-[(cyclopentylmethyl)(ethyl)amino]phenyl}methyl)-5-[2-(methylthio)ethoxy]pyrimidin-2-amine, as a pale yellow oil.

Example 30

Preparation of N-{1-[3,5-bis(trifluoromethyl)phenyl]ethyl}-N-({5-bromo-2-[(cyclopentylmethyl)(ethyl)amino]phenyl}methyl)-5-[2-(methylsulfonyl)ethoxy]pyrimidin-2-amine By using N-{1-[3,5-bis(trifluoromethyl)phenyl]ethyl}-N-({5-bromo-2-[(cyclopentylmethyl)(ethyl)amino]phenyl}methyl)-5-[2-(methylthio)ethoxy]pyrimidin-2-amine obtained in Example 29 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({5-bromo-2-[(cyclopentylmethyl)(ethyl)amino]phenyl}methyl)-5-[2-(methylsulfonyl)ethoxy]pyrimidin-2-amine, as a pale yellow oil.

Example 31

Preparation of 3-{1-[({2-[(cyclopentylmethyl)(ethyl)amino]-5-trifluoromethylphenyl}methyl){5-[2-(methylthio)ethoxy]pyrimidin-2-yl}amino]ethyl}-5-(trifluoromethyl)benzonitrile 3-(Hydroxymethyl)-5-(trifluoromethyl)benzonitrile (2.70 g, 13.4 mmol) synthesized by the method described in Japanese Patent Unexamined Publication (Kokai) No. 2003-221376 was dissolved in acetone (30 mL), to the solution was added 2 M Jones reagent (26.8 mL, 53.6 mmol), and the mixture was stirred for 12 hours. The reaction mixture was diluted with water (15 mL), and then extracted with ether. The organic layers were combined, and inversely extracted with 2 M aqueous sodium hydroxide, and then the aqueous layer was neutralized with 1 M hydrochloric acid, and extracted with chloroform. The organic layer was washed with saturated brine, dried over anhydrous sodium sulfate, and concentrated under reduced pressure to obtain 3-cyano-5-(trifluoromethyl)benzoic acid (2.44 g, 85%) as a colorless solid.

$^1$H-NMR (CDCl$_3$) δ: 8.18 (1H, s), 8.60 (2H, s).

To a solution of 3-cyano-5-(trifluoromethyl)benzoic acid (200 mg, 0.93 mmol) in tetrahydrofuran (2 mL) stirred on an ice bath was added N,O-dimethylhydroxyamine hydrochloride (145 mg, 1.49 mmol), N,N-diisopropylethylamine (470 mg, 3.64 mmol) and diethyl cyanophosphate (DEPC, 227 mg, 1.39 mmol), and the mixture was stirred at room temperature for 1 hour. The reaction mixture was concentrated under reduced pressure, and the resulting residue was added with 1 M hydrochloric acid (0.5 mL), and extracted with ethyl acetate. The organic layer was washed with saturated brine, then dried anhydrous sodium sulfate, and concentrated under reduced pressure, and the resulting residue was purified by silica gel column chromatography (hexane:ethyl acetate=3:1) to obtain 3-cyano-N-methoxy-N-methyl-5-(trifluoromethyl)benzamide (196 mg, 82%) as a pale yellow solid.

$^1$H-NMR (CDCl$_3$) δ: 3.42 (3H, s), 3.56 (3H, s), 8.00 (1H, s), 8.22 (2H, s).

To a solution of 3-cyano-N-methoxy-N-methyl-5-(trifluoromethyl)benzamide (196 mg, 0.76 mmol) in anhydrous tetrahydrofuran (2 mL) stirred on an ice bath was added methylmagnesium bromide (0.96 M solution in ether, 0.95 mL, 0.91 mmol), and the mixture was stirred at room temperature for 15 minutes. The reaction mixture was added with 1 M hydrochloric acid, and extracted with ethyl acetate, and then the organic layer was washed with saturated brine, dried over anhydrous sodium sulfate, and then concentrated under reduced pressure to obtain 3-acetyl-5-(trifluoromethyl)benzonitrile (162 mg, 100%) as a pale yellow oil.

$^1$H-NMR (CDCl$_3$) δ: 2.70 (3H, s), 8.10 (1H, s), 8.41 (2H, s).

By using 3-acetyl-5-(trifluoromethyl)benzonitrile instead of 3,5-bis(trifluoromethyl)acetophenone, reactions and treatments were performed in the same manner as those of Step 2 of Example 1 to obtain 3-(1-bromoethyl)-5-(trifluoromethyl)benzonitrile as a colorless oil.

$^1$H-NMR (CDCl$_3$) δ: 2.07 (3H, d, J=7.1 Hz), 5.57 (1H, m), 7.90 (1H, s), 7.92 (2H, s).

By using 3-(1-bromoethyl)-5-(trifluoromethyl)benzonitrile instead of 1-bromo-1-[3,5-bis(trifluoromethyl)phenyl]ethane, reactions and treatments were performed in the same manner as those of Step 4 of Example 1 to obtain the target compound, 3-{1-[({2-[(cyclopentylmethyl)(ethyl)amino]-5-trifluoromethylphenyl}methyl){5-[2-(methylthio)ethoxy]pyrimidin-2-yl}amino]ethyl}-5-(trifluoromethyl)benzonitrile, as a pale yellow oil.

Example 32

Preparation of 3-{1-[({2-[(cyclopentylmethyl)(ethyl)amino]-5-trifluoromethylphenyl}methyl){5-[2-(methylsulfonyl)ethoxy]pyrimidin-2-yl}amino]ethyl}-5-(trifluoromethyl)benzonitrile By using 3-{1-[({2-[(cyclopentylmethyl)(ethyl)amino]-5-trifluoromethylphenyl}methyl) {5-[2-(methylthio)ethoxy]pyrimidin-2-yl}amino]ethyl}-5-(trifluoromethyl)benzonitrile obtained in Example 31 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, 3-{1-[({2-[(cyclopentylmethyl)(ethyl)amino]-5-trifluoromethylphenyl}methyl){5-[2-(methylsulfonyl)ethoxy]pyrimidin-2-yl}amino]ethyl}-5-(trifluoromethyl)benzonitrile, as a pale yellow oil.

Example 33

Preparation of N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylthio)ethoxy]pyrimidin-2-amine To a solution of 3,5-bis(trifluoromethyl)benzaldehyde (300 mg, 1.24 mmol) in anhydrous tetrahydrofuran (3 mL) stirred on an ice bath was added ethylmagnesium bromide (1.00 M solution in anhydrous tetrahydrofuran, 1.86 mL, 1.86 mmol), and the mixture was stirred at the same temperature for 30 minutes. The reaction mixture was added with 1 M hydrochloric acid on an ice bath until pH became 7 or lower, and then extracted with ethyl acetate. The organic layer was washed with saturated brine, dried over anhydrous sodium sulfate, and then concentrated under reduced pressure, and the resulting residue was purified by silica gel column chromatography (hexane:ethyl acetate=10:1) to obtain 1-[3,5-bis(trifluoromethyl)phenyl]-1-propanol (165 mg, 49%) as a colorless solid.

$^1$H-NMR (CDCl$_3$) δ: 0.97 (3H, t, J=7.4 Hz), 1.77-1.84 (2H, m), 2.01 (1H, d, J=3.6 Hz), 4.79 (1H, m), 7.79 (1H, s), 7.82 (2H, s).

By using 1-[3,5-bis(trifluoromethyl)phenyl]-1-propanol instead of 1-[3,5-bis(trifluoromethyl)phenyl]ethanol, reactions and treatments were performed in the same manner as those of Step 2 of Example 1 to obtain 1-bromo-1-[3,5-bis(trifluoromethyl)phenyl]propane as a pale yellow oil.

$^1$H-NMR (CDCl$_3$) δ: 1.05 (3H, t, J=7.3 Hz), 2.14-2.34 (2H, m), 4.90 (1H, m), 7.80 (1H, s), 7.83 (2H, s).

By using 1-bromo-1-[3,5-bis(trifluoromethyl)phenyl]propane instead of 1-bromo-1-[3,5-bis(trifluoromethyl)phenyl]ethane, reactions and treatments were performed in the same manner as those of Step 4 of Example 1 to obtain the target compound, N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylthio)ethoxy]pyrimidin-2-amine, as a pale yellow oil Example 34

Preparation of N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylsulfonyl)ethoxy]pyrimidin-2-amine By using N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylthio)ethoxy]pyrimidin-2-amine obtained in Example 33 instead of N-{-1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylsulfonyl)ethoxy]pyrimidin-2-amine, as a pale yellow oil.

Example 35

Preparation of N-{1-[3,5-bis(trifluoromethyl)phenyl]ethyl}-N-{[2-(piperidino)-5-(trifluoromethyl)phenyl]methyl}-5-[2-(methylthio)ethoxy]pyrimidin-2-amine By using piperidine instead of N-(cyclopentylmethyl)-N-ethylamine, reactions and treatments were performed in the same manner as those of Step 3 of Example 1 to obtain 2-(piperidino)-5-(trifluoromethyl)benzaldehyde as a yellow oil.

$^1$H-NMR (CDCl$_3$) δ: 1.57-1.69 (2H, m), 1.70-1.82 (4H, m), 3.08-3.18 (4H, m), 7.14 (1H, d, J=8.5 Hz), 7.69 (1H, dd, J=2.3, 8.5 Hz), 8.03 (1H, d, J=2.3 Hz), 10.20 (1H, s).

By using 2-(piperidino)-5-(trifluoromethyl)benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-{[2-(piperidino)-5-(trifluoromethyl)phenyl]methyl}-5-[2-(methylthio)ethoxy]pyrimidin-2-amine as a yellow oil.

Example 36

Preparation of N-{1-[3,5-bis(trifluoromethyl)phenyl]ethyl}-N-{[2-(piperidino)-5-(trifluoromethyl)phenyl]methyl}-5-[2-(methylsulfonyl)ethoxy]pyrimidin-2-amine By using N-{1-[3,5-bis(trifluoromethyl)phenyl]ethyl}-N-{[2-(piperidino)-5-(trifluoromethyl)phenyl]methyl}-5-[2-(methylthio)ethoxy]pyrimidin-2-amine obtained in Example 35 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-{[2-(piperidino)-5-(trifluoromethyl)phenyl]methyl}-5-[2-(methylsulfonyl)ethoxy]pyrimidin-2-amine, as a colorless amorphous.

Example 37

Preparation of N-{1-[3,5-bis(trifluoromethyl)phenyl]ethyl}-N-{[2-(morpholino)-5-(trifluoromethyl)phenyl]methyl}-5-[2-(methylthio)ethoxy]pyrimidin-2-amine By using morpholine instead of N-(cyclopentylmethyl)-N-ethylamine, reactions and treatments were performed in the same manner as those of Step 3 of Example 1 to obtain 2-(morpholino)-5-(trifluoromethyl)benzaldehyde as a yellow oil.

$^1$H-NMR (CDCl$_3$) δ: 3.12-3.20 (4H, m), 3.87-3.95 (4H, m), 7.17 (1H, d, J=8.6 Hz), 7.75 (1H, dd, J=2.0, 8.6 Hz), 8.06 (1H, d, J=2.0 Hz), 10.25 (1H, s).

By using 2-(morpholino)-5-(trifluoromethyl)benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-{[2-(morpholino)-5-(trifluoromethyl)phenyl]methyl}-5-[2-(methylthio)ethoxy]pyrimidin-2-amine as a brown oil.

Example 38

Preparation of N-{1-[3,5-bis(trifluoromethyl)phenyl]ethyl}-N-{[2-(morpholino)-5-(trifluoromethyl)phenyl]methyl}-5-[2-(methylsulfonyl)ethoxy]pyrimidin-2-amine By using N-{1-[3,5-bis(trifluoromethyl)phenyl]ethyl}-N-{[2-(morpholino)-5-(trifluoromethyl)phenyl]methyl}-5-[2-(methylthio)ethoxy]pyrimidin-2-amine obtained in Example 37 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-{[2-(morpholino)-5-(trifluoromethyl)phenyl]methyl}-5-[2-(methylsulfonyl)ethoxy]pyrimidin-2-amine, as pale yellow crystalline powder.

Example 39

Preparation of N-{1-[3,5-bis(trifluoromethyl)phenyl]ethyl}-N-{[2-(4-methylpiperidino)-5-(trifluoromethyl)phenyl]methyl}-5-[2-(methylthio)ethoxy]pyrimidin-2-amine By using 4-methylpiperidine instead of N-(cyclopentylmethyl)-N-ethylamine, reactions and treatments were performed in the same manner as those of Step 3 of Example 1 to obtain 2-(4-methylpiperidino)-5-(trifluoromethyl)benzaldehyde as a yellow oil.

$^1$H-NMR (CDCl$_3$) δ: 1.03 (3H, d, J=6.3 Hz), 1.36-1.51 (2H, m), 1.59 (1H, m), 1.70-1.84 (2H, m), 2.88-3.02 (2H, m), 3.28-3.42 (2H, m), 7.14 (1H, d, J=8.5 Hz), 7.68 (1H, dd, J=2.2, 8.5 Hz), 8.03 (1H, d, J=2.2 Hz), 10.18 (1H, s).

By using 2-(4-methylpiperidino)-5-(trifluoromethyl)benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-{[2-(4-methylpiperidino)-5-(trifluoromethyl)phenyl]methyl}-5-[2-(methylsulfonyl)ethoxy]pyrimidin-2-amine as a yellow oil.

Example 40

Preparation of N-{1-[3,5-bis(trifluoromethyl)phenyl]ethyl}-N-{[2-(4-methylpiperidino)-5-(trifluoromethyl)phenyl]methyl}-5-[2-(methylsulfonyl)ethoxy]pyrimidin-2-amine By using N-{1-[3,5-bis(trifluoromethyl)phenyl]ethyl}-N-{[2-(4-methylpiperidino)-5-(trifluoromethyl)phenyl]methyl}-5-[2-(methylthio)ethoxy]pyrimidin-2-amine obtained in Example 39 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-{[2-(4-methylpiperidino)-5-(trifluoromethyl)phenyl]methyl}-5-[2-(methylsulfonyl)ethoxy]pyrimidin-2-amine, as a colorless amorphous.

Example 41

Preparation of N-{1-[3,5-bis(trifluoromethyl)phenyl]ethyl}-N-{[2-(cis-2,6-dimethylmorpholino)-5-(trifluoromethyl)phenyl]methyl}-5-[2-(methylthio)ethoxy]pyrimidin-2-amine By using cis-2,6-dimethylmorpholine instead of N-(cyclopentylmethyl)-N-ethylamine, reactions and treatments were performed in the same manner as those of Step 3 of Example 1 to obtain 2-(cis-2,6-dimethylmorpholino)-5-(trifluoromethyl)benzaldehyde as a yellow oil.

$^1$H-NMR (CDCl$_3$) δ: 1.24 (6H, d, J=6.4 Hz), 2.66-2.77 (2H, m), 3.08-3.20 (2H, m), 3.84-3.98 (2H, m), 7.14 (1H, d, J=8.5 Hz), 7.73 (1H, dd, J=1.7, 8.5 Hz), 8.05 (1H, d, J=1.7 Hz), 10.22 (1H, s).

By using 2-(cis-2,6-dimethylmorpholino)-5-(trifluoromethyl)benzaldehyde instead of 2-[(cyclopentylmethyl)(ethyl)amino]-5-(trifluoromethyl)benzaldehyde, reactions and treatments were performed in the same manner as those of Step 4 of Example 1 to obtain the target compound, N-{1-[3,5-bis(trifluoromethyl)phenyl]ethyl}-N-{[2-(cis-2,6-dimethylmorpholino)-5-(trifluoromethyl)phenyl]methyl}-5-[2-(methylthio)ethoxy]pyrimidin-2-amine, as a yellow oil.

Example 42

Preparation of N-{1-[3,5-bis(trifluoromethyl)phenyl]ethyl}-N-{[2-(cis-2,6-dimethylmorpholino)-5-(trifluoromethyl)phenyl]methyl}-5-[2-(methylsulfonyl)ethoxy]pyrimidin-2-amine By using N-{1-[3,5-bis(trifluoromethyl)phenyl]ethyl}-N-{[2-(cis-2,6-dimethylmorpholino)-5-(trifluoromethyl)phenyl]methyl}-5-[2-(methylthio)ethoxy]pyrimidin-2-amine obtained in Example 41 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-{[2-(cis-2,6-dimethylmorpholino)-5-(trifluoromethyl)phenyl]methyl}-5-[2-(methylsulfonyl)ethoxy]pyrimidin-2-amine, as a colorless amorphous.

Examples 43 and 44

Preparation of ethyl trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetate and trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid By using ethyl trans-{4-[(ethylamino)methyl]cyclohexyl}acetate synthesized by the method described in International Patent Publication WO2004/020393 instead of N-(cyclopentylmethyl)-N-ethylamine, reactions and treatments were performed in the same manner as those of Step 3 of Example 1 to obtain ethyl trans-[4-({[2-(formyl)-4-(trifluoromethyl)phenyl](ethyl)amino}methyl)cyclohexyl]acetate as a yellow oil.

$^1$H-NMR (CDCl$_3$) δ: 0.86-1.01 (4H, m), 1.11 (3H, t, J=7.1 Hz), 1.24 (3H, t, J=7.1 Hz), 1.54 (1H, m), 1.64-1.85 (5H, m), 2.15 (2H, d, J=6.8 Hz), 3.09 (2H, d, J=7.1 Hz), 3.31 (2H, q, J=7.1 Hz), 4.11 (2H, q, J=7.1 Hz), 7.15 (1H, d, J=8.8 Hz), 7.64 (1H, dd, J=2.0, 8.8 Hz), 8.03 (1H, d, J=2.0 Hz), 10.17 (1H, s).

By using ethyl trans-[4-({[2-(formyl)-4-(trifluoromethyl)phenyl](ethyl)amino}methyl)cyclohexyl]acetate instead of 2-[(cyclopentylmethyl)(ethyl)amino]-5-(trifluoromethyl)benzaldehyde, the reaction with 5-[2-(methylthio)ethoxy]pyrimidin-2-amine and treatments were performed in the same manner as those of Step 4 of Example 1 to obtain ethyl trans-{4-[({2-[({5-[2-(methylthio)ethoxy]pyrimidin-2-yl}amino)methyl]-4-(trifluoromethyl)phenyl}(ethyl)amino)methyl]cyclohexyl}acetate as a pale yellow oil.

$^1$H-NMR (CDCl$_3$) δ: 0.88-0.96 (4H, m), 1.02 (3H, t, J=7.1 Hz), 1.24 (3H, t, J=7.1 Hz), 1.40 (1H, m), 1.60-1.85 (5H, m), 2.15 (2H, d, J=6.6 Hz), 2.20 (3H, s), 2.84-2.87 (4H, m), 3.00 (2H, q, J=7.1 Hz), 4.11 (2H, q, J=7.1 Hz), 4.12 (2H, t, J=6.7 Hz), 4.67 (2H, d, J=5.9 Hz), 5.48 (1H, t, J=5.9 Hz), 7.18 (1H, d, J=8.3 Hz), 7.44 (1H, dd, J=1.4, 8.3 Hz), 7.62 (1H, d, J=1.4 Hz), 8.07 (2H, s).

To a stirred solution of ethyl trans-{4-[({2-[({5-[2-(methylthio)ethoxy]pyrimidin-2-yl}amino)methyl]-4-(trifluoromethyl)phenyl}(ethyl)amino)methyl]cyclohexyl}acetate (10.2 mg, 0.018 mmol) in tetrahydrofuran (0.3 mL) under ice cooling was added sodium hydride (50% in oil, 3.4 mg, 0.072 mmol), and the mixture was stirred at room temperature for 30 minutes. After cooling to −78° C., to the reaction mixture was added a solution of 1-bromo-1-[3,5-bis(trifluoromethyl)phenyl]ethane (6.9 mg, 0.021 mmol) in N,N-dimethylformamide (0.3 mL), and the mixture was stirred for 14 hours with warming to room temperature. The reaction mixture was added with water, and extracted with ethyl acetate, and the organic layer was washed twice with water. The organic layer was washed with saturated brine, dried over anhydrous sodium sulfate, and then concentrated under reduced pressure, and the resulting residue was purified by silica gel column chromatography (hexane:ethyl acetate=20:1→chloroform:methanol=20:1) to obtain ethyl trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetate (compound of Example 43, 1.8 mg, 12%) as a pale yellow oil, and trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid (compound of Example 44, 3.2 mg, 23%) as a pale yellow oil.

Example 45

Preparation of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid By using trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid obtained in Example 44 instead of N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, reactions and treatments were performed in the same manner as those of Example 3 to obtain the target compound, trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, as a pale yellow oil.

Example 46

Preparation of N-({2-[bis(cyclopropylmethyl)amino]-3,5-difluorophenyl}methyl)-N-{1-[3,5-bis(trifluoromethyl)phenyl]ethyl}-5-[2-(methylthio)ethoxy]pyrimidin-2-amine By using 2,3,5-trifluorobenzaldehyde instead of 2-fluoro-5-(trifluoromethyl)benzaldehyde, and N,N-bis(cyclopropylmethyl)amine synthesized by the method described in International Patent Publication WO2006/073973 instead of N-(cyclopentylmethyl)-N-ethylamine, reactions and treatments were performed in the same manner as those of Step 3 of Example 1 to obtain 2-[bis(cyclopropylmethyl)amino]-3,5-difluorobenzaldehyde as a yellow oil.

$^1$H-NMR (CDCl$_3$) δ: −0.08-0.07 (4H, m), 0.31-0.39 (4H, m), 0.68-0.80 (2H, m), 2.97 (2H, d, J=6.8 Hz), 2.98 (2H, d, J=7.1 Hz), 7.04 (1H, ddd, J=2.9, 8.0, 11.5 Hz), 7.35 (1H, ddd, J=1.5, 2.9, 8.0 Hz), 10.69 (1H, d, J=3.4 Hz).

By using 2-[bis(cyclopropylmethyl)amino]-3,5-difluorobenzaldehyde instead of 2-[(cyclopentylmethyl)(ethyl)

amino]-5-(trifluoromethyl)benzaldehyde, reactions and treatments were performed in the same manner as those of Step 4 of Example 1 to obtain the target compound, N-({2-[bis(cyclopropylmethyl)amino]-3,5-difluorophenyl}methyl)-N-{1-[3,5-bis(trifluoromethyl)phenyl]ethyl}-5-[2-(methylthio)ethoxy]pyrimidin-2-amine, as a pale yellow oil.

Example 47

Preparation of N-({2-[bis(cyclopropylmethyl)amino]-3,5-difluorophenyl}methyl)-N-{1-[3,5-bis(trifluoromethyl)phenyl]ethyl}-5-[2-(methylsulfonyl)ethoxy]pyrimidin-2-amine By using N-({2-[bis(cyclopropylmethyl)amino]-3,5-difluorophenyl}methyl)-N-{1-[3,5-bis(trifluoromethyl)phenyl]ethyl}-5-[2-(methylthio)ethoxy]pyrimidin-2-amine obtained in Example 46 instead of N-{1-[3,5-bis(trifluoromethyl)phenyl]ethyl}-N-({2-[(cyclopentylmethyl)(ethyl)amino]-5-(trifluoromethylphenyl}methyl)-5-[2-(methylthio)ethoxy]pyrimidin-2-amine, reactions and treatments were performed in the same manner as those of Example 3 to obtain the target compound, N-({2-[bis(cyclopropylmethyl)amino]-3,5-difluorophenyl}methyl)-N-{1-[3,5-bis(trifluoromethyl)phenyl]ethyl}-5-[2-(methylsulfonyl)ethoxy]pyrimidin-2-amine, as a pale yellow oil.

The compounds obtained in the aforementioned examples are shown in Table 1.

TABLE 1-1

| Example | Chemical formula | Physicochemical properties |
| --- | --- | --- |
| 1 | | $^1$H-NMR (CDCl$_3$) δ: 0.96 (3H, t, J = 7.1 Hz), 1.03-1.17 (2 H, m), 1.41-1.67 (9 H, m), 1.99 (1 H, m), 2.21 (3 H, s), 2.80 (1 H, dd, J = 8.0, 12.9 Hz), 2.85-2.95 (5 H, m), 4.16 (2 H, t, J = 6.6 Hz), 4.63 (1 H, d, J = 17.1 Hz), 4.84 (1 H, d, J = 17.1 Hz), 6.22 (1 H, q, J = 6.8 Hz), 7.13 (1 H, d, J = 8.1 Hz), 7.23 (1 H, s), 7.37 (1 H, d, J = 8.1 Hz), 7.70 (1 H, s), 7.76 (2 H, s), 8.15 (2 H, s). |
| 2 | | IR (ATR) cm$^{-1}$: 2954, 1613, 1548, 1477, 1278, 1134. $^1$H-NMR (CDCl$_3$) δ: 0.96 (3 H, t, J = 7.0 Hz), 1.05-1.20 (2 H, m), 1.40-1.70 (9 H, m), 1.99 (1 H, m), 2.71 (3 H, s), 2.81 (1 H, dd, J = 8.0, 12.9 Hz), 2.88-2.97 (3 H, m), 3.05 (1 H, td, J = 3.7, 13.7 Hz), 3.19 (1 H, ddd, J = 5.1, 8.3, 13.7 Hz), 4.38-4.50 (2 H, m), 4.64 (1 H, d, J = 17.1 Hz), 4.84 (1 H, d, J = 17.1 Hz), 6.22 (1 H, q, J = 7.1 Hz), 7.13 (1 H, d, J = 7.8 Hz), 7.22 (1 H, s), 7.38 (1 H, d, J = 7.8 Hz), 7.71 (1 H, s), 7.75 (2 H, s), 8.17 (2 H, s). |
| 3 | | IR (ATR) cm$^{-1}$: 2949, 1614, 1550, 1477, 1277, 1131. $^1$H-NMR (CDCl$_3$) δ: 0.96 (3 H, t, J = 7.1 Hz), 1.05-1.19 (2 H, m), 1.40-1.68 (9 H, m), 1.99 (1 H, m), 2.81 (1 H, dd, J =8.0, 12.9 Hz), 2.88-2.97 (3 H, m), 3.09 (3 H, s), 3.45 (2 H, t, J =5.4 Hz), 4.44 (2 H, t, J =5.4 Hz), 4.65 (1 H, d, J = 17.3 Hz), 4.85 (1 H, d, J = 17.3 Hz), 6.21 (1 H, q, J = 7.5 Hz), 7.14 (1 H, d, J =8.3 Hz), 7.20 (1 H, s), 7.38 (1 H, d, J = 8.3 Hz), 7.71 (1 H, s), 7.75 (2 H, s), 8.16 (2 H, s). |

TABLE 1-1-continued

| Example | Chemical formula | Physicochemical properties |
|---|---|---|
| 4 | 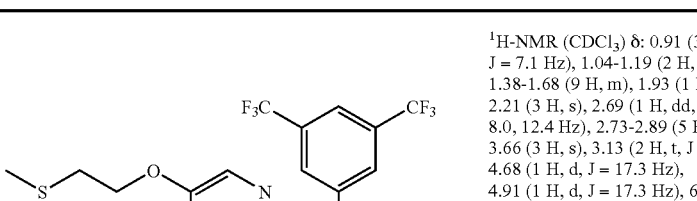 | $^1$H-NMR (CDCl$_3$) δ: 0.91 (3 H, t, J = 7.1 Hz), 1.04-1.19 (2 H, m), 1.38-1.68 (9 H, m), 1.93 (1 H, m), 2.21 (3 H, s), 2.69 (1 H, dd, J = 8.0, 12.4 Hz), 2.73-2.89 (5 H, m), 3.66 (3 H, s), 3.13 (2 H, t, J = 6.8 Hz), 4.68 (1 H, d, J = 17.3 Hz), 4.91 (1 H, d, J = 17.3 Hz), 6.15 (1 H, q, J = 7.1 Hz), 6.91 (1 H, d, J = 2.9 Hz), 6.70 (1 H, dd, J = 2.9, 8.8 Hz), 7.05 (1 H, d, J = 8.8 Hz), 7.70 (1 H, s), 7.70 (2 H, s), 8.11 (2 H, s). |

TABLE 1-2

| Example | Chemical formula | Physicochemical properties |
|---|---|---|
| 5 | 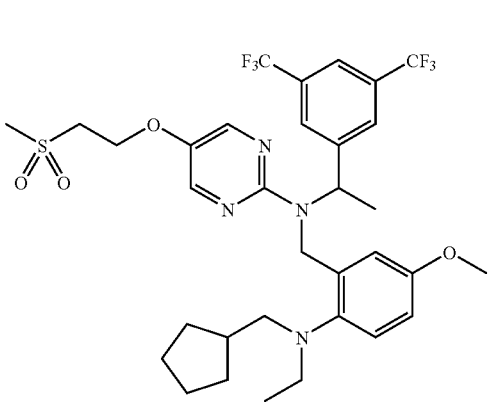 | IR (ATR) cm$^{-1}$: 2937, 1607, 1548, 1478, 1277, 1132. $^1$H-NMR (CDCl$_3$) δ: 0.91 (3 H, t, J = 7.1 Hz), 1.04-1.19 (2 H, m), 1.38-1.68 (9 H, m), 1.93 (1 H, m), 2.69 (1H, dd, J = 7.8, 12.5 Hz), 2.77 (1 H, dd, J = 7.01, 12.5 Hz), 2.82 (2 H, q, J = 7.1 Hz), 3.07 (3 H, s), 3.43 (2 H, t, J = 5.4 Hz), 3.67 (3 H, s), 4.41 (2 H, t, J = 5.4 Hz), 4.69 (1 H, d, J = 17.4 Hz), 4.93 (1 H, d, J = 17.4 Hz), 6.13 (1 H, q, J = 7.1 Hz), 6.59 (1 H, d, J = 2.9 Hz), 6.70 (1 H, dd, J = 2.9, 8.8 Hz), 7.06 (1 H, d, J = 8.8 Hz), 7.71 (1 H, s), 7.76 (2 H, s), 8.12 (2 H, s). |
| 6 | 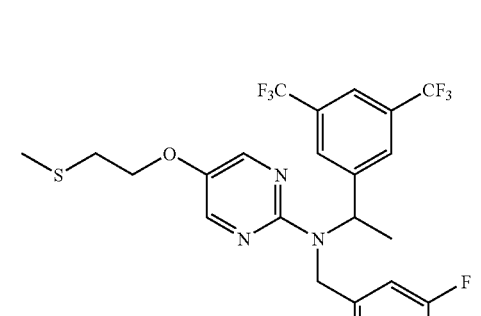 | $^1$H-NMR (CDCl$_3$) δ: 0.88-1.12 (5 H, m), 1.43-1.59 (9 H, m), 1.92 (1 H, m), 2.21 (3 H, s), 2.64-3.04 (6 H, m), 4.14 (2 H, t, J = 6.6 Hz), 4.63 (1 H, d, J = 16.8 Hz), 4.86 (1 H, d, J = 16.8 Hz), 6.26 (1 H, q, J = 7.0 Hz), 6.51 (1 H, d, J = 9.3 Hz), 6.60 (1 H, t, J = 9.9 Hz), 7.71 (1 H, s), 7.76 (2 H, s), 8.11 (2 H, s). |

TABLE 1-2-continued

| Example | Chemical formula | Physicochemical properties |
|---|---|---|
| 7 | | IR (ATR) cm$^{-1}$: 2950, 1606, 1550, 1476, 1277, 1133.<br>$^1$H-NMR (CDCl$_3$) δ: 0.88-1.14 (5 H, m), 1.41-1.62 (9 H, m), 1.92 (1 H, m), 2.71-3.00 (4 H, m), 3.07 (3 H, s), 3.44 (2 H, t, J = 5.4 Hz), 4.43 (2 H, t, J = 5.4 Hz), 4.65 (1 H, d, J = 17.8 Hz), 4.88 (1 H, d, J = 17.8 Hz), 6.26 (1 H, q, J = 6.9 Hz), 6.48 (1 H, d, J = 9.0 Hz), 6.61 (1 H, t, J = 10.0 Hz), 7.73 (1 H, s), 7.76 (2 H, s), 8.14 (2 H, s). |
| 8 | | $^1$H-NMR (CDCl$_3$) δ: 0.92 (3 H, t, J = 7.1 Hz), 1.06-1.20 (2 H, m), 1.40-1.80 (9 H, m), 1.96 (1 H, m) 2.17 (3 H, s), 2.21 (3 H, s), 2.69-2.88 (6 H, m), 4.14 (2 H, t, J = 6.8 Hz), 4.70 (1 H, d, J = 17.1 Hz), 4.90 (1 H, d, J = 17.1 Hz), 6.09 (1 H, q, J = 7.1 Hz), 6.81 (1 H, s), 6.96 (1 H, d, J = 8.0 Hz), 7.00 (1 H, d, J = 8.0 Hz), 7.69 (1 H, s), 7.76 (2 H, s), 8.13 (2 H, s). |

TABLE 1-3

| Example | Chemical formula | Physicochemical properties |
|---|---|---|
| 9 | | IR (ATR) cm$^{-1}$: 2949, 1606, 1548, 1478, 1277, 1173, 1132.<br>$^1$H-NMR (CDCl$_3$) δ: 0.93 (3 H, t, J = 7.1 Hz), 1.10-1.20 (2 H, m), 1.35-1.71 (9 H, m), 1.96 (1 H, m), 2.18 (3 H, s), 2.69-2.92 (4 H, m), 3.08 (3 H, s), 3.43 (2 H, t, J = 5.1 Hz), 4.42 (2 H, t, J = 5.1 Hz), 4.72 (1 H, t, J = 17.1 Hz), 4.92 (1 H, d, J = 17.1 Hz), 6.07 (1 H, q, J = 7.1 Hz), 6.79 (1 H, s), 6.95 (1 H, d, J = 7.9 Hz), 7.01 (1 H, d, J = 7.9 Hz), 7.70 (1 H, s), 7.76 (2 H, s), 8.14 (2 H, s). |
| 10 | | $^1$H-NMR (CDCl$_3$) δ: 0.95 (3 H, t, J = 7.1 Hz), 1.08-1.17 (2 H, m), 1.46-1.64 (9 H, m), 1.99 (1 H, m), 2.21 (3 H, s), 2.73 (1 H, m), 2.81-2.90 (5 H, m), 4.16 (2 H, t, J = 6.7 Hz), 4.59 (1 H, d, J = 16.8 Hz), 4.83 (1 H, d, J = 16.8 Hz), 6.15 (1 H, q, J = 7.1 Hz), 6.61 (1 H, dt, J = 2.4, 8.3 Hz), 6.79 (1 H, dd, J = 2.4, 11.0 Hz), 6.97 (1 H, t, J = 8.3 Hz), 7.71 (1 H, s), 7.76 (2 H, s), 8.14 (2 H, s). |

TABLE 1-3-continued

| Example | Chemical formula | Physicochemical properties |
|---|---|---|
| 11 | | IR (ATR) cm$^{-1}$: 2953, 1608, 1548, 1480, 1278, 1133.<br>$^1$H-NMR (CDCl$_3$) δ: 0.95 (3 H, t, J = 7.0 Hz), 1.08-1.17 (2 H, m), 1.44-1.64 (9 H, m), 1.99 (1 H, m), 2.74 (1 H, m), 2.81-2.90 (3 H, m), 3.08 (3 H, s), 3.44 (2 H, t, J = 5.2 Hz), 4.43 (2 H, t, J = 5.2 Hz), 4.61 (1 H, d, J = 16.8 Hz), 4.85 (1 H, d, J = 16.8 Hz), 6.14 (1 H, q, J = 7.1 Hz), 6.62 (1 H, dt, J = 2.4, 8.3 Hz), 6.80 (1 H, dd, J = 2.4, 11.0 Hz), 6.95 (1 H, t, J = 8.3 Hz), 7.71 (1 H, s), 7.75 (2 H, s), 8.15 (2 H, s). |
| 12 | | $^1$H-NMR (CDCl$_3$) δ: 0.94 (3 H, t, J = 7.1 Hz), 1.10-1.20 (2 H, m), 1.44-1.66 (9 H, m), 1.96 (1 H, m), 2.21 (3 H, s), 2.71-2.88 (6 H, m), 3.75 (3 H, s), 4.13 (2 H, t, J = 6.8 Hz), 4.60 (1 H, d, J = 17.1 Hz), 4.85 (1 H, d, J = 17.1 Hz), 6.08 (1 H, q, J = 7.1 Hz), 6.48 (1 H, dd, J = 2.4, 8.5 Hz), 6.66 (1 H, d, J = 8.5 Hz), 6.94 (1 H, d, J = 2.4 Hz), 7.69 (1 H, s), 7.75 (2 H, s), 8.12 (2 H, s). |

TABLE 1-4

| Example | Chemical formula | Physicochemical properties |
|---|---|---|
| 13 | | IR (ATR) cm$^{-1}$: 2950, 1606, 1547, 1439, 1278, 1182, 1133.<br>$^1$H-NMR (CDCl$_3$) δ: 0.95 (3 H, t, J = 7.1 Hz), 1.07-1.20 (2 H, m), 1.40-1.58 (9 H, m), 2.01 (1 H, m), 2.70-2.88 (4 H, m), 3.07 (3 H, s), 3.43 (2 H, t, J = 5.4 Hz), 3.76 (3 H, s), 4.41 (2 H, d, J = 5.4 Hz), 4.64 (1 H, d, J = 16.6 Hz), 4.88 (1 H, d, J = 16.6 Hz), 6.06 (1 H, q, J = 7.1 Hz), 6.48 (1 H, dd, J = 2.7, 8.6 Hz), 6.67 (1 H, d, J = 2.7 Hz), 6.92 (1 H, d, J = 8.6 Hz), 7.70 (1 H, s), 7.75 (2 H, s), 8.14 (2 H, s). |

TABLE 1-4-continued

| Example | Chemical formula | Physicochemical properties |
|---|---|---|
| 14 | 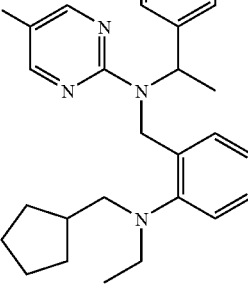 | ¹H-NMR (CDCl₃) δ: 0.94 (3 H, t, J = 7.1 Hz), 1.12-1.20 (2 H, m), 1.42-1.68 (9 H, m), 1.97 (1 H, m) 2.21 (3 H, s), 2.75-2.93 (6 H, m), 4.15 (2 H, t, J = 6.6 Hz), 4.65 (1 H, d, J = 17.3 Hz), 4.87 (1 H, d, J = 17.3 Hz), 6.23 (1 H, q, J = 6.8 Hz), 7.10-7.16 (2 H, m), 7.29 (1 H, s), 7.75 (1 H, s), 7.75 (2 H, s), 8.14 (2 H, s). |
| 15 |  | IR (ATR) cm⁻¹: 2958, 1606, 1548, 1477, 1421, 1278, 1171, 1132.<br>¹H-NMR (CDCl₃) δ: 0.94 (3 H, t, J = 7.1 Hz), 1.12-1.20 (2 H, m), 1.42-1.68 (9 H, m), 1.98 (1 H, m) 2.71 (3 H, s), 2.75-2.93 (4 H, m), 3.01-3.07 (1 H, m), 3.15-3.22 (1 H, m), 4.42-4.44 (2 H, m), 4.66 (1 H, d, J = 17.1 Hz), 4.87 (1 H, d, J = 17.1 Hz), 6.22 (1 H, q, J = 7.3 Hz), 7.08-7.16 (2 H, m), 7.30 (1 H, s), 7.71 (1 H, s), 7.75 (2 H, s), 8.16 (2 H, s). |
| 16 | 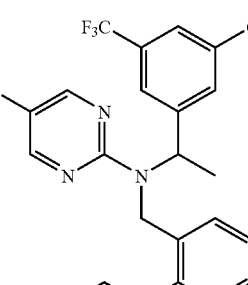 | IR (ATR) cm⁻¹: 2950, 1607, 1549, 1478, 1420, 1278, 1171, 1132.<br>¹H-NMR (CDCl₃) δ: 0.95 (3 H, t, J = 7.1 Hz), 1.06-1.19 (2 H, m), 1.40-1.62 (9 H, m), 1.98 (1 H, m) 2.76-2.95 (4 H, m), 3.08 (3 H, s), 3.45 (2 H, t, J = 5.1 Hz), 4.43 (2 H, t, J = 5.1 Hz), 4.67 (1 H, d, J = 17.3 Hz), 4.89 (1 H, d, J = 17.3 Hz), 6.22 (1 H, q, J = 7.1 Hz), 7.08 (1 H, d, J = 8.1 Hz), 7.15 (1 H, d, J = 8.1 Hz), 7.31 (1 H, s), 7.71 (1 H, s), 7.75 (2 H, s), 8.15 (2 H, s). |

TABLE 1-5

| Example | Chemical formula | Physicochemical properties |
|---|---|---|
| 17 | 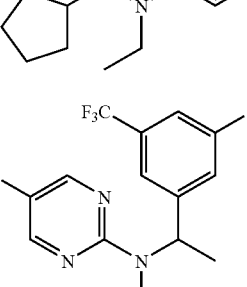 | ¹H-NMR (CDCl₃) δ: 0.98 (3 H, t, J = 7.1 Hz), 1.11-1.16 (2 H, m), 1.46-1.60 (6 H, m), 1.67 (3 H, d, J = 6.8 Hz), 2.04 (1 H, m), 2.19 (3 H, s), 2.20 (3 H, s), 2.78-2.89 (4 H, m), 2.99 (2 H, q, J = 7.1 Hz), 4.11 (2 H, t, J = 6.8 Hz), 4.83 (1 H, br), 5.21 (1 H, d, J = 13.9 Hz), 5.35 (1 H, d, J = 13.9 Hz), 6.95 (1 H, d, J = 8.3 Hz), 7.03 (1 H, d, J = 8.3 Hz), 7.52 (3 H, br s), 8.05 (2 H, s). |

TABLE 1-5-continued

| Example | Chemical formula | Physicochemical properties |
| --- | --- | --- |
| 18 | | ¹H-NMR (CDCl₃) δ: 0.98 (3 H, t, J = 7.1 Hz), 1.13-1.16 (2 H, m), 1.47-1.68 (9 H, m), 2.04 (1 H, m), 2.21 (3 H, s), 2.78-2.89 (2 H, m), 3.00 (2 H, q, J = 7.1 Hz), 3.07 (3 H, s), 3.42 (2 H, t, J = 5.2 Hz), 4.39 (2 H, t, J = 5.2 Hz), 4.81 (1 H, br), 5.22 (1 H, d, J = 13.7 Hz), 5.41 (1 H, d, J = 13.7 Hz), 6.96 (1 H, d, J = 8.3 Hz), 7.05 (1 H, d, J = 8.3 Hz), 7.51 (2 H, s), 7.54 (1 H, s), 8.06 (2 H, s). |
| 19 | | ¹H-NMR (CDCl₃) δ: 0.94 (3 H, t, J = 6.9 Hz), 1.10-1.18 (2 H, m), 1.40-1.66 (9 H, m), 1.98 (1 H, m), 2.20 (3 H, s), 2.75 (1 H, m), 2.84-2.91 (5 H, m), 4.14 (2 H, t, J = 6.7 Hz), 4.68 (1 H, d, J = 17.1 Hz), 4.93 (1 H, d, J = 17.1 Hz), 6.15 (1 H, q, J = 6.8 Hz), 6.93 (1 H, t, J = 7.1 Hz), 7.03 (1 H, d, J = 7.1 Hz), 7.09-7.17 (2 H, m), 7.70 (1 H, s), 7.77 (2 H, s), 8.13 (2 H, s). |
| 20 | | IR (ATR) cm⁻¹: 2947, 1607, 1548, 1477, 1277, 1132. ¹H-NMR (CDCl₃) δ: 0.94 (3 H, t, J = 7.1 Hz), 1.07-1.20 (2 H, m), 1.43-1.65 (9 H, m), 1.98 (1 H, m), 2.75 (1 H, m), 2.83-2.93 (3 H, m), 3.07 (3 H, s), 3.43 (2 H, t, J = 5.4 Hz), 4.41 (2 H, t, J = 5.4 Hz), 4.70 (1 H, d, J = 17.1 Hz), 4.95 (1 H, d, J = 17.1 Hz), 6.14 (1 H, q, J = 7.2 Hz), 6.93 (1 H, t, J = 7.1 Hz), 7.01 (1 H, d, J = 7.1 Hz), 7.10-7.17 (2 H, m), 7.71 (1 H, s), 7.77 (2 H, s), 8.14 (2 H, s). |

TABLE 1-6

| Example | Chemical formula | Physicochemical properties |
|---|---|---|
| 21 | | 1H-NMR (CDCl3) δ: 0.92 (3 H, t, J = 7.1 Hz), 1.03-2.00 (2 H, m), 1.40-1.67 (9 H, m), 1.94 (1 H, m), 2.22 (3 H, s), 2.68 (1 H, dd, J = 8.1, 12.7 Hz), 2.76 (1 H, dd, J = 6.8, 12.7 Hz), 2.82 (2 H, q, J = 7.1 Hz), 2.88 (2 H, t, J = 6.6 Hz), 4.15 (2 H, t, J = 6.6 Hz), 4.57 (1 H, d, J = 17.3 Hz), 4.78 (1 H, d, J = 17.3 Hz), 6.21 (1 H, q, J = 6.8 Hz), 6.82 (1 H, dd, J = 9.0, 117 Hz), 6.89 (1 H, dd, J = 7.3, 120 Hz), 7.72 (1 H, s), 7.75 (2 H, s), 8.14 (2 H, s). |
| 22 | | IR (ATR) cm$^{-1}$: 2953, 1607, 1549, 1504, 1478, 1277, 1132. 1H-NMR (CDCl3) δ: 0.92 (3 H, t, J = 7.1 Hz), 1.03-1.18 (2 H, s), 1.40 1.67 (9 H, m), 1.94 (1 H, m), 2.68 (1 H, dd, J = 7.8, 12.7 Hz), 2.76 (1 H, dd, J = 6.8, 12.7 Hz), 2.82 (2 H, q, J = 7.1 Hz), 3.08 (3 H, s), 3.45 (2 H, t, J = 5.6 Hz), 4.44 (2 H, t, J = 5.6 Hz), 4.59 (1 H, d, J = 16.8 Hz), 4.79 (1 H, d, J = 16.8 Hz), 6.20 (1 H, q, J = 7.1 Hz), 6.79 (1 H, dd, J = 9.3, 11 7 Hz), 6.90 (1 H, dd, J = 7.3, 12 0 Hz), 7.73 (1 H, s), 7.75 (2 H, s), 8.15 (2 H, s). |
| 23 | | 1H-NMR (CDCl3) δ: 0.94 (3 H, t, J = 7.1 Hz), 1.04-1.18 (2 H, m), 1.40-1.68 (9 H, m), 1.98 (1 H, m), 2.21 (3 H, s), 2.74 (1 H, dd, J = 8.1, 13.0 Hz), 2.79-2.91 (5 H, m), 4.14 (2 H, t, J = 6.6 Hz), 4.57 (1 H, d, J = 17.3 Hz), 4.82 (1 H, d, J = 17.3 Hz), 6.17 (1 H, q, J = 7.1 Hz), 6.88 (1 H, dd, J = 2.0, 8.3 Hz), 6.95 (1 H, d, J = 8.3 Hz), 7.04 (1 H, d, J = 2.0 Hz), 7.71 (1 H, s), 7.76 (2 H, s), 8.12 (2 H, s). |
| 24 | | IR (ATR) cm$^{-1}$: 2950, 1606, 1591, 1548, 1478, 1423, 1278, 1132. 1H-NMR (CDCl3) δ: 0.95 (3 H, t, J = 7.1 Hz), 1.04-1.20 (2 H, m), 1.40-1.69 (9 H, m), 1.98 (1 H, m), 2.74 (1 H, dd, J = 7.8, 12.9 Hz), 2.80-2.92 (5 H, m), 3.08 (3 H, s), 4.42 (2 H, t, J = 5.4 Hz), 4.59 (1 H, d, J = 17.1 Hz), 4.84 (1 H, d, J = 17.1 Hz), 6.16 (1 H, q, J = 6.8 Hz), 6.89 (1 H, dd, J = 2.0, 8.3 Hz), 6.93 (1 H, d, J = 8.3 Hz), 7.05 (1 H, d, J = 2.0 Hz), 7.72 (1 H, s), 7.75 (2 H, s), 8.14 (2 H, s). |

TABLE 1-7

| Example | Chemical formula | Physicochemical properties |
|---|---|---|
| 25 | 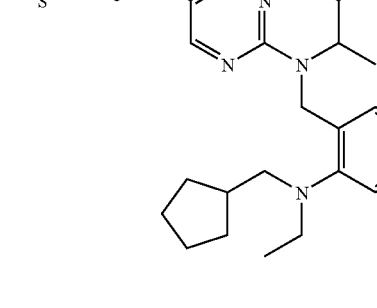 | ¹H-NMR (CDCl₃) δ: 0.91 (3 H, t, J = 7.1 Hz), 1.04-1.18 (2 H, m), 1.40-1.64 (9 H, m), 1.94 (1 H, m), 2.21 (3 H, s), 2.70 (1 H, m), 2.77-2.89 (5 H, m), 4.15 (2 H, t, J = 6.8 Hz), 4.65 (1 H, d, J = 17.3 Hz), 4.87 (1 H, d, J = 17.3 Hz), 6.22 (1 H, q, J = 7.1 Hz), 6.73 (1 H, dd, J = 3.2, 10.1 Hz), 6.83 (1 H, dt, J = 3.2, 8.8 Hz), 7.06 (1 H, dd, J = 5.1, 8.8 Hz), 7.71 (1 H, s), 7.77 (2 H, s), 8.13 (2 H, s). |
| 26 | 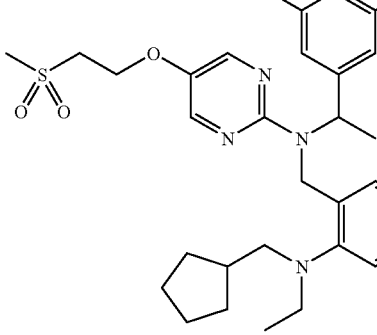 | IR (ATR) cm⁻¹: 2954, 1607, 1549, 1477, 1278, 1132. ¹H-NMR (CDCl₃) δ: 0.91 (3 H, t, J = 7.1 Hz), 1.05-1.16 (2 H, m), 1.42-1.64 (9 H, m), 1.94 (1 H, m), 2.68-2.86 (4 H, m), 3.08 (3 H, s), 3.44 (2 H, t, J = 5.4 Hz), 4.43 (2 H, t, J = 5.4 Hz), 4.66 (1 H, d, J = 17.6 Hz), 4.88 (1 H, d, J = 17.6 Hz), 6.20 (1 H, q, J = 7.2 Hz), 6.70 (1 H, dd, J = 2.9, 9.2 Hz), 6.84 (1 H, dt, J = 2.9, 8.8 Hz), 7.07 (1 H, dd, J = 5.4, 8.8 Hz), 7.72 (1 H, s), 7.77 (2 H, s), 8.15 (2 H, s). |
| 27 | 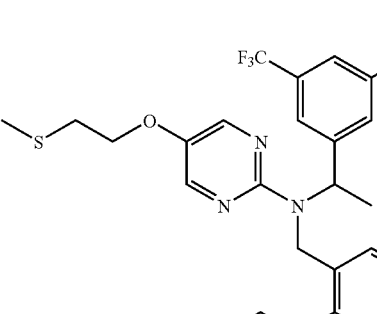 | ¹H-NMR (CDCl₃) δ: 0.94 (3 H, t, J = 7.1 Hz), 1.07-1.18 (2 H, m), 1.42-1.70 (9 H, m), 1.98 (1 H, m), 2.21 (3 H, s), 2.71-2.88 (6 H, m), 4.13 (2 H, t, J = 6.8 Hz), 4.55 (1 H, d, J = 17.3 Hz), 4.81 (1 H, d, J = 17.3 Hz), 6.17 (1 H, q, J = 7.1 Hz), 6.88 (1 H, d, J = 8.3 Hz), 7.04 (1 H, dd, J = 8.3 Hz, 2.0 Hz), 7.18 (1 H, d, J = 2.0 Hz), 7.71 (1 H, s), 7.76 (2 H, s), 8.12 (2 H, s). |
| 28 | 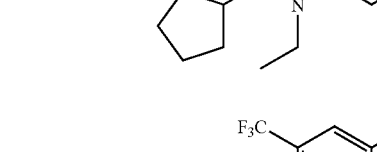 | IR (ATR) cm⁻¹: 2945, 1586, 1549, 1478, 1279, 1134. ¹H-NMR (CDCl₃) δ: 0.95 (3 H, t, J = 7.1 Hz), 1.05-1.20 (2 H, m), 1.44-1.67 (9 H, m), 1.98 (1 H, m), 2.71-2.88 (4 H, m), 3.07 (3 H, s), 3.44 (2 H, t, J = 5.1 Hz), 4.42 (2 H, t, J = 5.1 Hz), 4.57 (1 H, d, J = 17.1 Hz), 4.82 (1 H, d, J = 17.1 Hz), 6.16 (1 H, q, J = 7.6 Hz), 6.86 (1 H, d, J = 8.3 Hz), 7.03 (1 H, dd, J = 1.9, 8.3 Hz), 7.19 (1 H, d, J = 1.9 Hz), 7.72 (1 H, s), 7.75 (2 H, s), 8.14 (2 H, s). |

TABLE 1-8

| Example | Chemical formula | Physicochemical properties |
|---|---|---|
| 29 | | ¹H-NMR (CDCl₃) δ: 0.93 (3 H, t, J = 7.1 Hz), 1.05-1.20 (2 H, m), 1.40-1.65 (9 H, m), 1.95 (1 H, m), 2.21 (3 H, s), 2.70-2.89 (6 H, m), 4.16 (2 H, t, J = 7.3 Hz), 4.61 (1 H, d, J = 17.1 Hz), 4.84 (1 H, d, J = 17.1 Hz), 6.20 (1 H, q, J = 7.1 Hz), 6.95 (1 H, d, J = 8.5 Hz), 7.11 (1 H, d, J = 2.4 Hz), 7.25 (1 H, m), 7.72 (1 H, s), 7.77 (2 H, s), 8.14 (2 H, s). |
| 30 | | IR (ATR) cm⁻¹: 2958, 1608, 1550, 1474, 1377, 1278, 1176, 1133. ¹H-NMR (CDCl₃) δ: 0.93 (3 H, t, J = 7.1 Hz), 1.04-1.18 (2 H, m), 1.40-1.67 (9 H, m), 1.95 (1 H, m), 2.71-2.91 (4 H, m), 3.08 (3 H, s), 3.45 (2 H, t, J = 5.1 Hz), 4.44 (2 H, t, J = 5.1 Hz), 4.64 (1 H, d, J = 17.1 Hz), 4.86 (1 H, d, J = 17.1 Hz), 6.18 (1 H, q, J = 7.1 Hz), 6.97 (1 H, d, J = 8.5 Hz), 7.08 (1 H, d, J = 2.4 Hz), 7.26 (1 H, m), 7.73 (1 H, s), 7.76 (2 H, s), 8.15 (2 H, s). |
| 31 | | ¹H-NMR (CDCl₃) δ: 0.98 (3 H, t, J = 7.1 Hz), 1.07-1.23 (2 H, m), 1.39-1.75 (9 H, m), 2.01 (1 H, m), 2.22 (3 H, s), 2.81-3.05 (6 H, m), 4.17 (2 H, t, J = 6.6 Hz), 4.64 (1 H, d, J = 17.1 Hz), 4.87 (1 H, d, J = 17.1 Hz), 6.16 (1 H, q, J = 7.1 Hz), 7.13 (1 H, d, J = 8.2 Hz), 7.21 (2 H, br s), 7.72 (1 H, s), 7.78 (2 H, s), 8.15 (2 H, s). |
| 32 | | IR (ATR) cm⁻¹: 2949, 1613, 1550, 1477, 1418, 1268, 1134. ¹H-NMR (CDCl₃) δ: 0.98 (3 H, t, J = 7.1 Hz), 1.07-1.20 (2 H, m), 1.40-1.80 (9 H, m), 2.03 (1 H, m), 2.80-3.12 (7H, m), 3.46 (2 H, t, J = 5.8 Hz), 4.46 (2 H, t, J = 5.8 Hz), 4.66 (1 H, d, J = 17.1 Hz), 4.88 (1 H, d, J = 17.1 Hz), 6.15 (1 H, q, J = 7.1 Hz), 7.13-7.18 (2 H, m), 7.39 (1 H, d, J = 8.3 Hz), 7.73 (1 H, s), 7.75 (2 H, s), 8.17 (2 H, s). |

TABLE 1-9

| Example | Chemical formula | Physicochemical properties |
|---|---|---|
| 33 | | ¹H-NMR (CDCl₃) δ: 0.86 (3 H, t, J = 7.3 Hz), 1.01 (3 H, t, J = 7.1 Hz), 1.12-1.75 (8H, m), 1.92-2.09 (3 H, m), 2.22 (3 H, s), 2.82-3.02 (6 H, m), 4.16 (2 H, t, J = 6.5 Hz), 4.72 (1 H, d, J = 17.1 Hz), 4.85 (1 H, d, J = 17.1 Hz), 6.02 (1 H, t, J = 7.8 Hz), 7.03 (1 H, s), 7.11 (1 H, d, J = 8.3 Hz), 7.31(1 H, d, J = 8.3 Hz), 7.66 (1 H, s), 7.78 (2 H, s), 8.15 (2 H, s). |
| 34 | | IR (ATR) cm⁻¹: 2942, 1613, 1549, 1475, 1277, 1172, 1132. ¹H-NMR (CDCl₃) δ: 0.87 (3 H, t, J = 7.1 Hz), 1.02 (3 H, t, J = 7.1 Hz), 1.10-1.35 (2 H, m), 1.37-1.75 (6 H, m), 1.85-2.10 (3 H, m) 2.81-3.09 (7H, m), 3.45 (2 H, t, J = 5.1 Hz), 4.45 (2 H, t, J = 5.1 Hz), 4.73 (1 H, d, J = 16.8 Hz), 4.87 (1 H, d, J = 16.8 Hz), 6.02 (1 H, m), 6.98 (1 H, s), 7.12 (1 H, d, J = 8.3 Hz), 7.30 (1 H, m), 7.67 (1 H, s), 7.76 (2 H, s), 8.17 (2 H, s). |
| 35 | | ¹H-NMR (CDCl₃) δ: 1.47 (3 H, d, J = 7.0 Hz), 1.50-1.75 (6 H, m), 2.23 (3 H, s), 2.67-2.84 (4 H, m), 2.90 (2 H, t, J = 6.6 Hz), 4.18 (2 H, t, J = 6.6 Hz), 4.72 (1 H, d, J =16.5 Hz), 4.78 (1 H, d, J = 16.5 Hz), 6.19 (1 H, q, J = 7.0 Hz), 6.94 (1 H, d, J = 8.3 Hz), 7.31 (1 H, s),7.34 (1 H, d, J = 8.3 Hz), # 7.63 (1 H, s), 7.72 (2 H, s), 8.19 (2 H, s). |
| 36 | | ¹H-NMR (CDCl₃) δ:1.48 (3 H, d, J = 7.0 Hz), 1.50-1.74 (6 H, m), 2.66-2.84 (4 H, m), 3.10 (3 H, s), 3.47 (2 H, t, J = 5.4 Hz), 4.47 (2 H, t, J = 5.4 Hz), 4.73 (1 H, d, J = 16.6 Hz), 4.80 (1 H, d, J = 16.6 Hz), 6.18 (1 H, q, J = 7.0 Hz), 6.95 (1 H, d, J = 8.5Hz), 7.29 (1 H, s), 7.35 (1 H, d, J = 8.5 Hz), 7.64 (1 H, s), 7.71 (2 H, s), 8.20 (2 H, s). |

TABLE 1-10

| Example | Chemical formula | Physicochemical properties |
|---|---|---|
| 37 | | $^1$H-NMR (CDCl$_3$) δ: 1.51 (3 H, d, J = 7.1 Hz), 2.23 (3 H, s), 2.71-2.88 (4 H, m), 2.89 (2 H, t, J = 6.6 Hz), 3.70-3.84 (4 H, m), 4.19 (2 H, t, J = 6.6 Hz), 4.73 (1 H, d, J = 17.1 Hz), 4.79 (1 H, d, J = 17.1 Hz), 6.22 (1H, q, J = 7.1 Hz), 6.97 (1H, d, J = 8.3 Hz), 7.31 (1 H, s), 7.37 (1 H, d, J = 8.3 Hz), 7.62 (1 H, s), 7.69 (2 H, s), 8.19 (2 H, s). |
| 38 | | IR (ATR) cm$^{-1}$: 2970, 2852, 1612, 1551, 1504, 1483. $^1$H-NMR (CDCl$_3$) δ: 1.52 (3 H, d, J = 7.0 Hz), 2.68-2.9 1 (4 H, m), 3.10 (3 H, s), 3.47 (2 H, t, J = 5.3 Hz), 3.68-3.85 (4 H, m), 4.47 (2 H, t, J = 5.3 Hz), 4.75 (1 H, d, J = 17.3 Hz), 4.80 (1 H, d, J = 17.3 Hz), 6.22 (1 H, q, J = 7.0 Hz), 6.98 (1 H, d, J = 8.3 Hz), 7.28 (1 H, s), 7.38 (1 H, d, J = 8.3 Hz), 7.63 (1 H, s), 7.68 (2 H, s), 8.21 (2 H, s). |
| 39 | | $^1$H-NMR (CDCl$_3$) δ: 0.98 (3 H, d, J = 6.6 Hz), 1.13-1.35 (2 H, m), 1.37-1.57 (4 H, m), 1.67 (2 H, br t, J = 15.1 Hz), 2.23 (3 H, s), 2.50-2.74 (2 H, m), 2.78-2.94 (3 H, m), 2.99 (1 H, br d, J = 11.5 Hz), 4.18 (2 H, t, J = 6.7 Hz), 4.71 (1 H, d, J = 16.5 Hz), 4.79 (1 H, d, J = 16.5 Hz), 6.18 (1 H, q, J = 7.1 Hz), 6.95 (1 H, d, J = 8.5 Hz), 7.30 (1 H, s), 7.34 (1 H, d, J = 8.5 Hz), 7.63 (1 H, s), 7.71 (2 H, s), 8.19 (2 H, s). |
| 40 | | IR (ATR) cm$^{-1}$: 2931, 1614, 1549, 1479, 1420, 1378. $^1$H-NMR (CDCl$_3$) δ: 0.98 (3 H, d, J = 6.4 Hz), 1.12-1.36 (2 H, m), 1.40-1.55 (4 H, m), 1.72 (2 H, br t, J = 12.6 Hz), 2.5 1-2.72 (2 H, m), 2.85 (1 H, d, J = 12.6 Hz), 2.99 (1 H, d, J = 12.6 Hz), 3.10 (3 H, s), 3.47 (2 H, t, J = 5.3 Hz), 4.47 (2 H, t, J = 5.3 Hz), 4.74 (1 H, d, J = 16.3 Hz), 4.81 (1 H, d, J = 16.3 Hz), 6.18 (1 H, q, J = 7.0 Hz), 6.97 (1 H, d, J = 8.4 Hz), 7.29 (1 H, s), 7.35 (1 H, d, J = 8.4 Hz), 7.64 (1 H, s), 7.71 (2 H, s), 8.21 (2 H, s). |

TABLE 1-11

| Example | Chemical formula | Physicochemical properties |
|---|---|---|
| 41 | | ¹H-NMR (CDCl₃) δ: 1.19 (3 H, d, J = 6.1 Hz), 1.20 (3 H, d, J = 6.3 Hz), 1.51 (3 H, d, J = 6.9 Hz), 2.23 (3 H, s), 2.34-2.47 (2 H, m), 2.64 (1 H, d, J = 11.6 Hz), 2.82 (1 H, d, J = 11.6 Hz), 2.90 (2 H, t, J = 6.7 Hz), 3.62-3.82 (2 H, m), 4.19 (2 H, t, J = 6.7 Hz), 4.74 (2 H, s), 6.20 (1 H, q, J = 6.9 Hz), 6.91 (1 H, d, J = 8.3 Hz), 7.30 (1 H, s), 7.34 (1 H, d, J = 8.3 Hz), 7.60 (1 H, s), 7.66 (2 H, s), 8.20 (2 H, s). |
| 42 | | IR (ATR) cm⁻¹: 2977, 2939, 2880, 1613, 1549, 1479. ¹H-NMR (CDCl₃) δ: 1.19 (3 H, d, J = 6.1 Hz), 1.20 (3 H, d, J = 6.3 Hz), 1.52 (3 H, d, J = 7.1 Hz), 2.35-2.50 (2 H, m), 2.65 (1 H, d, J = 11.2 Hz), 2.82 (1 H, d, J = 11.7 Hz), 3.10 (3 H, s), 3.48 (2 H, t, J = 5.3 Hz), 3.60-3.80 (2 H, m), 4.48 (2 H, t, J = 5.3 Hz), 4.76 (2 H, s), 6.20 (1 H, q, J = 7.1 Hz), 6.92 (1 H, d, J = 8.3 Hz), 7.28 (1 H, s), 7.35 (1 H, d, J = 8.3 Hz), 7.61 (1 H, s), 7.65 (2 H, s), 8.22 (2 H, s). |
| 43 | | ¹H-NMR (CDCl₃) δ: 0.86-0.95 (7 H, m), 1.24 (3 H, t, J = 7.2 Hz), 1.35-1.45 (4 H, m), 1.65 1.80 (5 H, m), 2.14 (2 H, d, J = 6.8 Hz), 2.21 (3 H, s), 2.69 (1 H, m) 2.82-2.91 (5 H, m), 4.11 (2 H, q, J = = 7.2 Hz), 4.16 (2 H, t, J = 6.8 Hz), 4.62 (1 H, d, J = 16.8 Hz), 4.86 (1 H, d, J = 16.8 Hz), 6.21 (1 H, q, J = 7.1 Hz), 7.11 (1 H, d, J = 8.3 Hz), 7.22 (1 H, s), 7.37 (1 H, d, J = 8.3 Hz), 7.70 (1 H, s), 7.73 (2 H, s), 8.14 (2 H, s). |

TABLE 1-12
| Example | Chemical formula | Physicochemical properties |
|---|---|---|
| 44 | 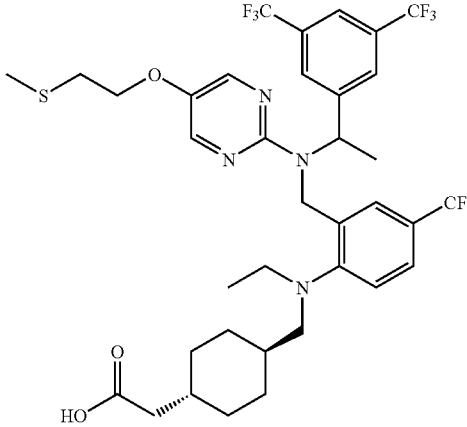 | $^1$H-NMR (CDCl$_3$) δ: 0.85-0.96 (7 H, m), 1.35-1.45 (4 H, m), 1.60-1.78 (5 H, m), 2.18-2.21 (5 H, m), 2.69 (1 H, m), 2.81-2.91 (5 H, m), 4.16 (2 H, t, J = 6.8 Hz), 4.61 (1 H, d, J = 17.1 Hz), 4.85 (1 H, d, J = 17.1 Hz), 6.22 (1 H, q, J = 6.8 Hz), 7.11 (1 H, d, J = 8.3 Hz), 7.23 (1 H, s), 7.37 (1 H, d, J = 8.3 Hz), 7.70 (1 H, s), 7.73 (2 H, s), 8.14 (2 H, s). |
| 45 | 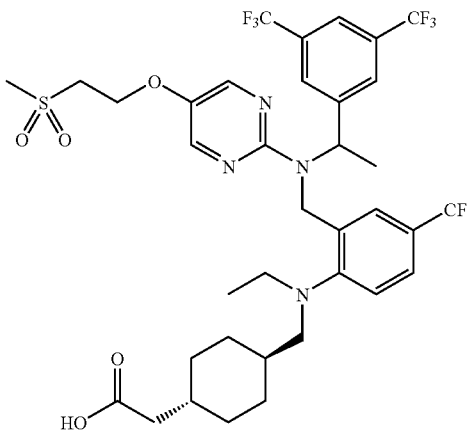 | IR (ATR) cm$^{-1}$: 2921, 1706, 1653, 1618, 1558, 1479, 1279, 1134. $^1$H-NMR (CDCl$_3$) δ: 0.80-0.96 (7 H, m), 1.38 (1 H. m), 1.47 (3 H, d, J = 7.1 Hz), 1.65-1.77 (5 H, m), 2.19(2 H, d, J = 6.8Hz), 2.72 (1 H, m), 2.81-2.91 (3 H, m), 3.08 (3 H, s), 3.45 (2 H, t, J = 5.4 Hz), 4.44 (2 H, t, J = 5.4 Hz), 4.62 (1 H, d, J = 17.1 Hz), 4.86 (1 H, d, J = 17.1 Hz), 6.21 (1 H, q, J = 7.1 Hz), 7.13 (1 H, d, J = 8.3 Hz), 7.19 (1 H, s), 7.38 (1 H, d, J = 8.3 Hz), 7.71 (1 H, s), 7.73 (2 H, s), 8.15 (2 H, s). |
| 46 | 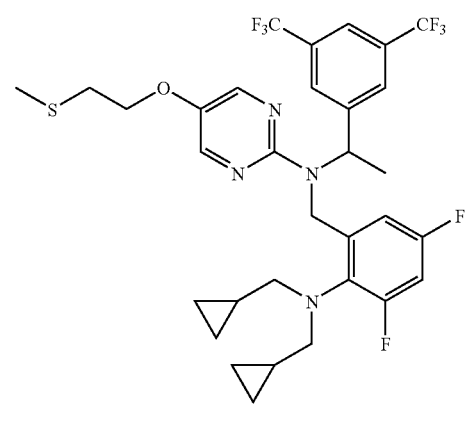 | $^1$H-NMR (CDCl$_3$) δ: −0.13-0.07 (4 H, m), 0.23-0.42 (4 H, m), 0.67-0.78 (2 H, m), 1.58 (3 H, d, J = 7.3 Hz), 2.21 (3 H, s), 2.75-2.96 (6 H, m), 4.14 (2 H, t, J = 6.8 Hz), 4.77 (1 H, d, J = 17.6 Hz), 4.98 (1 H, d, J = 17.6 Hz), 6.24 (1 H, q, J = 7.3 Hz), 6.53 (1 H, m), 6.60 (1 H, ddd, J = 3.2, 8.6, 11.7 Hz), 7.72 (1 H, s), 7.78 (2 H, s), 8.09 (2 H, s). |

TABLE 1-13

| Example | Chemical formula | Physicochemical properties |
|---|---|---|
| 47 | (structure) | IR (ATR) cm$^{-1}$:1606, 1549, 1475, 1278, 1176, 1133. $^1$H-NMR (CDCl$_3$) δ: −0.12-0.08 (4 H, m), 0.24-0.38 (4 H, m), 0.67 0.79 (2 H, m), 1.59 (3 H, d, J = 7.3 Hz), 2.78 (2 H, d, J = 6.8 Hz), 2.83 (1 H, dd, J = 6.8, 13.1 Hz), 2.92 (1 H, dd, J = 6.8, 13.1 Hz), 3.07 (3 H, s), 3.44 (2 H, t, J = 5.4 Hz), 4.42 (2 H, t, J = 5.4 Hz), 4.79 (1 H, d, J = 17.8 Hz), 5.00 (1 H, d, J = 17.8 Hz), 6.23 (1 H, q, J = 7.3 Hz), 6.49 (1 H, dd, J = 2.7, 9.5 Hz), 6.61 (1 H, ddd, J = 2.7, 8.8, 11.5 Hz), 7.73 (1 H, s), 7.77 (2 H, s), 8.11 (2 H, s). |

Test Example 1

Measurement of CETP Inhibitory Action in Human Plasma

A solution obtained by dissolving an exemplary compound in polyethylene glycol/N-methyl-2-pyrrolidone (vol/vol=1/1) was added to human plasma, and the mixture was incubated in an incubator at 37° C. for 4 hours. The CETP activity in this plasma was measured with Cholesteryl Ester Transfer Protein Activity kit (Roar Biomedical, catalog No.: RB-CETP). Specifically, to each well of a 96-well plate, 95 µL of a buffer (10 mM Tris, 150 mM NaCl, 2 mM EDTA, pH 7.4), 2 µL of Donor particle and 2 µL of Acceptor particle were added, 1 µL of the human plasma after the incubation was added to the mixture, and the mixture was incubated in an incubator at 37° C. for 2 hours. After completion of the incubation, fluorescence intensity (FLU) was measured with a fluorescence plate reader (excitation wavelength: 465 nm, emission wavelength: 535 nm). In accordance with the following equation 1, the CETP activity (% of control) was obtained for the compounds of the examples for two or more concentrations.

CETP activity (% of control)=(Sample *FLU*–Blank *FLU*)×100/(Control *FLU*–Blank *FLU*)    (Equation 1)

In the equation, the terms have the following meanings:

Blank FLU: Fluorescence intensity of sample not added with plasma

Control FLU: Fluorescence intensity of plasma not added with solution of compound Sample FLU: Fluorescence intensity of plasma added with solution of compound A value obtained by subtracting the value of the CETP activity from 100 was defined as the CETP inhibitory rate of each exemplary compound, and a concentration inhibiting the CETP activity by 50% (IC$_{50}$) was calculated for each exemplary compound from the values of the CETP inhibitory rate at two or more concentrations. The results are shown in Table 2.

TABLE 2

| Example No. | IC$_{50}$ (µM) |
|---|---|
| 2 | 0.04 |
| 3 | 0.03 |
| 5 | 0.05 |
| 7 | 0.3 |
| 9 | 0.07 |
| 11 | 0.25 |
| 13 | 0.1 |
| 15 | 0.3 |
| 16 | 0.15 |
| 20 | 0.8 |
| 22 | 0.5 |
| 24 | 0.3 |
| 26 | 0.25 |
| 28 | 0.2 |
| 30 | 0.045 |
| 32 | 0.03 |
| 45 | 0.12 |
| 47 | 0.4 |

Test Example 2

Measurement of Blood HDL Cholesterol Increasing Action in Normal Hamsters

N-{1-[3,5-Bis(trifluoromethyl)phenyl]ethyl}-N-({2-[(cyclopentylmethyl)(ethyl)amino]-5-(trifluoromethyl) phenyl}methyl)-5-[2-(methylsulfonyl)ethoxy]pyrimidin-2-amine (Example 3), or 4(S)-[(3,5-bis-trifluoromethylbenzyl) methoxycarbonylamino]-2(R)-ethyl-6-trifluoromethyl-3,4-dihydro-2H-quinoline-1-carboxylic acid ethyl ester (Torcetrapib) disclosed in International Patent Publication WO2000/17164 was suspended in a 5% Tween 80 solution (control vehicle), and then repeatedly administered to normal hamsters (male Syrian Hamsters) by oral administration once a day over 7 days by using a metal catheter. Two hours after the administration on day 7 of the administration, blood was collected, and plasma was obtained. Plasma lipoproteins were analyzed by automatic measurement using a HPLC system based on the postlabeling method according to the method described in J. Lipid. Res., 43, pp. 805-814. Specifically, 15 µL of a plasma sample was diluted 10 times with PBS containing 1 mM EDTA, and then injected in a volume of 80 µL into a gel filtration column (Superose 6 column, column size: 10×300 mm, GE Healthcare Bioscience) connected to a HPLC system (liquid feeding unit: Shimadzu LC-20A System, Shimadzu). Separation was performed by using PBS containing 1 mM EDTA as a running buffer at a flow rate of 0.5 mL/min and at a column temperature of 40° C. The eluate from the column was mixed with a cholesterol measurement reagent (Cholesterol E-Test Wako, Wako Pure Chemical Industries) at a flow rate of 0.25 mL/min, and the reaction was allowed in a reaction coil (0.5 mm×15 m) at 40° C. during the feeding. Cholesterols in the eluate from the reaction coil were detected at a wavelength of 600 nm. An area ratio of the HDL fraction relative to the total area of the obtained cholesterols was calculated, and HDL cholesterol level was calculated by multiplying the total cholesterol level measured beforehand using Cholesterol E Test Wako by the area ratio of the HDL fraction. Five normal hamsters grouped beforehand on the basis of the total plasma cholesterol level were used for each of the control group (control vehicle administration group) and the compound administration groups (groups administered with the compound of Example 3 at 10 mg/kg, 30 mg/kg and 100 mg/kg, and Torcetrapib at 10 mg/kg and 100 mg/kg).

The plasma HDL cholesterol concentrations of the groups (HDL-C, mg/dl) are shown in FIG. 1 and Table 3. The symbols * and *** used in FIG. 1 and Table 3 indicate presence of significant difference at a risk ratio lower than 5% (p<0.05) and a risk ratio lower than 0.1% (p<0.001), respectively, in a multi-group comparison test (Dunnett's multiple comparison test) performed between the control group and each compound administration group. Further, increasing ratios of HDL cholesterol level in each group relative to the control group were calculated as HDL cholesterol increasing ratios in accordance with the following equation 2, and indicated in terms of %. The results are shown in Table 3.

HDL cholesterol increasing ratio (%)=[(Average HDL cholesterol level of each compound administration group−Average HDL cholesterol level of control group)/Average HDL cholesterol level of control group]×100 (Equation 2)

TABLE 3

| Compound | Dose (mg/kg) | Average HDL cholesterol level ± SD (mg/dl) | HDL cholesterol increasing ratio (%) |
|---|---|---|---|
| Control | — | 86.4 ± 3.7 | — |
| Example 3 | 10 | 118.5 ± 7.6*** | 37.1 |
|  | 30 | 124.4 ± 8.4*** | 43.9 |
|  | 100 | 126.9 ± 13.2*** | 46.8 |
| Torcetrapib | 10 | 90.6 ± 7.7 | 4.8 |
|  | 100 | 113.0 ± 23.2* | 30.7 |

(n = 5)

On the basis of the aforementioned test results, it was revealed that the compounds of the present invention, salts thereof and solvates thereof had potent CETP inhibitory activity and blood HDL cholesterol increasing action, and could be suitably used as active ingredients of CETP inhibitors and HDL increasing agents. It was further revealed that, on the basis of the CETP inhibitory activity and blood HDL cholesterol increasing action, they can be suitably used as active ingredients of medicaments, more specifically, medicaments for prophylactic and/or therapeutic treatment of diseases including dyslipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like.

INDUSTRIAL APPLICABILITY

As specifically shown in the test examples, the compounds of the present invention, salts thereof, and solvates thereof exhibit potent inhibitory activity on CETP, and further have a potent blood HDL cholesterol increasing action, and therefore they can suitably be used as active ingredients of CETP inhibitors and active ingredients of HDL increasing agents. Further, on the basis of the inhibitory activity on CETP and the blood HDL cholesterol increasing action, they can suitably be used as active ingredients of medicaments, more specifically, active ingredients of medicaments for prophylactic or therapeutic treatment of diseases including dyslipidemia (hyperlipidemia), arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension and the like. Moreover, they can also be suitably used as active ingredients of the aforementioned medicaments showing low CYP inhibitory action.

The present application enjoys the benefit of the conventional priority claimed on the basis of the U.S. Provisional Patent Application No. 60/911,620, which was filed on Apr. 13, 2007, and the entire disclosure of the provisional application is incorporated into this specification.

What is claimed is:

1. A compound represented by the following general formula (I):

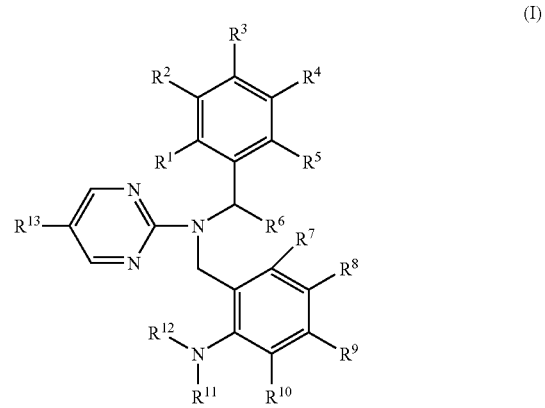

or a salt thereof wherein
$R^1$, $R^2$, $R^3$, $R^4$ and $R^5$ are the same or different, and represent a hydrogen atom, a halo($C_1$-$C_6$ alkyl) group, or a cyano group,
$R^6$ represents a $C_1$-$C_6$ alkyl group,
$R^7$, $R^8$, $R^9$ and $R^{10}$ are the same or different, and represent a hydrogen atom, a halogen atom, a $C_1$-$C_6$ alkyl group, a halo($C_1$-$C_6$ alkyl) group, or a $C_1$-$C_6$ alkoxy group,
$R^{11}$ and $R^{12}$ are the same or different, and represent a $C_1$-$C_6$ alkyl group, or a ($C_3$-$C_8$ cycloalkyl)($C_1$-$C_6$ alkyl) group, wherein the ($C_3$-$C_8$ cycloalkyl)($C_1$-$C_6$ alkyl) group may have one hydroxycarbonyl($C_1$-$C_6$ alkyl) group or ($C_1$-$C_6$ alkoxy)carbonyl($C_1$-$C_6$ alkyl) group as a substituent on the cycloalkyl group, or $R^{11}$ and $R^{12}$ combine to form a morpholino group or a piperidino group together with the adjacent nitrogen atom, wherein the morpholino group or the piperidino group may have 1 or 2 $C_1$-$C_6$ alkyl groups as a substituent, and $R^{13}$ represents a ($C_1$-$C_6$ alkyl)thio($C_1$-$C_6$ alkoxy) group, a ($C_1$-$C_6$ alkyl)sulfinyl($C_1$-$C_6$ alkoxy) group, or a ($C_1$-$C_6$ alkyl)sulfonyl($C_1$-$C_6$ alkoxy) group, and the general formula (I) represents both individual enantiomers and mixtures thereof.

2. The compound or a salt thereof according to claim 1, wherein the compound represented by the general formula (I) is:

N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfinyl)ethoxy]pyrimidin-2-amine, N-{1-[3,5-bis(trifluoromethyl)phenyl]ethyl}-N-({2-[(cyclopentylmethyl)(ethyl)amino]-5-(trifluoromethyl)phenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-5-methoxyphenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-5-methoxyphenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-3,5-difluorophenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-3,5-difluorophenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-5-methylphenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-5-methylphenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-4-fluorophenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-4-fluorophenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-4-methoxyphenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-4-methoxyphenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfinyl)ethoxy]pyrimidin-2-amine, N-{1-[3,5-bis(trifluoromethyl)phenyl]ethyl}-N-({2-[(cyclopentylmethyl)(ethyl)amino]-4-(trifluoromethyl)phenyl}methyl)-5-[2-(methylsulfonyl)ethoxy]pyrimidin-2-amine, N-{1-[3,5-bis(trifluoromethyl)phenyl]ethyl}-N-({2-chloro-6-[(cyclopentylmethyl)(ethyl)amino]-3-methylphenyl}methyl)-5-[2-(methylthio)ethoxy]pyrimidin-2-amine, N-{1-[3,5-bis(trifluoromethyl)phenyl]ethyl}-N-({2-chloro-6-[(cyclopentylmethyl)(ethyl)amino]-3-methylphenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]phenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]phenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-4,5-difluorophenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-4,5-difluorophenyl}methyl)-5-[2-(methylsulfonyl)ethoxy]pyrimidin-2-amine, N-{1-[3,5-bis(trifluoromethyl)phenyl]ethyl}-N-({4-chloro-2-[(cyclopentylmethyl)(ethyl)amino]phenyl}methyl)-5-[2-(methylthio)ethoxy]pyrimidin-2-amine, N-{1-[3,5-bis(trifluoromethyl)phenyl]ethyl}-N-({4-chloro-2-[(cyclopentylmethyl)(ethyl)amino]phenyl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-5-fluorophenyl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-5-fluorophenyl}methyl)-5-[2-(methylsulfonyl)ethoxy]pyrimidin-2-amine, N-{1-[3,5-bis(trifluoromethyl)phenyl]ethyl}-N-({4-bromo-2-[(cyclopentylmethyl)(ethyl)amino]phenyl}methyl)-5-[2-(methylthio)ethoxy]pyrimidin-2-amine, N-{1-[3,5-bis(trifluoromethyl)phenyl]ethyl}-N-({4-bromo-2-[(cyclopentylmethyl)(ethyl)amino]phenyl}methyl)-5-[2-(methylsulfonyl)ethoxy]pyrimidin-2-amine, N-{1-[3,5-bis(trifluoromethyl)phenyl]ethyl}-N-({5-bromo-2-[(cyclopentylmethyl)(ethyl)amino]phenyl}methyl)-5-[2-(methylthio)ethoxy]pyrimidin-2-amine, N-{1-[3,5-bis(trifluoromethyl)phenyl]ethyl}-N-({5-bromo-2-[(cyclopentylmethyl)(ethyl)amino]phenyl}methyl)-5-[2-(methylsulfonyl)ethoxy]pyrimidin-2-amine, 3-{1-[({2-[(cyclopentylmethyl)(ethyl)amino]-5-trifluoromethylphenyl}methyl){5-[2-(methylthio)ethoxy]pyrimidin-2-yl}amino]ethyl}-5-(trifluoromethyl)benzonitrile, 3-{1-[({2-[(cyclopentylmethyl)(ethyl)amino]-5-trifluoromethylphenyl}methyl) {5-[2-(methylsulfonyl)ethoxy]pyrimidin-2-yl}amino]ethyl}-5-(trifluoromethyl)benzonitrile, N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylthio)ethoxy]pyrimidin-2-amine, N-{1-[3,5-bis(trifluoromethyl)phenyl]propyl}-N-({2-[(cyclopentylmethyl)(ethyl)amino]-5-(trifluoromethyl)phenyl}methyl)-5-[2-(methylsulfonyl)ethoxy]pyrimidin-2-amine, N-{1-[3,5-bis(trifluoromethyl)phenyl]ethyl}-N-{[2-(piperidino)-5-(trifluoromethyl)phenyl]methyl}-5-[2-(methylthio)ethoxy]pyrimidin-2-amine, N-{1-[3,5-bis(trifluoromethyl)phenyl]ethyl}-N-{[2-(piperidino)-5-(trifluoromethyl)phenyl]methyl}-5-[2-(methylsulfonyl)ethoxy]pyrimidin-2 amine, N-{1-[3,5-bis(trifluoromethyl)phenyl]ethyl}-N-{[2-(morpholino)-5-(trifluoromethyl)phenyl]methyl}-5-[2-(methylthio)ethoxy]pyrimidin-2-amine, N-{1-[3,5-bis(trifluoromethyl)phenyl]ethyl}-N-{[2-(morpholino)-5-(trifluoromethyl)phenyl]methyl}-5-[2-(methylsulfonyl)ethoxy]pyrimidin-2-amine, N-{1-[3,5-bis(trifluoromethyl)phenyl]ethyl}-N-{[2-(4-methylpiperidino)-5-(trifluoromethyl)phenyl]methyl}-5-[2-(methylthio)ethoxy]pyrimidin-2-amine, N-{1-[3,5-bis(trifluoromethyl)phenyl]ethyl}-N-{[2-(4-methylpiperidino)-5-(trifluoromethyl)phenyl]methyl}-5-[2-(methylsulfonyl)ethoxy]pyrimidin-2-amine, N-{1-[3,5-bis(trifluoromethyl)phenyl]ethyl}-N-{[2-(cis-2,6-dimethylmorpholino)-5-(trifluoromethyl)phenyl]methyl}-5-[2-(methylthio)ethoxy]pyrimidin-2-amine, N-{1-[3,5-bis(trifluoromethyl)phenyl]ethyl}-N-{[2-(cis-2,6-dimethylmorpholino)-5-(trifluoromethyl)phenyl]methyl}-5-[2-(methylsulfonyl)ethoxy]pyrimidin-2-amine, ethyl trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetate, trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid, trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, N-({2-[bis(cyclopropylmethyl)amino]-3,5-difluorophenyl}methyl)-N-{1-[3,5-bis(trifluoromethyl)phenyl]ethyl}-5-[2-(methylthio)ethoxy]pyrimidin-2-amine, or N-({2-[bis(cyclopropylmethyl)amino]-3,5-difluorophenyl}methyl)-N-{1-[3,5-bis(trifluoromethyl)phenyl]ethyl}-5-[2-(methylsulfonyl)ethoxy]pyrimidin-2-amine.

3. A medicament composition containing the compound or a salt thereof according to claim 1, as an active ingredient.

4. A pharmaceutical composition containing the compound or a salt thereof according to claim 1 and a pharmaceutically acceptable carrier.

5. A method for therapeutic treatment of a dyslipidemia, which comprises administering a therapeutically effective amount of the compound or a salt thereof according to claim 1 to a mammal.

6. The method according to claim 5 wherein the mammal is a human.

\* \* \* \* \*